United States Patent [19]
Ishikawa et al.

[11] Patent Number: 5,114,918
[45] Date of Patent: May 19, 1992

[54] ENDOTHELIN ANTAGONISTIC CYCLIC PENTAPEPTIDES

[75] Inventors: Kiyofumi Ishikawa; Takehiro Fukami; Takashi Hayama; Kenji Niiyama; Toshio Nagase; Toshiaki Mase; Kagari Fujita; Masaru Nishikibe; Masaki Ihara; Mitsuo Yano, all of Tokyo, Japan

[73] Assignee: Banyu Pharmaceutical Co., Ltd., Tokyo, Japan

[21] Appl. No.: 630,505

[22] Filed: Dec. 20, 1990

[30] Foreign Application Priority Data

Dec. 28, 1989 [JP] Japan .................... 1-342695
Jul. 13, 1990 [JP] Japan .................... 2-185867

[51] Int. Cl.$^5$ .................. A61K 37/02; C07K 7/54; C07K 7/64
[52] U.S. Cl. .................... 514/11; 514/826; 514/921; 514/922; 514/929; 530/317; 530/321; 530/333; 530/800; 930/270; 930/DIG. 536; 930/DIG. 546
[58] Field of Search ............ 530/317, 321, 332, 800; 514/9, 11, 822, 826, 921, 922, 929

[56] References Cited

U.S. PATENT DOCUMENTS 4,981,950 1/1991 Masaki et al. ............ 530/326

FOREIGN PATENT DOCUMENTS 0127899 12/1984 European Pat. Off. .
0135722 4/1985 European Pat. Off. .

OTHER PUBLICATIONS

Stedman's Medical Dictionary, 25th Edition, pp. 1433–1434, Williams and Wilkins, Baltimore (1990).

Primary Examiner—Christina Chan
Attorney, Agent, or Firm—Oblon, Spivak, McClelland, Maier & Neustadt

[57] ABSTRACT

Cyclic pentapeptides of the formula:

$$\text{cyclo } (-X^1-X^2-X^3-X^4-X^5-) \qquad (I)$$

wherein $X^n$ ($n=1-5$) represents amino acid residues. These compounds are useful as hypotensive drugs.

2 Claims, 8 Drawing Sheets

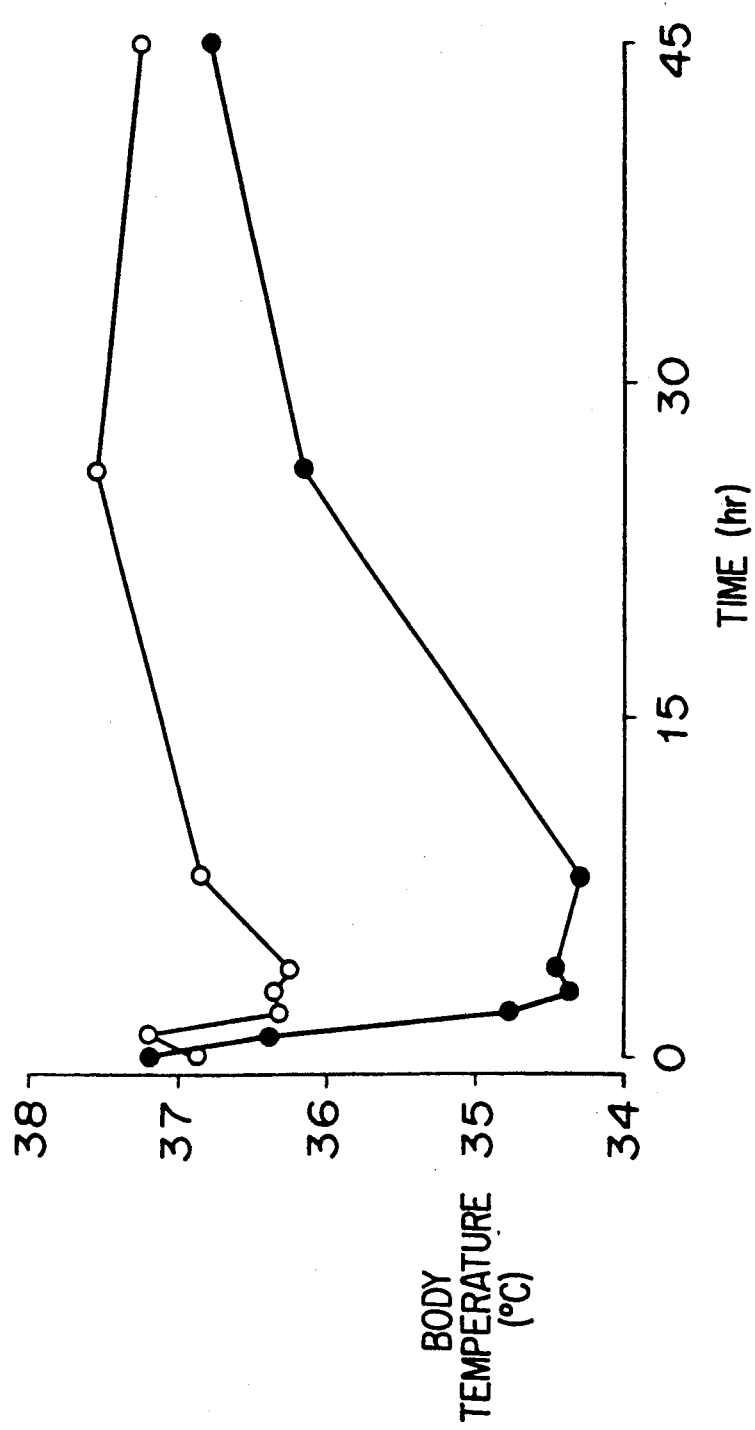

ENDOTHELIN ANTAGONISTIC CYCLIC PENTAPEPTIDES

The present invention relates to novel compounds having antagonism against a physiologically highly active endogenous peptide, endothelin, processes for their preparation and their use as a drug.

The compounds of the present invention have antagonism against endothelin, and thereby providing a new therapeutic potential, particularly for the treatment of hypertension, myocardial infarction, angina pectoris, acute renal failure, cerebral infarction, cerebral vasospasm, asthma, endotoxin shock, endotoxin-induced multiple organ failure or disseminated intravascular coagulation, and/or cyclosporin-induced renal failure or hypertension.

Endothelin is a polypeptide composed of 21 amino acids, and it is produced by vascular endothelial cells of human or pig. It is known that endothelin has a potent vasoconstrictor effect and a sustained and potent pressor action. It is also known that such a vasoconstriction is caused by binding of endothelin to its receptors on the vascular smooth muscles (Nature, 332, 411-415 (1988), FEBS Letters, 231, 440-444 (1988) and Biochem. Biophys. Res. Commun., 154, 868-875 (1988)).

As reported, the endothelin levels are clearly elevated in the blood of patients with essential hypertension or acute myocardial infarction, or in the washing fluids of the respiratory tract of patients with asthmaticus as compared with normal levels (Japan. J. Hypertension, 12, 79 (1989) and The Lancet, 23, 747-748 (1989)).

Further, an increased sensitivity of the cerebral blood vessel to endothelin in an experimental model of cerebral vasospasm (Japan. Soc. Cereb. Blood Flow & Metabol., 1, 73 (1989)) and an improved renal function by the endothelin antibody in an acute renal failure model have been reported (J. Clin. Invest., 83, 1762-1767 (1989)). Therefore, endothelin is assumed to be one of mediators causing acute renal failure or cerebral vasospasm following subarachnoid hemorrhage.

Further, endothelin is secreted not only by endothelial cells but also by tracheal epithelial cells or from kidney cells (FEBS Letters, 255 129-132 (1989), and FEBS Letters, 249, 42-46 (1989)).

Endothelin was also found to control the release of physiologically active substances such as renin, atrialnatriuretic peptide, endothelium-derived relaxing factor (EDRF), thromboxane $A_2$, prostacyclin, noradrenaline, angiotensin II and substance P (Biochem. Biophys. Res. Commun., 157, 1164-1168 (1988); Biochem. Biophys. Res. Commun., 155, 167-172 (1989); Proc. Natl. Acad. Sci. USA, 85, 9797-9800 (1989); J. Cardiovasc. Pharmacol., 13, S89-S92 (1989); Japan. J. Hypertension, 12, 76 (1989) and Neuroscience Letters, 102, 179-184 (1989)). Further, endothelin causes contraction of the smooth muscle of gastrointestinal tract and the uterine smooth muscle (FEBS Letters, 247, 337-340 (1989); Eur. J. Pharmacol., 154, 227-228 (1988); and Biochem. Biophys. Res. Commun., 159, 317-323 (1989)).

Further, endothelin was found to promote proliferation of rat vascular smooth muscle cells, suggesting a possible relevance to the arterial hypertrophy (Atherosclerosis, 78, 225-228 (1989)). Furthermore, since the endothelin receptors are present in a high concentration not only in the peripheral tissues but also in the central nervous system, and the cerebral administration of endothelin induces a behavioral change in animals, endothelin is likely to play an important role for controlling nerval functions (Neuroscience Letters, 97, 276-279 (1989)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is one of important mediators for endotoxin-induced diseases (Biochem. Biophys. Res. Commun., 161, 1220-1227 (1989); and Acta Physiol. Scand., 137, 317-318 (1989)).

Further, cyclosporin, when added to the renal cell culture (LLC-PK1 cells), remarkably increased endothelin secretion (Eur. J. Pharmacol., 180, 191-192 (1990)). Further, when cyclosporin was administered to rats, a decrease in the glomerular filtration rate and an increase in the blood pressure were observed, in association with a remarkable increase in the circulating endoehtlin level. This cyclosporin-induced renal failure can be suppressed by the administration of endothelin antibody (Kidney Int., 37, 1487-1491 (1990)). Thus, it is assumed that endothelin is significantly involved in the pathogenesis of the cyclosporin-induced diseases.

Accordingly, substances which specifically inhibit the binding of endothelin to its receptor are believed to antagonize the above-mentioned various physiological activities of endothelin and thereby being useful as a medicine in a wide range of fields. However, such an endothelin antagonist has never been discovered yet.

Endothelin is an endogenous substance which directly or indirectly (by controlling liberation of various endogenous substances) induces sustained contraction of vascular or non-vascular smooth muscles, and its excess production or excess secretion is believed to be one of pathogeneses for hypertension, bronchial asthma, acute renal failure, myocardinal infarction, angina pectoris, cerebral vasospasm and cerebral infarction. Further, it is suggested that endothelin serves as an important mediator involved in diseases such as endotoxin shock, endotoxin-induced multiple organ failure or disseminated intravascular coagulation, and/or cyclosporin-induced renal failure or hypertension. Accordingly, the objective of the present invention is to provide a novel therapeutics for the treatment of the above-mentioned various diseases by an invention of an endothelin antagonist.

In order to solve the above-mentioned problems, the present inventors have synthesized various cyclic pentapeptides and have investigated their endothelin antagonistic activities, and as a result have found that novel cyclic pentapeptides represented by the following formula (I) have strong endothelin antagonistic activities. The present invention has been accomplished on the basis of this discovery.

Thus, the present invention provides a cyclic pentapeptide of the formula:

$$\text{cyclo } (-X^1-X^2-X^3-X^4-X^5-) \qquad (I)$$

wherein $X^n$ (n=1-5) represent amino acid residues, respectively, and $X^1$ is DPhe, DTyr, DTha, DTza, DNal, DBta, DTrp, DTrp(O), DTrp(CHO) or DTrp((CH$_2$)$_m$COR$^1$) (wherein m is from 0 to 6, and $R^1$ is a hydroxyl group, a $C_1$-$C_6$ alkoxy group, an amino group or a $C_1$-$C_6$ monoalkylamino group, provided that when m=0, $R^1$ is not a hydroxyl group), $X^2$ is DAsp, DGlu or DCys($O_3$H), $X^3$ is Pro, Hyp, Pip, Thz, βAla, or Gly, Ala, αAba, Aib, Val, Nva, Leu, Ile, aIle, Nle, Met, Met(O), Met($O_2$), Phe, Tza, Tha, Tyr, Trp, His, Arg, Lys, Lys(CHO), Orn, Orn(CHO), Asn, Gln, Asp, Glu, Cys($O_3$H), Cys, Ser or Thr wherein a hydrogen atom on the α-amino group may be substituted by a $C_1$-$C_6$ alkyl or $C_3$-$C_7$ cycloalkyl group which may have an optional group selected from the group consisting of an imidazolyl group, a carboxyl group, a sulfo group and a hydroxyl group, $X^4$ is DAla, DThr, DαAba, DVal, DNva, DLeu, DIle, DaIle, DNle, DtertLeu, DCpg, DChg, DDpg, DPen, Aib, $Ac_3c$, $Ac_4c$, $Ac_5c$, $Ac_6c$, $Ac_7c$, or DPhg, DThg, DFug, DTzg or DItg wherein a hydrogen atom at the α-position may be substituted by a $C_1$-$C_3$ alkyl group, $X^5$ is Pro, Pip, Thz, or His, Ala, αAba, Val, Nva, Leu, Ile, aIle, Nle, Met, $C_3$al, $C_4$al, $C_5$al or $C_6$al wherein a hydrogen atom on the α-amino group may be substituted by a $C_1$-$C_6$ alkyl group; or a pharmaceutically acceptable salt thereof.

The present invention also provides a process for producing a cyclic pentapeptide of the above formula (I), which comprises cyclizing a linear pentapeptide of the formula (II) or its salt:

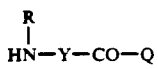

(II)

wherein Y is a divalent group capable of forming a linear pentapeptide residue having an amino acid sequence corresponding to the cyclic pentapeptide of the formula (I), together with a group of the formula —NR (wherein R is a hydrogen atom, a $C_1$-$C_6$ alkyl or $C_3$-$C_7$ cycloalkyl group which may have an optional group selected from the group consisting of an imidazolyl group, a carboxyl group, a sulfo group and a hydroxyl group, or a group forming Pro, Hyp, Pip or Thz at the N-terminal as bonded to a part of Y) and a group of the formula —CO, wherein sidechain functional groups of the amino acids may optionally be protected, and Q is a leaving group, to obtain a cyclic pentapeptide wherein sidechain functional groups of the amino acids may be protected, subjecting, if necessary, this cyclic pentapeptide to at least one reaction selected from the group consisting of 1) removal of the sidechain protective groups, 2) formylation, alkoxycarbonylation or alkoxycarbonylalkylation at the 1-position of the indole ring of tryptophan, 3) conversion of the alkoxycarbonyl group in the substituent at the 1-position of the indole ring of tryptophan to a carboxyl group or a carbamoyl group, 4) formylation of the sidechain amino group of lysine or ornithine, and 5) oxidation of methionine to methionine sulfoxide or methionine sulfone, and furthermore optionally conducting the conversion to a pharmaceutically acceptable salt.

Further, the present invention provides a drug for treating hypertension, acute renal failure, myocardial infarction, angina pectoris, cerebral infarction, cerebral vasospasm, asthma, endotoxin shock, endotoxin-induced multiple organ failure or disseminated intravascular coagulation, and/or cyclosporin-induced renal failure or hypertension, which contains a cyclic pentapeptide of the formula (I) or a pharmaceutically acceptable salt thereof.

DETAILED DESCRIPTION OF THE DRAWINGS

In the accompanying drawings:

FIG. 8 shows the activities of the compound of Example 15 (○) against the endotoxin-induced body temperature lowering effect as compared with the case where no drug was administered (●).

Figure 1:
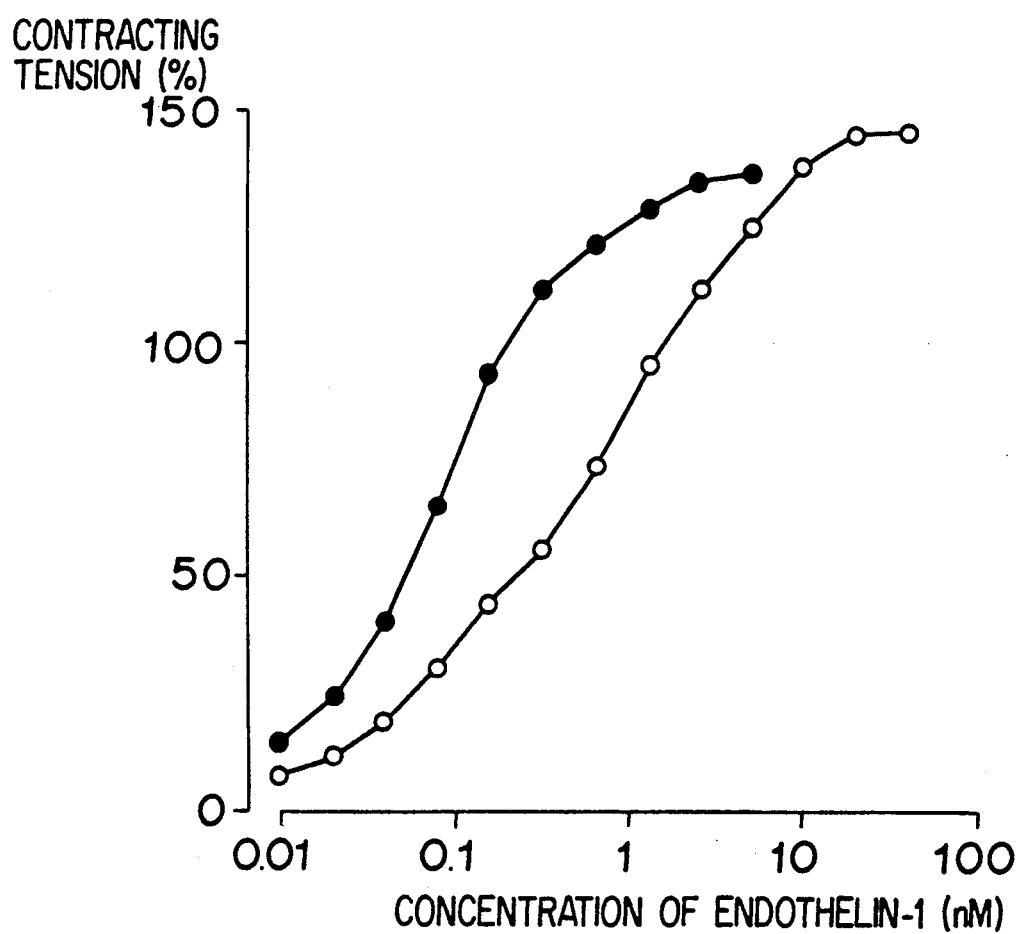
FIG. 1 shows the activities of the compound of Example 12 (○) against endothelin-induced contraction of isolated coronary artery as compared with the case in which no drug is present (●).

Now, the present invention will be described in further detail with reference to the preferred embodiments.

Now, the meanings of various abbreviations used in this specification will be given. The abbreviations relating to amino acids and their protective groups are in accordance with the recommendation by IUPAC-IUB Commission on Biochemical Nomenclature (Biochemistry, 11, 1726 (1972)) and common usage.

| | |
|---|---|
| αAba | L-α-aminobutanoic acid |
| DαAba | D-α-aminobutanoic acid |
| $Ac_3c$ | 1-aminocyclopropanecarboxylic acid |
| $Ac_4c$ | 1-aminocyclobutanecarboxylic acid |
| $Ac_5c$ | 1-aminocyclopentanecarboxylic acid |
| $Ac_6c$ | 1-aminocyclohexanecarboxylic acid |
| $Ac_7c$ | 1-aminocycloheptanecarboxylic acid |
| Aib | 2-amino-2-methylpropionic acid |
| Ala | L-alanine |
| DAla | D-alanine |
| βAla | β-alanine |
| Arg | L-arginine |
| Asn | L-asparagine |
| Asp | L-aspartic acid |
| DAsp | D-aspartic acid |
| DAsp(ONa) | sodium D-aspartate |
| DBta | D-3-(3-benzo[b]thienyl)alanine |
| $C_3$al | L-3-cyclopropylalanine |
| $C_4$al | L-3-cyclobutylalanine |
| $C_5$al | L-3-cyclopentylalanine |
| $C_6$al | L-3-cyclohexylalanine |
| DChg | D-2-cyclohexylglycine |
| CmGly | N-(carboxymethyl)glycine |
| DCpg | D-2-cyclopentylglycine |
| CpGly | N-cyclopentylglycine |
| Cys | L-cysteine |

| | -continued |
|---|---|
| Cys(O₃H) | L-cysteic acid |
| Cys(O₃Na) | sodium L-cysteate |
| DCys(O₃H) | D-cysteic acid |
| DCys(O₃Na) | sodium D-cysteate |
| DCys(O₃Bu₄N) | tetrabutylammonium D-cysteate |
| DDpg | D-2-(1,4-cyclohexadienyl)glycine |
| DEtg | (2S)-2-ethyl-2-(2-thienyl)glycine |
| DFug | D-2-(2-furyl)glycine |
| Glu | L-glutamic acid |
| DGlu | D-glutamic acid |
| Gln | L-glutamine |
| Gly | glycine |
| His | L-histidine |
| Hyp | 4-hydroxy-L-proline |
| IeGly | N-[2-(4-imidazolyl)ethyl]glycine |
| Ile | L-isoleucine |
| aIle | L-alloisoleucine |
| DIle | D-isoleucine |
| DaIle | D-alloisoleucine |
| DItg | D-2-(isothiazolyl)glycine |
| Leu | L-leucine |
| DLeu | D-leucine |
| DtertLeu | D-2-amino-3,3-dimethylbutanoic acid |
| Lys | L-lysine |
| Lys(CHO) | N⁶-formyl-L-lysine |
| MeAla | N-methyl-L-alanine |
| MeLeu | N-methyl-L-leucine |
| MeMet | N-methyl-L-methionine |
| Met | L-methionine |
| Met(O) | L-methionine sulfoxide |
| Met(O₂) | L-methionine sulfone |
| DNal | D-3-(1-naphthyl)alanine |
| Nle | L-norleucine |
| DNle | D-norleucine |
| Nva | L-norvaline |
| DNva | D-norvaline |
| Orn | L-ornithine |
| Orn(CHO) | N⁵-formyl-L-ornithine |
| DPen | D-penicillamine |
| Phe | L-phenylalanine |
| DPhe | D-phenylalanine |
| DPhg | D-phenylglycine |
| Pip | L-pipecolinic acid |
| iPrGly | N-isopropylglycine |
| Pro | L-proline |
| Sar | sarcosine |
| Ser | L-serine |
| Tha | L-3-(2-thienyl)alanine |
| DTha | D-3-(2-thienyl)alanine |
| DThg | D-2-(2-thienyl)glycine |
| Thr | L-threonine |
| DThr | D-threonine |
| Thz | L-thiazolidine-4-carboxylic acid |
| Trp | L-tryptophan |
| DTrp | D-tryptophan |
| DTrp(CHO) | N^in-formyl-D-tryptophan |
| DTrp(O) | D-3-(2,3-dihydro-2-oxoindol 3-yl)alanine |
| DTrp((CH₂)ₘCOR¹) | D-tryptophan substituted by a —(CH₂)ₘCOR¹ group at the 1-position of the indole ring |
| Tyr | L-tyrosine |
| DTyr | D-tyrosine |
| Tza | L-3-(2-thiazolyl)alanine |
| DTza | D-3-(2-thiazolyl)alanine |
| DTzg | D-2-(thiazolyl)glycine |
| Val | L-valine |
| DVal | D-valine |
| Boc | tert-butoxycarbonyl |
| Z | benzyloxycarbonyl |
| Fmoc | 9-fluorenylmethoxycarbonyl |
| ᵗBu | tert-butyl |
| Bzl | benzyl |
| Pac | phenacyl |
| Pfp | pentafluorophenyl |
| HOBT.H₂O | 1-hydroxy-1H-benzotriazol monohydrate |
| DCC | N,N'-dicyclohexylcarbodiimide |
| DIPC | N,N'-diisopropylcarbodiimide |
| EDCI.HCl | 1-ethyl-3-(3-dimethylaminopropyl)-carbodiimide hydrochloride |
| TFA | trifluoroacetic acid |

| | -continued |
|---|---|
| TEA | triethylamine |
| EDT | 1,2-ethanedithiol |
| p-TosOH | p-toluenesulfonic acid |
| Pd/C | palladium-carbon |
| DMAP | 4-dimethylaminopyridine |
| DMF | N,N-dimethylformamide |
| THF | tetrahydrofuran |
| DMSO | dimethylsulfoxide |
| MOPS | 3-morphorinopropanesulfonic acid |
| HEPES | 2-[4-(2-hydroxyethyl)-1-piperadinyl]ethanesulfonic acid |
| Tris | tris(hydroxymethyl)aminomethane |
| PMSF | phenylmethanesulfonyl fluoride |

Now, the process for producing the novel cyclic pentapeptide of the present invention will be described.

The cyclic pentapeptide of the present invention is prepared by cyclizing the corresponding linear pentapeptide wherein the sidechain functional groups of the amino acids may be protected as the case requires, and then, if necessary, conducting at least one reaction selected from the group consisting of 1) removal of the sidechain protective groups, 2) formylation, alkoxycarbonylation or alkoxycarbonylalkylation of the 1-position of the indole ring of tryptophan, 3) conversion of the alkoxycarbonyl group in the substituent at the 1-position of the indole ring of tryptophan to a carboxyl group or a carbamoyl group, 4) formylation of the sidechain amino group of lysine or ornithine, and 5) oxidation of methionine to methionine sulfoxide or methionine sulfone, and further converting the product to a pharmaceutically acceptable salt, if necessary.

The linear pentapeptide can be prepared by a method wherein an amino acid is condensed one by one, by a method wherein condensation products of plural amino acids are condensed with each other, or by a combination of such methods. Such condensation can be conducted in a liquid phase or in a solid phase by known methods such as an azide method, a mixed acid anhydride method, a DCC method and an active ester method (disclosed, for example, by M. Bodansky and M. A. Ondetti in Peptide Synthesis, Interscience, New York, 1966; by F. M. Finn and K. Hofmann in The Proteins, Vol. 2, ed. by H. Nenrath and R. L. Hill, Academic Press Inc., New York, 1976; by Nobuo Izumiya et al. in Peptide Synthesis, Maruzen, 1975).

The preparation of the compound of the present invention by a solid phase method can be conducted in the following manner. The linear pentapeptide can be obtained by successive condensations on an insoluble carrier such as a chloromethyl resin (Biochemistry, 3, 1385 (1964)), an oxymethyl resin (Chem. Ind. (London), 1966, 1597), a p-alkoxybenzyl alcohol resin (J. Am. Chem. Soc., 95, 1328 (1973)) or a functionalized polyamide resin (Bioorganic Chemistry, 8, 351–370 (1979)). Firstly, an α-amino group of the amino acid selected for the C-terminus in the linear pentapeptide, is protected. If a reactive functional group is present in the sidechain, such a sidechain functional group is also protected. Then, it is bonded as a carboxylic acid ester to the insoluble carrier in accordance with a known method. Then, the α-amino protective group is removed, and then the next amino acid derivative (the α-amino group and, if necessary, the sidechain functional group are protected) is condensed by simultaneously adding a condensing reagent such as DCC or DIPC, if necessary together with an additive such as HOBT.H₂O. This amino acid derivative may be used as a carboxyl-activated amino acid such as a pentafluorophenyl ester or an acid azide. Such deprotection and condensation are repeated to afford a desired linear pentapeptide. The protective group of an amino group is selected usually from those well known in the art, for example from urethane type protective groups such as a Z group, a Boc group, a Fmoc group, a p-methoxybenzyloxycarbonyl group and a p-nitrobenzyloxycarbonyl group. For the protection of an α-amino group, it is preferred to use a Fmoc group or a Boc group. The Fmoc group can be readily deprotected after the condensation with relatively mild base such as a 20% solution of piperidine in DMF. On the other hand, the Boc group can be readily deprotected with relatively mild acid such as TFA. When the Fmoc group is used for the protection of an α-amino group, the sidechain carboxyl group of e.g. aspartic acid or glutamic acid may be protected as a tert-butyl ester or a trityl ester, the hydroxyl group of e.g. tyrosine, serine or threonine may be protected as a tert-butyl ether, the sidechain amino group of e.g. lysine or ornithine and the imidazolyl group of histidine may be protected by a Boc group, the mercapto group of cysteine may be protected by a trityl group, and the guanidino group of arginine may be protected by a pentamethylchromansulfonyl group, so that these protective groups are stable under the conditions for the removal of the Fmoc group, and after the cyclization of the linear pentapeptide, all such protective groups can be simultaneously deprotected with mild acid such as TFA. On the other hand, when the Boc group is used for the protection of the α-amino group, the sidechain carboxyl group of e.g. aspartic acid or glutamic acid may be protected as a benzyl ester, the hydroxyl group of e.g. tyrosine, serine or threonine may be protected as a benzyl ether, and the sidechain amino group of e.g. lysine or ornithine and the imidazolyl group of histidine may be protected by a Z group, so that these protective groups are stable under the conditions for removing the Boc group, and after the cyclization of the linear pentapeptide, all such protective groups can be simultaneously removed by, for example, catalytic hydrogenation, treatment with hydrogen fluoride or treatment with trimethylsilyl trifluoromethanesulfonatethioanisole-TFA (Chem. Pharm. Bull., 35, 3447–52 (1987)).

Cleavage of the linear pentapeptide from the resin after the removal of the N-terminal protective group, can be conducted by various methods well known to those skilled in the art. For example, cleavage of the peptide from the resin with hydrazine affords the corresponding hydrazide. The hydrazide can be cyclized via an azide to afford the desired cyclic pentapeptide. The hydrazide is converted to the corresponding azide by treatment with a reagent which supplies nitrous acid in site. As a reagent suitable for this purpose, there may be mentioned a lower alkyl ester of nitrous acid (such as tert-butyl nitrite or isoamyl nitrite) or an alkali metal salt of nitrous acid (such as sodium nitrite or potassium nitrite) in the presence of strong acid such as hydrochloric acid or sulfuric acid. This reaction can be conducted at ca. −40° C. to 20° C. in water and/or non-aqueous solvent such as DMF, THF or 1,4-dioxane. On the other hand, when a solid phase synthesis is conducted by use of a p-alkoxybenzyl alcohol resin as an insoluble carrier, it is possible to obtain a linear peptide having a carboxyl group as the C-terminus (the sidechain functional groups may be protected as the case requires) by cleavege the peptide with mild acid such as TFA. Such a linear pentapeptide can be cyclized into a cyclic pentapeptide by treatment with a condensing reagent such as DCC (or EDCI HCl)-HOBT.H2O or diphenylphosphoryl azide in DMF, THF, 1,4-dioxane, acetonitrile, dichloromethane or chloroform at ca. −40° C. to 20° C. Such cyclization is conducted preferably under high dilution conditions, since the intermolecular reaction is likely to take place in competition with the intramolecular reaction. When the cyclic pentapeptide thus obtained has protective groups in its sidechains, the protective groups can be removed by suitable methods. The cyclic pentapeptide thus obtained may be led to a salt of alkali metal or alkaline earth metal such as sodium, potassium or calcium, an addition salt with basic amino acid such as lysine or arginine, an acid addition salt with mineral acid such as hydrochloric acid or sulfuric acid, an acid addition salt with acidic amino acid such as aspartic acid or glutamic acid, or an acid addition salt with organic acid such as maleic acid, fumaric acid, tartaric acid, malic acid or citric acid.

On the other hand, the linear pentapeptide may be also prepared in a liquid phase by known methods wherein an amino acid is condensed one by one, by a method wherein condensation products of plural amino acids are condensed with each other, or by a combination of such methods.

The protective groups for the N-terminal α-amino group, the C-terminal α-carboxyl group and the reactive functional groups of the sidechains of the linear pentapeptide should be selected according to the cyclization method of the linear pentapeptide.

For example, in the case of an azide method wherein the linear pentapeptide is led to a hydrazide and then cyclized via an azide, it is preferred to protect the N-terminal α-amino group with a Z group, the C-terminal α-carboxyl group as an ester such as a methyl ester, an ethyl ester or a benzyl ester and the sidechain reactive functional groups such as the carboxyl group of e.g. aspartic acid or gultamic acid as a tert-butyl ester or a trityl ester, the hydroxyl group of e.g. tyrosine, serine or threonine as a tert-butyl ether, the amino group of e.g. lysine or ornithine with a Boc group, the imidazolyl group of histidine or the mercapto group of cysteine with a trityl group, and the guanidino group of arginine with a pentamethylchromansulfonyl group. Namely, the full-protected linear pentapeptide obtained after the peptide-condensation is allowed to react with hydrazine to afford the corresponding hydrazide, whose N-terminal Z group is successively removed by catalytic hydrogenation. Under these reaction conditions are intact the protective groups of the sidechain functional groups. Then, after the cyclization reaction, all such sidechain protective groups can be deprotected with mild acid such as TFA. In the case where the peptide has no reactive functional groups at its sidechains, it is also possible to select a Boc group as the protective group for the N-terminal α-amino group in the azide method.

The N-terminal deprotected linear pentapeptide hydrazide obtained by the liquid phase method may be subjected to cyclization via an azide in the same manner as the hydrazide obtained by the solid phase method, to afford a cyclic pentapeptide.

In the case where after the removal of the protective group for the N-terminal α-amino group and the C-terminal α-carboxyl group, the linear pentapeptide is cyclized by treatment with condensing reagents such as DCC (or EDCI.HCl)-HOBT.H2O or diphenylphosphorylazide, it is preferred to protect the N-terminal α-amino group with a o Boc group, the C-terminal α-carboxyl group as a tert-butyl ester or a phenacyl ester, and the sidechain reactive functional groups such as the carboxyl group of e.g. aspartic acid or gultamic acid as a benzyl ester, the hydroxyl group of e.g. tyrosine, serine or threonine as a benzyl ether, and the amino group of e.g. lysine or ornithine, the imidazolyl group of histidine and the indolyl group of tryptophan with a Z group. Namely, in the case where the C-terminus of the protected linear pentapeptide obtained after the condensation is a tert-butyl ester, the Boc group of the N-terminus and the tert-butyl ester of the C-terminus can be simultaneously removed without removing the sidechain protective groups, by use of mild acid such as TFA. In the case where the C-terminus is a phenacyl ester, the Boc group of the N-terminus can be removed by use of mild acid such as TFA and the phenacyl ester of the C-terminus can be removed by use of zinc/acetic acid, without removing the sidechain protective groups. In each case, all such sidechain protective groups can be removed after cyclization by a method such as catalytic hydrogenation. Further, in the case where the N-terminal α-amino group is protected by a Z group and the C-terminal α-carboxyl group is protected as a benzyl ester or a phenacyl ester, the sidechain reactive functional groups may be protected in such manner that the carboxyl group of e.g. aspartic acid or glutamic acid be protected as a tert-butyl ester or a trityl ester, the hydroxyl group of e.g. tyrosine, serine or threonine be protected as a tert-butyl ether, and the amino group of e.g. lysine or ornithine and the imidazolyl group of histidine be protected with a Boc group, so that these sidechain protective groups will not be removed under the conditions for the removal of the protective groups for the N-terminal α-amino group and the C-terminal α-carboxyl group. After the cyclization, all such sidechain protective groups can be removed by use of mild acid such as TFA.

The linear pentapeptide thus obtained can be subjected to cyclization by treatment with condensing reagents in the same manner as the linear pentapeptide obtained by the solid phase method, to afford a cyclic pentapeptide. Otherwise, such a linear pentapeptide may be led to an active ester such as a p-nitrophenyl ester or an N-hydroxysuccinimide ester with the protected N-terminal α-amino group, and then the resulting active ester can be cyclized by the deprotection of the N-terminal α-amino group.

If necessary, the cyclic pentapeptide whose sidechain functional groups may be protected, or a salt thereof, may be further subjected to formylation, alkoxycarbonylation or alkoxycarbonylalkylation of the 1-position of the indole ring of tryptophan, conversion of the alkoxycarbonyl group in the substituent at the 1-position of the indole ring of tryptophan to a carboxyl group or a carbamoyl group, formylation of the sidechain amino group of lysine or ornithine, or oxidation of methionine to methionine sulfoxide or methionine sulfone.

The formylation of the 1-position of the indole ring of tryptophan can be performed, for example, by treating a cyclic pentapeptide containing tryptophan with formic acid saturated by hydrogen chloride at −20° C. to room temperature. The alkoxycarbonylation or the alkoxycarbonylalkylation at the 1-position of the indole ring can be conducted by treating the cyclic peptide with the corresponding acid halide, acid anhydride or alkyl halide by using phase transfer catalysts as described in the literature (Synthesis, 387 (1979)) or using DMAP as catalysts (J. Chem. Soc., Chem. Commun., 1699 (1984)). The conversion of the alkoxycarbonyl group in the substituent at the 1-position of the indole ring of tryptophan to a carboxyl group can be conducted by usual alkali or acid hydrolysis, and the conversion to a carbamoyl group can be conducted by amidation with the corresponding amine. Further, formylation of the sidechain amino group of lysine or ornithine can be conducted, for example, by treating a cyclic pentapeptide containing lysine or ornithine with 1 to 10 equivalents of formic pivalic anhydride at 0° C. to room temperature in solvent such as DMF or acetonitrile. On the other hand, the conversion of methionine to methionine sulfoxide or methionine sulfone can be conducted, for example, by treating a cyclic pentapeptide containing methionine (provided that when amino acid residues having sidechain functional groups susceptible to oxidation other than the methionine are contained, such sidechain functional groups are preferably protected by suitable protective groups) with hydrogen peroxide or peroxy acid such as peracetic acid at 0° C. to 80° C. in solvent such as acetic acid. By properly controlling the amount of oxidizing reagent, the reaction temperature and the reaction time, it is possible to obtain selectively either methionine sulfoxide or methionine sulfone. Further, methionine sulfone can be obtained by further treating methionine sulfoxide under the above-mentioned reaction conditions.

The cyclic pentapeptide thus obtained may be subjected, if necessary, to removal of protective groups, and may be subjected to formation of a salt or exchange of a salt, as the case requires, to afford a desired cyclic pentapeptide of the present invention or a pharmaceutically acceptable salt thereof.

Now, the endothelin antagonistic properties of the cyclic pentapeptides of the present invention will be described.

Endothelin binding inhibition test

The smooth muscle tissue of porcine aorta was homogenized in a buffer solution of 10 mM MOPS, pH 7.4, at 4° C. by a polytron. To the homogenate, sucrose was added to a concentration of 20%, and the mixture was centrifuged at 1,000×g for 15 minutes, and the supernatant was further centrifuged at 10,000×g for 15 minutes. The supernatant thereof was further centrifuged at 90,000×g for 40 minutes. The membrane precipitate thereby obtained was suspended in a buffer solution of 5 mM HEPES/Tris, pH 7.4, at a concentration of 25 mg/ml.

Then, 16 μl of this membrane suspension was added to 340 μl of 50 mM Tris/HCl buffer, pH 7.4, containing 10 μM calcium chloride, 10 μM magnesium chloride, 0.1 mM PMSF, 1 μM pepstatin A, 2 μM leupeptin, 1 mM 1,10-phenanthroline and 0.1% bovine serum albumin. To this suspension, 4 μl of (A) endothelin-1 (for nonspecific binding: 0.2 μM as the final concentration), (B) buffer solution A (for total control binding), or (C) a test compound (1.1 μM as the final concentration), was added. Further, to each suspension, 40 μl of $^{125}$I-endothelin-1 (12000–18000 cpm) was added. These mixtures were incubated at 25° C for 4 hours, then subjected to filtration on a glass filter GF/C and then washed with 5 mM HEPES/Tris, pH 7.4, containing 0.3% bovine serum albumin. Then, the radioactivity trapped by the glass filter was measured, and the $^{125}$I-endothelin-1 binding inhibition D (%) at 1.1 μM of the test compound was determined by the following equation.

$$D(\%) = 100 - \frac{(C) - (A)}{(B) - (A)} \times 100$$

Each test was performed in triplicate.

As shown in Table 1, the compounds of the present invention were found to be very potent inhibitor of endothelin binding. The test compounds are indicated by Example Nos.

TABLE 1

$^{125}$I-endothelin-1 binding inhibition by 1.1 μM of the test compounds

| Example No. | Inhibition (%) | Example No. | Inhibition (%) |
|---|---|---|---|
| 1 | 19 | 24 | 78 |
| 2 | 78 | 25 | 74 |
| 3 | 85 | 26 | 75 |
| 4 | 74 | 27 | 66 |
| 5 | 81 | 28 | 51 |
| 6 | 72 | 29 | 15 |
| 7 | 27 | 30 | 72 |
| 8 | 37 | 31 | 80 |
| 9 | 30 | 32 | 87 |
| 10 | 54 | 33 | 77 |
| 11 | 74 | 34 | 83 |
| 12 | 75 | 35 | 79 |
| 13 | 85 | 36 | 67 |
| 14 | 75 | 37 | 38 |
| 15 | 85 | 38 | 21 |
| 16 | 77 | 39 | 18 |
| 17 | 75 | 40 | 66 |
| 18 | 69 | 41 | 83 |
| 19 | 70 | 42 | 79 |
| 20 | 65 | 43 | 85 |
| 21 | 73 | 44 | 56 |
| 22 | 75 | 45 | 85 |
| 23 | 72 | 46 | 75 |
| 47 | 89 | 71 | 80 |
| 48 | 71 | 72 | 79 |
| 49 | 67 | 73 | 85 |
| 50 | 57 | 74 | 89 |
| 51 | 84 | 75 | 87 |
| 52 | 64 | 76 | 84 |
| 53 | 89 | 77 | 78 |
| 54 | 65 | 78 | 85 |
| 55 | 81 | 79 | 88 |
| 56 | 84 | 80 | 83 |
| 57 | 65 | 81 | 86 |
| 58 | 84 | 82 | 81 |
| 60 | 79 | 83 | 82 |
| 61 | 66 | 84 | 43 |
| 62 | 60 | 85 | 82 |
| 63 | 84 | 86 | 90 |
| 64 | 83 | 87 | 34 |
| 65 | 85 | 88 | 78 |
| 66 | 38 | 89 | 67 |
| 67 | 82 | 90 | 35 |
| 68 | 86 | 91 | 23 |
| 69 | 85 | 92 | 28 |
| 70 | 85 | | |

Activities against endothelin-induced contraction of isolated procine coronary arteries The coronary artery of pig was extracted, and a spiral preparation having a width of 1 mm and a length of 10 mm was prepared therefrom. The preparation having the endothelial cells denuded, was hanged in a 5 ml organ bath filled wit a Krebs.Henseleit solution saturated with a gas mixture of 95% $O_2$ and 5% $CO_2$, and the change in the tension was isometrically measured and recorded.

Endothelin-1 was added into the organ bath in a cumulatively increasing manner, whereby the influence of the compound of the present invention to the concentration-response curve for endothelin-1 was examined. The compound of the present invention was added into the organ bath 20 minutes prior to the addition of endothelin-1.

Figure 2:
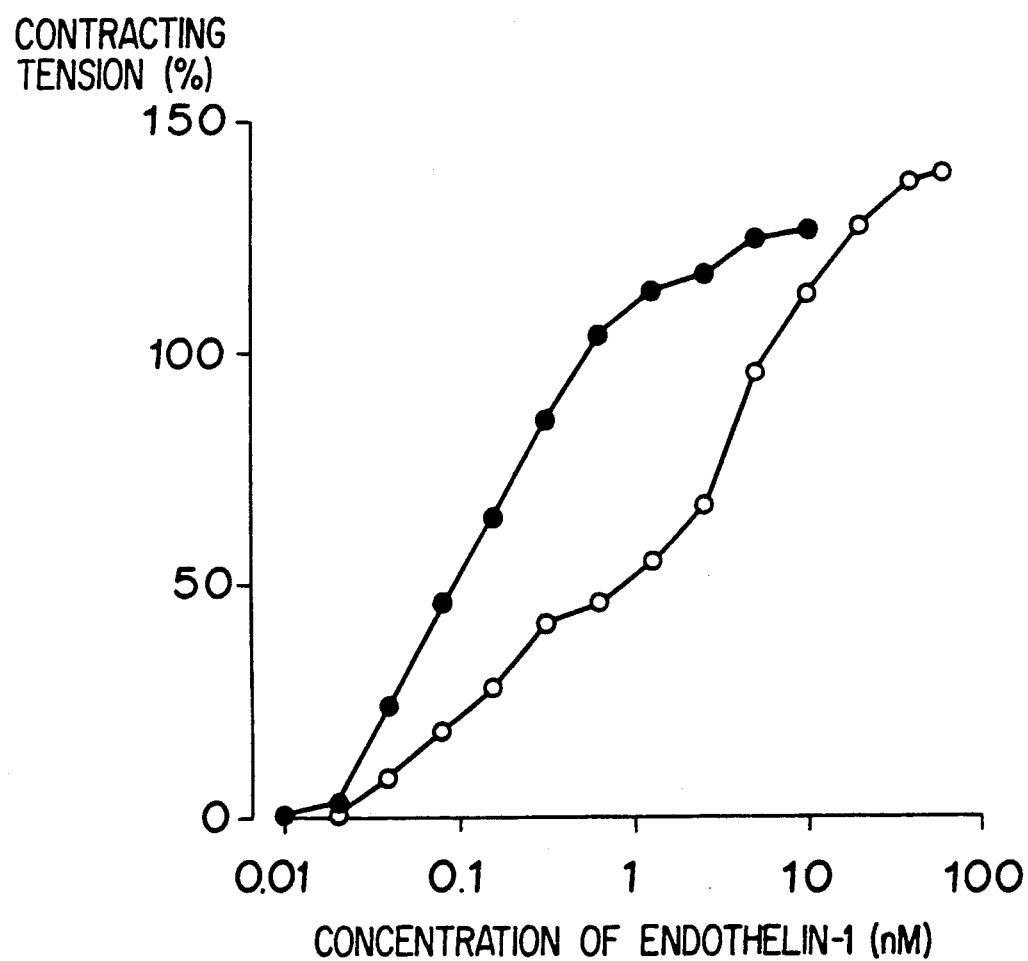
FIG. 2 shows the activities of the compound of Example 15 (○) against endothelin-induced contraction of isolated porcine coronary artery as compared with the case where no drug is present (●).
Figure 3:
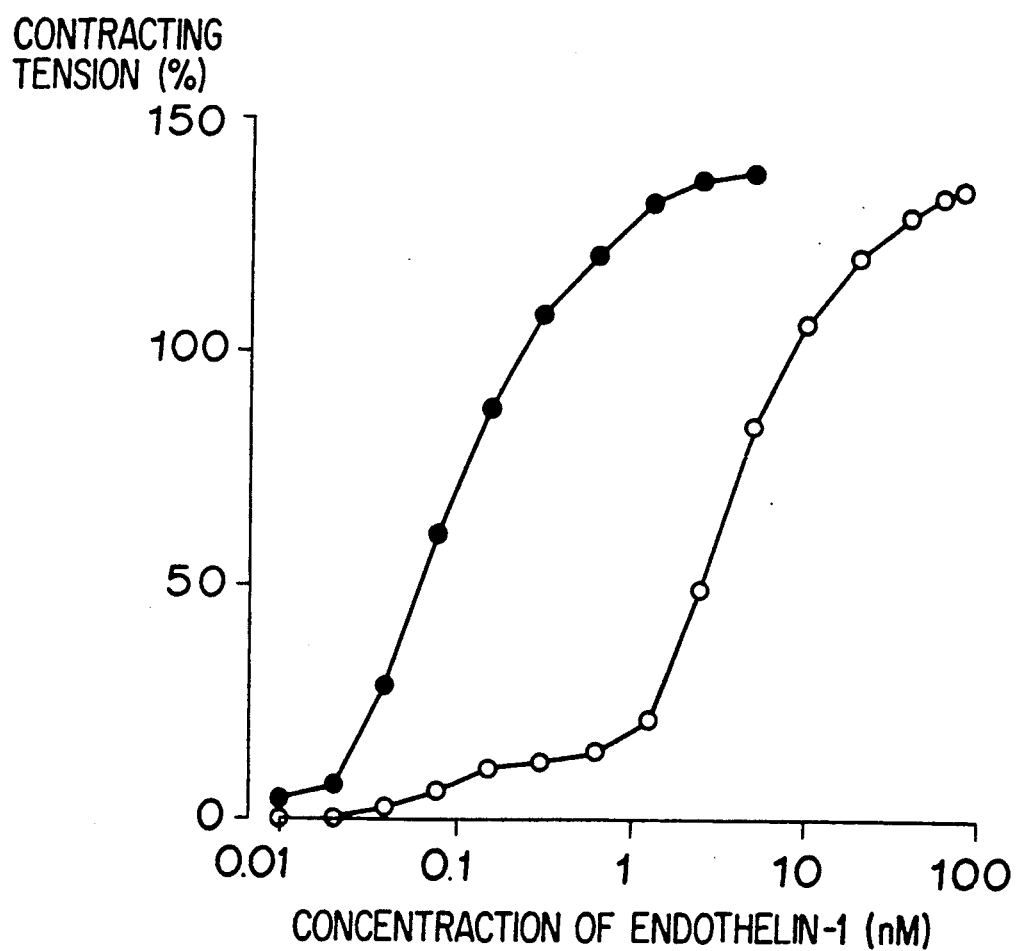
FIG. 3 shows the activities of the compound of Example 3 (○) against endothelin-induced contraction of isolated porcine coronary artery as compared with the case where no drug is present (●).

As shown in FIGS. 1 to 3, the compound of Example 12 (3 μM) (FIG. 1), the compound of Example 15 (2 μM) (FIG. 2) and the compound of Example 3 (2 μM) (FIG. 3) remarkably shifted the concentration-response curves of endothelin-1 to the right and did not affect the maximum response. Further, the compounds of the present invention showed no activities to the isolated coronary artery when applied alone. As is evident from the above, the compounds of the present invention showed remarkable antagonistic activities against endothelin-induced contraction of isolated porcine coronary artery.

Activities aqainst endothelin-induced contraction of isolated guinea pig trachea The trachea of a guinea pig was extracted, and the trachea was cut into rings to afford the preparation. A preparation having the endothelial cells denuded, was hanged in a 5 ml organ bath filled with a Krebs.Henseleit solution saturated with a gas mixture of 95% $O_2$ and 5% $CO_2$, and the change in the tension was isometrically measured and recorded.

Endothelin-1 was added into the organ bath in a cumulatively increasing manner, and the influence of the compound of the present invention to the concentration-response curve for endothelin was examined. The compound of the present invention was added into the organ bath 20 minutes prior to the addition of endothelin-1.

Figure 4:
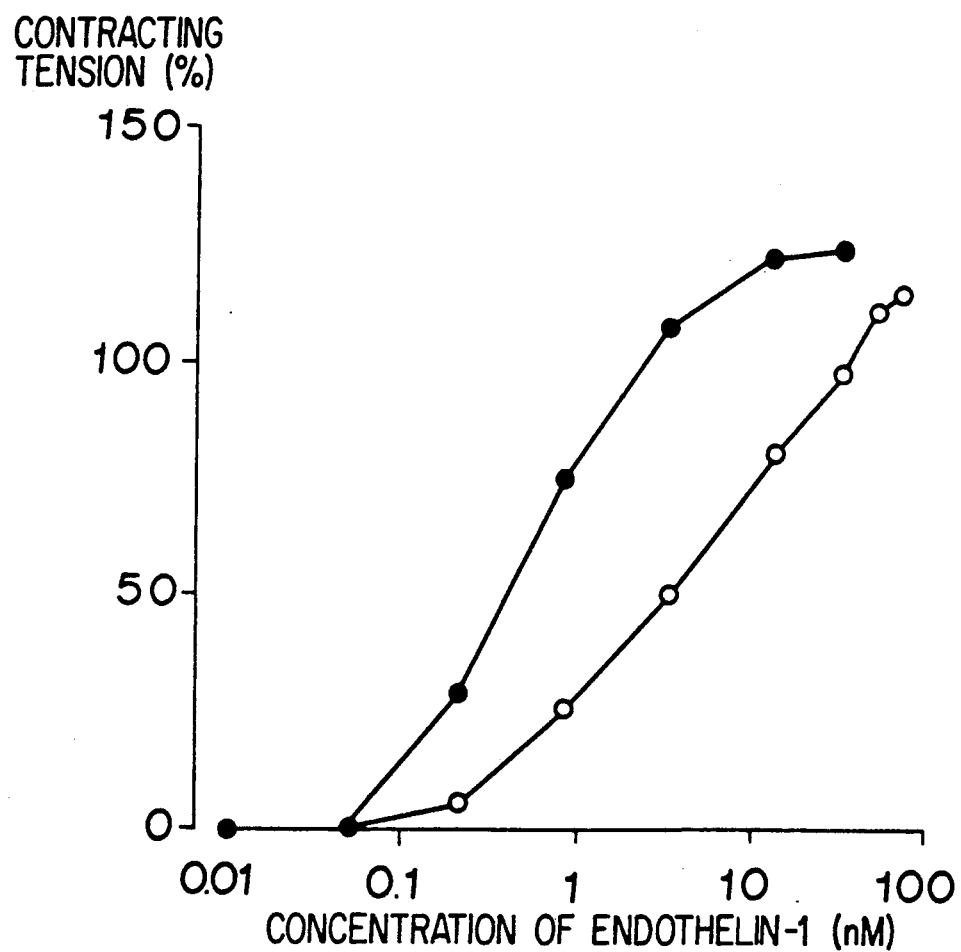
FIG. 4 shows the activities of the compound of Example 15 (○) against endothelin-induced contraction of isolated guinea pig trachea as compared with the case where no drug is present (●).
Figure 5:
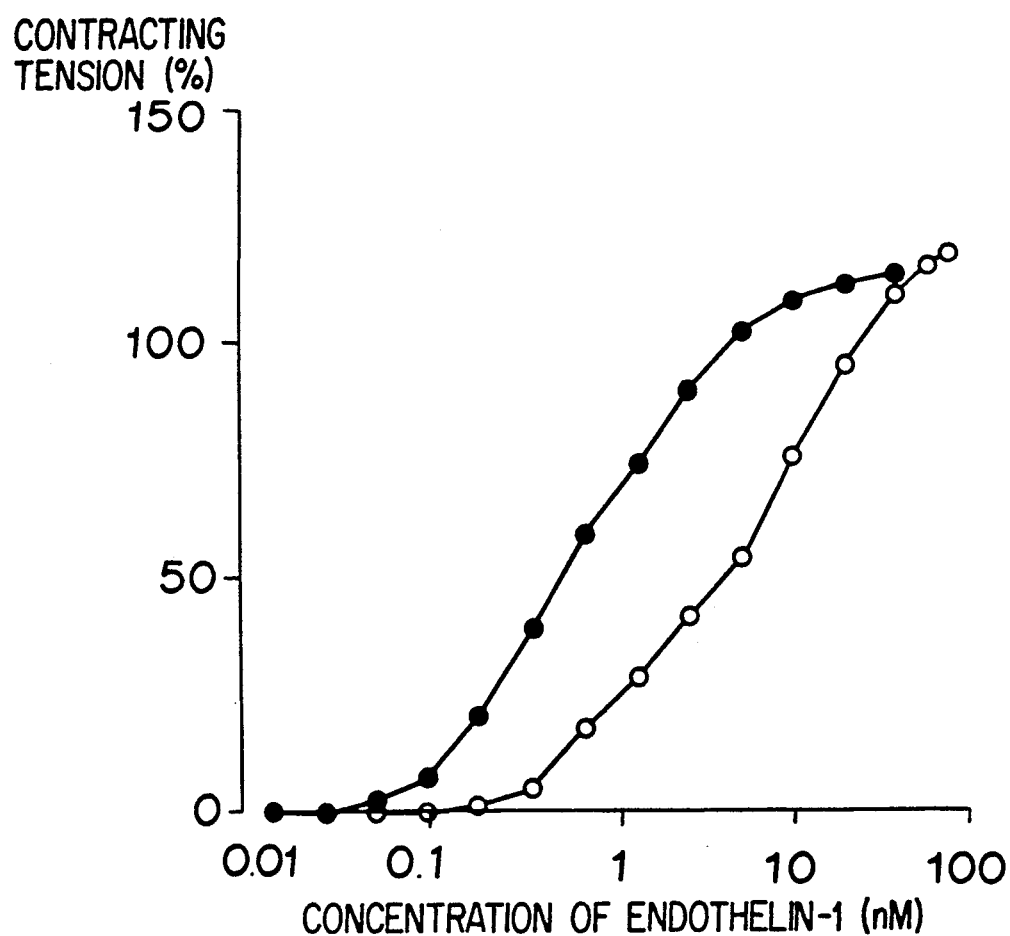
FIG. 5 shows the activities of the compound of Example 3 (○) against endothelin-induced contraction of isolated guinea pig trachea as compared with the case where no drug was present (●).

As shown in FIGS. 4 and 5, the compound of Example 15 (2 μM) (FIG. 4) and the compound of Example 3 (6 μM) (FIG. 5) remarkably shifted the concentration-response curves for endothelin-1 to the right in isolated trachea and did not affect the maximum response. Further, the compounds of the present invention showed no activities to the isolated trachea when applied alone. As is evident from the foregoing, the compounds of the present invention showed remarkable antagonistic activities against endothelin-induced contraction of isolated guinea big trachea.

Effects on the increased perfusion pressure induced by endothelin in isolated rat heart The heart of a male Sprague Dohrie (SD) rat was extracted, and the perfusion pressure was measured and recorded by a Langendorff's method. The perfusion pressure was evaluated on the basis that the state where a Krebs.Henseleit solution saturated with a gas mixture of 95% $O_2$ and 5% $CO_2$ was infused at a rate of 10 ml/min, was taken as a standard.

Endothelin-1 was cumulatively added to the perfusate, whereby the influence of the compound to the concentration-response curve for endothelin-1 was examined. The compound of the present invention which was dissolved in the perfusate had been infused from 20 minutes prior to the addition of endothelin-1 till just after finishing measurement of the concentration-response curve for endothelin-1.

Figure 6:
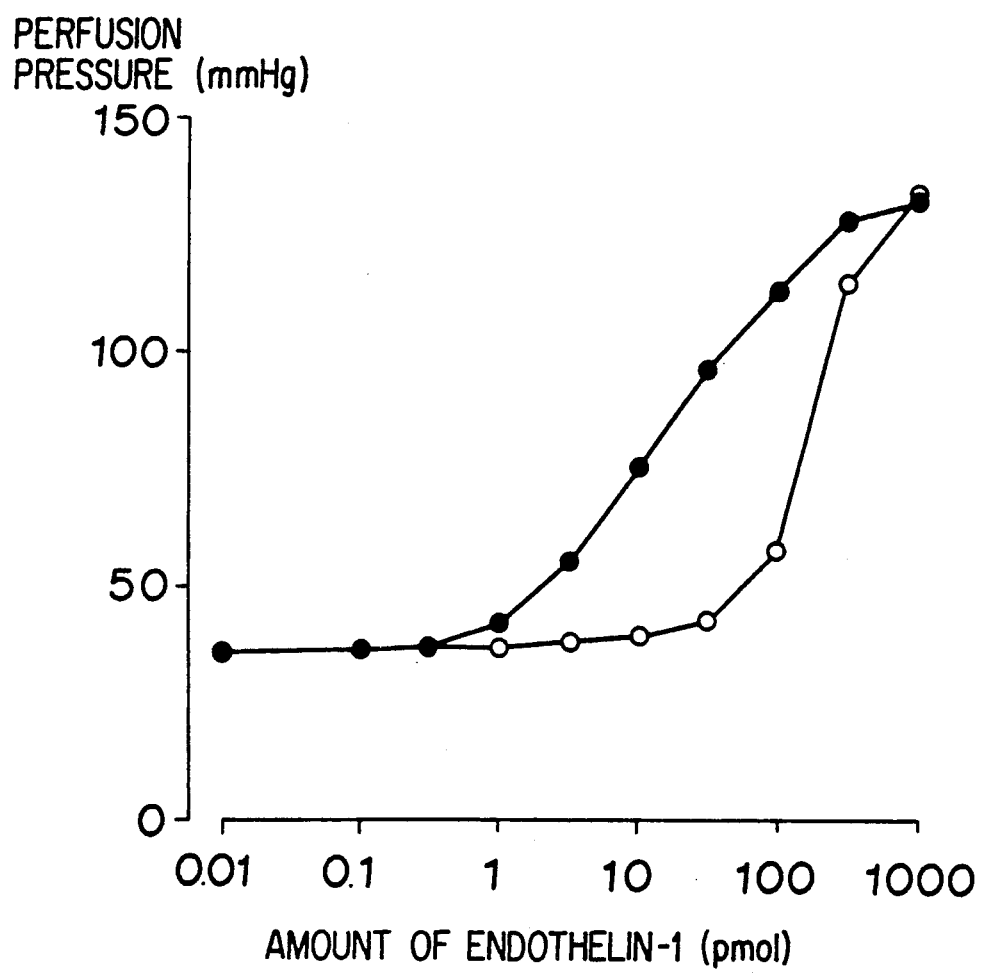
FIG. 6 shows the effects of the compound of Example 3 (○) against the increased perfusion pressure induced by endothelin in isolated rat heart as compared with the case where no drug was present (●).

As shown in FIG. 6, the compound of Example 3 (1 μM) moved the concentration-response curve for endothelin-1 to the right and did not affect the maximum response. Further, the compound of the present invention did not affect the perfusion pressure when applied alone. As is evident from the foregoing, the compound of the present invention showed remarkable antagonistic activities against the increased perfusion pressure induced by endothelin.

Activities against endothelin-induced contraction of isolated porcine basilar artery The arteria basilaris of pig was extracted, and then a ring preparation with a width of 4 mm was prepared. After denuded the endothelial cells, the preparation was hanged in a 5 ml organ bath filled with a Krebs.Henseleit solution saturated with a gas mixture of 95% $O_2$ and 5% $CO_2$, and the change in the tension was isometrically measured and recorded.

Endothelin-1 was added into the organ bath in a cumulatively increasing manner, whereby the influence of the compound of the present invention to the concentration-response curve for endothelin-1 was examined. The compound of the present invention was added into the organ bath 20 minutes prior to the addition of endothelin-1.

Figure 7:
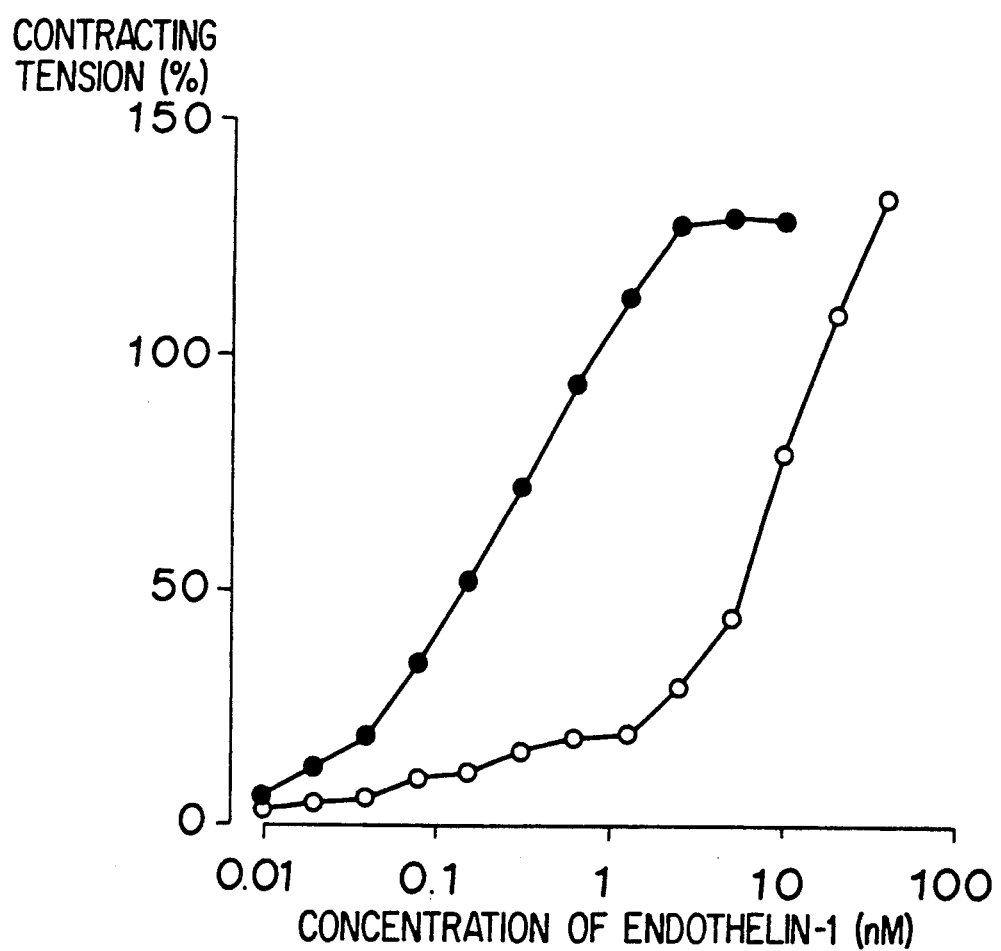
FIG. 7 shows the activities of the compound of Example 3 (○) against endothelin-induced contraction of isolated porcine basilar artery as compared with the case where no drug was present (●).

As shown in FIG. 7, the compound of Example 3 (2 $\mu$M) remarkably shifted the concentration-response curve for endothelin-1 to the right and did not affect the maximum response. Further, the compound of the present invention showed no activities to the isolated basilar artery when applied alone. As is evident from the foregoing, the compound of the present invention exhibited remarkable antagonistic activities against endothelin-induced contraction of isolated porcine basilar artery.

Activities against an endotoxin shock

To a male ddy mouse, endotoxin (Lipopolysaccharide derived from *E. coli* 055:B5) dissolved in a 0.15% sodium hydrogencarbonate aqueous solution, was intravenously administered via the tail vein at a dose of 30 mg/kg, whereupon a distinct body temperature lowering effect was observed. As shown in FIG. 8, intraperitoneal administration of the compound of Example 15 (100 mg/kg) 30 minutes prior to and 30 minutes subsequent to the administration of endotoxin showed remarkable antagonistic activities against the endotoxin-induced body temperature lowering effect.

The intravenous administration of endotoxin via the tail vein at a high dose (100 mg/kg) killed mice in all cases (10/10) within 48 hours. By the same treatment with the compound of Example 15, a distinct reduction in the mortality was observed, and mice in five cases out of ten cases survived even after 96 hours from the administration of endotoxin (Table 2).

TABLE 2

Inhibitory effect of the compound of the present invention on the endotoxin-induced mortality rate in mice

| Drug | Dose (mg/kg) (i.p.) | Survived number/number of the tested animals (survival rate (%)) Time after administration of endotoxin (hr) | | |
|---|---|---|---|---|
| | | 24 | 48 | 96 |
| Solvent* | 0 | 8/10 (80) | 0/10 (0) | 0/10 (0) |
| Compound of Example 15 | 100 × 2 | 10/10 (100) | 6/10 (60) | 5/10 (50) |

*0.15% sodium hydrogencarbonate aqueous solution

As is evident from the foregoing, the compound of the present invention showed remarkable antagonistic activities against the endotoxin shock.

Thus, the compounds of the present invention have excellent endothelin antagonistic activities and are useful as vasodilators or bronchodilators in the field of medicines, and they can be drugs for treating hypertension, acute renal failure, myocardial infarction, angina pectoris, cerebral infarction, cerebral vasospasm, asthma, endotoxin shock, endotoxin-induced multiple organ failure or disseminated intravascular coagulation, and/or cyclosporin-induced renal failure or hypertension. When used as drugs for treating such diseases, the compounds of the present invention can be used alone or in combination with other drugs for treatment.

The compounds of the present invention may be used in the form of drug formulations suitable for parenteral administration, oral administration or external administration by mixing them with solid or liquid excipient carriers known in this field. The drug formulations include a liquid formulation such as an injection formulation, an inhalant formulation, a syrup formulation or an emulsion, a solid formulation such as tablets, capsules or granules, and an external drug such as an ointment or a suppository. Further, these drug formulations may contain additives which are commonly employed, such as an adjuvant, a stabilizer, a wetting agent, an emulsifier, an absorption-promoting agent or a surfactant, as the case requires. As the additives, distilled water for injection, physiological saline, Ringer's solution, glucose, sugar syrup, gelatin, vegetable oil, cacao butter, ethylene glycol, hydroxypropyl cellulose, lactose, sucrose, corn starch, magnesium stearate and talc may be mentioned.

The dose of the compound of the present invention as an endothelin antagonis varies depending upon the manner of administration, the age and body weight of the patient and the condition of the patient to be treated. However, a typical administration method for an adult is oral administration or parenteral administration. The daily dose in the case of oral administration to an adult patient is from 0.1 to 100 mg/kg body weight, and the daily dose in the case of parenteral administration is from 0.01 to 10 mg/kg body weight.

Now, the present invention will be described in further detail with reference Examples. xamples. However, it should be understood to such specific Examples.

EXAMPLE 1 cyclo(-DTrp-DGlu-Ser-DVal-Leu-)

(1-a) DVal-Leu-OBzl.p-TsOH

To a solution of Leu-OBzl.p-TsOH(2.06 g), Boc-DVal (1.09 g), HOBT.H$_2$O(0.80 g) and N-methylmorpholine(0.55 ml) in dichloromethane(10 ml) was added EDCI HCl(1.01 g) under ice cooling. The resulting mixture was stirred at room temperature for 5 h. Saturated NaHCO$_3$(10ml) was added, and the mixture was extracted with dichloromethane(50 ml×3). The combined organic layers were dried over MgSO$_4$ and filtered. The solvent was evaporated under reduced pressure. The residue was purified by dry column flash chromatography on silica gel(Merck, KIESELGEL 60) with hexane/EtOAc(2/1) for elution to give Boc-nVal-Leu-OBzl(2.03 g) as a colorless powder. The dipeptide(1.47 g) was added by portions to TFA(3.5 ml) under ice cooling. The mixture was stirred under ice cooling for 30 min and concentrated in vacuo. To the residue was added saturated NaHCO$_3$(10 ml) and the mixture was extracted with dichloromethane(50 ml×3).

The combined organic layers were dried over MgSO$_4$, filtered and concentrated under reduced pressure. The residue was dissolved in methanol(5 ml) and treated with p-TsOH.H$_2$O(700 mg). Ether(100 ml) was added to the solution. The resulting precipitate was collected by filtration and dried in vacuo to give DVal-Leu-OBzl.p-TsOH(1.6 g) as colorless needles.

(1-b) Boc-Ser-DVVal-Leu

To a solution of DVal-Leu-OBzl.p-TsOH(394 mg), Boc-Ser(164 mg), HOBT.H$_2$O(129 mg) and N-methylmorpholine (88 μl) in dichloromethane(1.6 ml) was added EDCI.HCl (161 mg) under ice cooling. The reaction mixture was stirred at room temperature for 3 h. Saturated NaHCO, (2 ml) was added and the mixture was extracted with dichloromethane(15 ml×3). The combined organic layers were dried over MgSO$_4$, filtered and concentrated under reduced pressure. The residue was purified by dry column flash chromatography on silica gel(Merck, KIESELGEL 60) with dichloromethane/methanol(50/1) for elution to give a solid. The solid was dissolved in chloroform and precipitated with hexane to give Boc-Ser-DVal-Leu-OBzl(355 mg) as a colorless powder. The tripeptide(330 mg) was dissolved in THF(3.3 ml) and 10% Pd/C(33 mg) was added. The mixture was vigorously stirred at room temperature under an atmosphere of hydrogen(under atmospheric pressure) for 2 h. The reaction mixture was filtered and the filtrate was concentrated under reduced pressure. Saturated NaCl (2 ml) was added to the residue and the mixture was extracted with EtOAc(20 ml×3). The combined organic layers were dried over MgSO$_4$, filtered and concentrated under reduced pressure to give a solid. The solid was dissolved in chloroform and reprecipitated with hexane to give Boc-Ser-DVal-Leu(246 mg) as a colorless powder.

(1-c) DTrp(Z)-DGlu(OBzl)-O$^t$Bu

To a solution of Boc-DTrp(274 mg), nGlu(OBzl)-O$^t$Bu (264 mg) and HOBT.H$_2$O(145 mg) in dichloromethane(1.8 ml) was added EDCI.HCl(181 mg) under ice cooling. The reaction mixture was stirred at room temperature for 2 h and saturated NaHCO$_3$(2 ml) was added. The mixture was extracted with dichloromethane(20 ml×3). The combined organic layers were dried over MgSO$_4$, filtered and concentrated under reduced pressure. The residue was purified by dry column flash chromatography on silica gel(Merck, KIESELGEL 60) with chloroform/methanol(50/1) for elution to give Boc-DTrp(Z)-DGlu(OBzl)-O$^t$Bu(492 mg) as a pale yellow powder. The powder(232 mg) and tetrabutylammonium hydrogen sulfate(1.4 mg) were dissolved in dichloromethane(2 ml) and pulverized NaOH(26 mg) was added. To the mixture was added benzyl chloroformate (86 μl) under ice cooling and the resulting mixture was stirred under ice cooling for 1 h. After an addition of saturated NaHCO$_3$(2 ml), the reaction mixture was extracted with dichloromethane(20 ml×3). The combined organic layers were dried over MgSO$_4$, filtered and concentrated under reduced pressure. The residue was purified by dry column flash chromatography on silica gel(Merck, KIESELGEL 60) with hexane/EtOAc(4/1) for elution to give Boc-DTrp(Z)-DGlu(OBzl)-O$^t$Bu(258 mg) as a colorless powder. The powder(250 mg) was added by portions to TFA(1.8 ml) under ice cooling and the resulting mixture was stirred under ice cooling for 10 min and concentrated in vacuo. Saturated NaHCO$_3$(2 ml) was added to the residue and the mixture was extracted with dichloromethane(20 ml×3). The combined organic layers were dried over MgSO$_4$, filtered and concentrated under reduced pressure. The obtained crude oil was purified by dry column flash chromatography on silica gel(Merck, KIESELGEL 60) with dichloromethane/methanol (50/1) for elution to give DTrp(Z)-DGlu(OBzl)-O$^4$Bu(193 mg) as a pale yellow oil.

(1-d) cyclo(-DTrp-DGlu-Ser-DVal-Leu-)

To a solution of DTrp(Z)-DGlu(OBzl)-O$^t$Bu(184 mg, prepared in Example(1-c)), Boc-Ser-DVal-Leu(125 mg, prepared in Example(1-b)) and HOBT.H$_2$O(51 mg) in dichloromethane (1 ml) was added EDCI.HCl(63 mg) under ice cooling. The reaction mixture was stirred at room temperature for 2 h and saturated NaHCO$_3$(1 ml) was added. The mixture was extracted with dichloromethane(15 ml×3). The combined organic layers were dried over MgSO$_4$, filtered and concentrated under reduced pressure. The residue was purified by dry column flash chromatography on silica gel(Merck, KIESELGEL 60) with chloroform/methanol(50/1) for elution to give a solid. The solid was dissolved in chloroform and reprecipitated with hexane to give Boc-Ser-DVal-Leu-DTrp(Z)-Glu(OBzl)-O$^t$Bu(270 mg) as a colorless powder. The powder(81 mg) was added by portions to TFA(0.8 ml) under ice cooling and the mixture was stirred at room temperature for 1.5 h. TFA was removed in vacuo and the residue was dissolved in methanol and precipitated with water to give Ser-DVal-Leu-DTrp(Z)-DGlu(OBzl)(58 mg) as a colorless powder. The powder(77 mg) was dissolved in DMF(4.5 ml) and the solution was added dropwise over a period of 1.5 h to a solution of HOBT.H$_2$O(21 mg) and EDCL.HCl (21 mg) in DMF(4.5 ml). The reaction mixture was stirred at room temperature for 17 h and concentrated in vacuo. The residue was washed successively with saturated NaHCO$_3$, 1N HCl and water, and dried in vacuo to give cyclo(-DTrp(Z)-DGlu(OBzl)-Ser-DVal-Leu-)(65 mg) as a colorless powder. To a solution of the cyclic pentapeptide(34 mg) in DMF(2 ml) was added 10% Pd/C(17 mg). The mixture was vigorously stirred at room temperature under an atmosphere of hydrogen(under atmospheric pressure) for 2 h and filtered through Celite. The filtrate was concentrated in vacuo. The residue was triturated with water. The obtained precipitate was collected by filtration, washed with water and dried in vacuo to give the title compound(16 mg) as a pale brown powder.

m.p.: 275° C.(dec.).

IR(KBr,cm$^{-1}$): 3400,3292,2962,1662,1647,1539,741.

High Resolution FAB-MS(m/e,(C$_{30}$H$_{42}$N$_6$O$_8$+H)$^+$):

Calcd : 615.3142.

Found : 615.3127.

$^1$H-NMR(300 MHz,DMSO-d$_6$, δ ppm):0.65(3H,d,J=6.6Hz),
0.74(3H,d,J=6.6Hz),0.82(3H,d,J=6.6Hz),0.83(3H,d, J=6.6Hz), 1.00-1.10(1H,m),1.15-1.30(2H,m),1.-75-2.05(3H, m),2.05-2.30(2H,m),2.92(1H,dd, J=11.5Hz,14.2Hz),3.25
(1H,dd,J=3.0Hz,14.2Hz),3.40-3.55(1H,m),3.-55-3.75(1H, m),4.05-4.20(2H,m),4.-20-4.45(3H,m),4.67(1H,brs),6.96
(1H,t,J=7.5Hz),7.05(1H,
t,J=7.5Hz),7.12(1H,d,J=1.5Hz),
7.31(1H,d,J=7.5Hz),7.44(1H,d,J=7.5Hz),7.48(1H,d,J=9.5Hz),7.54(1H,d,J=7.5Hz),8.47(1H,d,J=6.6Hz),8.5-4(1H,
d,J=7.9Hz),8.69(1H,d,J=8.3Hz),10.79(1H,d,J=1.5Hz)

EXAMPLE 2 cyclo(-DTrp-DCys($O_3$Na)-Ala-DVal-Leu-)

To a solution of DVal-Leu-OBzl.p-TsOH(375 mg, prepared in Example(1-a)), Boc-Ala(144 mg), HOBT.-$H_2O$ (122 mg) and N-methylmorpholine(84 μl) in dichloromethane (1.6 ml) was added EDCI.HCl(153 mg) under ice cooling. The reaction mixture was stirred at room temperature for 2 h and saturated $NaHCO_3$ was added. The mixture was extracted with dichloromethane(15 ml×3). The combined organic layers were dried over $MgSO_4$, filtered and concentrated under reduced pressure. The residue was purified by dry column flash chromatography on silica gel(Merck, KIESELGEL 60) with chloroform/methanol(50/1) for elution to give Boc-Ala-DVal-Leu-OBzl(306 mg) as a colorless powder. The powder(300 mg) was added by portions to TFA(1.2 ml) under ice cooling and the reaction mixture was stirred at the same temperature for 30 min. TFA was removed in vacuo. Saturated $NaHCO_3$ (2 ml) was added to the residue and the mixture was extracted with dichloromethane(15 ml×3). The combined organic layers were dried over $MgSO_4$, filtered and concentrated under reduced pressure to give Ala-DVal-Leu-OBzl(233 mg) as a colorless powder. To a solution of the tripeptide(157 mg), Boc-DCys($O_3$-Na)(117 mg) and HOBT.$H_2O$(67 mg) in DMF(0.8 ml) was added EDCI.HCl (84 mg) under ice cooling. The reaction mixture was stirred at room temperature for 20 h and concentrated in vacuo. To the residue was added saturated $NaHCO_3$(2 ml) and the mixture was extracted with EtOAc(20 ml×3). The combined organic layers were dried over $Na_2SO_4$, filtered and concentrated under reduced pressure. The residue was purified by dry column flash chromatography on silica gel(Merck, KIESELGEL 60) with dichloromethane/methanol(10/1) for elution to give Boc-DCys(O,Na)-Ala-DVal-Leu-OBzl(210 mg) as a colorless powder. The powder(100 mg) was added by portions to TFA (0.75 ml) under ice cooling and the mixture was stirred under ice cooling for 1 h. TFA was removed in vacuo. To the residue was added 1N NaOH(0.15 ml) and the mixture was concentrated in vacuo to give crude DCys($O_3$Na)-Ala-DVal-Leu-OBzl(108 mg) which was used without further purification in the next step. To a solution of the crude tetrapeptide(108 mg), Z-DTrp(51 mg) and HOBT.$H_2O$ (25 ml) in DMF(0.3 ml) was added EDCI.HCl(32 mg) under ice cooling. The reaction mixture was stirred at room temperature for 2 h and concentrated in vacuo. To the residue was added saturated $NaHCO_3$(1 ml) and the mixture was extracted with EtOAc(10 ml×3). The combined organic layers were dried over $Na_2SO_4$, filtered and concentrated under reduced pressure. The residue was purified by dry column flash chromatography on silica gel (Merck, KIESELGEL 60) with dichloromethane/methanol (10/1) for elution to give Z-DTrp-DCys($O_3$Na) -Ala-DVal-Leu-OBzl(110 mg) as a colorless powder. The powder(97 mg) was dissolved in DMF(0.55 ml) and 10% Pd/C (29 mg) was added. The resulting mixture was stirred vigorously at room temperature under an atmosphere of hydrogen(under atmospheric pressure) for 3 h, and filtered. The filtrate was concentrated in vacuo to give DTrp-DCys($O_3$Na)-Ala-DVal-Leu(63 mg) as a colorless powder. A solution of the pentapeptide(33 mg) in DMF (2.5 ml) was added dropwise to a solution of HOBT.$H_2O$ (12 mg) and EDCI HCl(14 mg) in DMF(2.5 ml) over a period of 1.5 h. The reaction mixture was stirred at room temperature for 2 h and concentrated in vacuo. The residue was purified by reverse-phase column chromatography(NACALAI TESQUE, COSMOSIL 75 $C_{18}$-OPN) with methanol/water(4/1) for elution to give the title compound(17 mg) as a colorless powder.

m.p.: >300° C.

IR(KBr,$cm^{-1}$): 3450,2920,1647,1560,1386,1047.

High Resolution FAB-MS(m/e,($C_{28}H_{40}N_6O_8S$+H) +):

Calcd : 621.2695.

Found 621.2726.

$^1$H-NMR(300 MHz,DMSO-$d_6$, δ ppm):0.69 (3H,d,J=6.1Hz),
0.76(3H,d,J=6.1Hz),0.81(3H,d,J=6.7Hz),0.84(3H,d,J=6.7Hz),1.12(3H,d,J=6.9Hz),1.05-1.20(1H,m),1.-20-1.35
(2H,m),1.80-1.90(1H,m),2.78(1H,dd,J=3.6Hz,13.1Hz), 2.91(1H,dd,J=10.5Hz,14.6Hz),3.11(1H,dd,J=8.8Hz,1-3.1
Hz),3.22(1H,dd,J=2.4Hz,14.6Hz),4.08(1H,dd,J=8.0Hz, 8.9Hz),4.15-4.30(2H,m),4.35(1H, quint,J=7.2Hz),4.-40-4.50(1H,m),6.96(1H,
t,J=7.5Hz),7.04(1H,t,J=7.5Hz),7.18 (1H,s),7.30(1H,d,J=7.5Hz),7.52(1H,d,
J=7.5Hz),7.72(1H,d,J=7.0Hz),7.88(1H,d,J=8.9Hz),8.-06(1H,d,J=7.4Hz),8.15
(1H,d,J=7.2Hz),8.72(1H,d,J=7.6Hz),10.77(1H,s).

EXAMPLE 3 cyclo(-DTro-DCys($O_3$Na)-Pro-DVal-Leu-)

Boc-DTrp-DCys($O_3$Na)-Pro-DVal-Leu-OBzl(322 mg) prepared in the same manner as described in Exmaple 2 was dissolved in DMF(1.0 ml) and hydrazine monohydrate(75 μl) was added. The reaction mixture was stirred at room temperature for 22 h and concentrated in vacuo. The residue was purified by reverse-phase column chromatography(NACALAI TESQUE, COSMOSIL 75 $C_{18}$-OPN) with methanol/water(1/1) for elution to give the corrsponding hydrazide(149 mg) as a colorless solid. The hydrazide(149 mg) was dissolved in TFA/EDT(V/V, 95/5, 20 ml) and the mixture was stirred under ice cooling for 15 min. The reaction mixture was concentrated under reduced pressure and the resulting residue was purified by reverse-phase column chromatography(NACALAI TESQUE, COSMOSIL 75 $C_{18}$-OPN) with methanol/water(2/3) for elution to give DTrp-DCys($O_3$H)-Pro-DVal-Leu-NHNH$_2$(103 mg) as a pale yellow soid. The solid was dissolved in DMF (1.0 ml) under argon. The solution was cooled to −60° C. and 3.1N hydrogen chloride/1,4-dioxane(120 μl) was added at the same temperature. After the temperature of a cooling bath was raised to −30° C.~−20° C., isoamyl nitrite (ca. 40 μl) was added by portions until the spot of hydrazide on TLC was disappeared. The reaction mixture was again cooled to −60° C. and slowly diluted with DMF (40 ml). By addition of TEA(75 μl), the pH of the reaction mixture was adjusted to 7.5 and the resulting reaction mixture was allowed to stand at −20° C. (in a freezer) overnight. The mixture was concentrated in vacuo and the residue was purified by reverse-phase column chromatography(NACALAI TESQUE, COSMOSIL 75 $C_{18}$-OPN) with methanol/water(3/7) for elution to give a crude product. Further purification of the crude product by successive chromatography over cation exchange resins(AMBERLITE IR-120B: H$^+$-form and Amberlite IRC-50: Na+-form), followed by reprecipitation from ethanol(10 ml) with ether(50 ml) gave the title compound (60 mg) as a pale yellow powder.

m.p.: 285° C.(dec.).

IR(KBr,cm$^{-1}$): 3418,1668,1539,1461,1221,1044.

High Resolution FAB-MS(m/e,(C$_{30}$H$_{41}$N$_6$NaO$_8$S+H)$^+$):

Calcd : 669.2682.
Found : 669.2733.

$^1$H-NMR(300 MHz,DMSO-d$_6$, δ ppm):0.62(3H,d,J=6.3Hz),0.71(3H,d,J=6.3Hz),0.81(3H,d,J=6.6Hz),0.83(3H,d,J=6.6Hz),0.95-1.10(1H,m),1.16-1.22(2H,m),1.55-1.93(4H,m),2.-19-2.27(1H,m),2.58(1H,dd,J=2.7Hz,12.2Hz),2.92(1H,dd,J=11.6Hz,14.3Hz),3.15-3.45(3H,m),3.-63-3.71(1H,m), 4.05-4.30(3H,m),4.62(1H,d-like,J=6.6Hz),4.93-5.03(1H,m),6.95(1H,t,J=7.5Hz),7.03(1H,t,J=7.5Hz),7.13(1H,d,J=1.7Hz),7.20(1H,d,J=8.3Hz),7.30(1H,d,J=7.5Hz),7.-53 (1H,d,J=7.5Hz),8.10(1H,d,J=9.0Hz),8.57(1H,d,J=7.1Hz), 8.69(1H,d,J=8.3Hz),10.77(1H,d,J=1.7Hz).

Optical Rotations: $[α]_D^{20}$= +60.5°(c 0.35, MeOH).

EXAMPLE 4 cyclo(-DTrp-DAsp-Lys-DVal-Leu-) TFA salt

Fmoc-Leu-resin(0.093 mmol/g, 1.0 g) which was prepared from ULTROSYN B(Pharmacia LKB Biotechnology) and Fmoc-Leu by a symmetrical acid anhydride method, was previously swelled in DMF, and packed in a reaction column of a BIOLYNX 4175 peptide synthesizer(Pharmacia LKB Biotechnology) and a solid phase peptide synthesis was performed manually by the standard protocol; 20% piperidine/DMF was pumped through the reaction column for 10 min(flow rate: 3.5 ml/min) to deprotect Fmoc group. Then DMF was pumped for 10 min(3.5 ml/min) to remove excess base. Each 2.5 equivalents of Fmoc-DVal-OPfp and HOBT.H$_2$O was dissolved in DMF(1 ml). The solution was drawn into the reaction system and recirculated for 1 h(3.5 ml/min) to achieve acylation of the amino groups present on the resin. DMF was pumped for 5 min (3.5 ml/min) to wash excess reagents out, to give Fmoc-DVal-Leu-resin. In a similar manner, Fmoc-Lys(Boc)-OPfp, Fmoc-DAsp(O$^t$Bu) and Fmoc-DTrp-OPfp were successively coupled with the corresponding resin bound peptide. In the case of the coupling reaction of DAsp, were used each 5 equivalents of Fmoc-DAsp(O$^t$Bu) and HOBT.H$_2$O, and 4 equivalents of DIPC. Completion of each acylation reaction was judged by the Kaiser test [Anal. Biochem., 34, 595(1970)]. If the acylation reaction was imcomplete, additional recirculation was performed until the Kaiser test turned negative. Finally the Fmoc group of the resin bound pentapeptide was deprotected in a reaction column by pumping 20% piperidine/DMF for 10 min(3.5 ml/min). The resin was unpacked from a reaction column, washed on a glass filter successively with DMF, tert-amyl alcohol, acetic acid, tert-amyl alcohol, DMF and ether, and dried in vacuo to give DTrp-DAsp(O$^t$Bu)-Lys(Boc)-DVal-Leu-resin (1.06 g). 10% Hydradine monohydrate/1,4-dioxane/methanol(v/v, 9/1, 3.0 ml) was added to the resin and the mixture was allowed to stand at room temperature for 2 h with occasional shaking. The resin was filtered out and washed several times with each small amount of 1,4-dioxane/methanol(9/1). The combined filtrate and washings were neutralized with dry ice and concentrated in vacuo. Water(10 ml) was added to the residue to precipitate a solid, which was collected by filtration and dried in vacuo to give DTrp-DAsp(O$^t$Bu)-Lys(Boc) -DVal-Leu-NHNH,(65.3 mg) as a colorless powder.

The hydrazide(64.2 mg) prepared above was cyclized in the same manner described in Example 3 to give a DMF solution of the protected cyclic pentapeptide. The DMF solution was concentrated in vacuo. Water(10 ml) was added to the residue to precipitate a solid, which was collected by filtration and dried in vacuo to give cyclo (-DTrp-DAsp(O$^t$Bu)-Lys(Boc)-DVal-Leu-)(58.9 mg) as a pale yellow powder.

The protected cyclic pentapeptide(55.1 mg) was dissolved in TFA/EDT(v/v, 95/5, 5.5 ml). The mixture was stirred at room temperature for 30min and concentrated under reduced pressure. The residue was triturated with methanol(2 ml)/ether(30 ml) to give the title compound(48.1 mg) as an off-white powder.

m.p.: 230° C.(dec.).

FAB-MS(m/e,(C$_{32}$H$_{47}$N$_7$O$_7$+H)$^+$): 642.

$^1$H-NMR(300 MHz,DMSO-d$_6$,δ ppm):0.64 (3H,d,J=6.3Hz), 0.75(3H,d,J=6.3Hz),0.81(3H,d,J=7.3Hz),0.84(3H,d,J=7.3Hz),0.94-1.06(1H,m),1.19-1.33(4H,m),1.45-1.85 (5H, m),2.45-2.55(1H,m),2.-68-2.78(3H,m),2.88(1H,dd,J=11.1 Hz,14.4Hz),3.25(1H,dd,J=3.8Hz,14.4Hz),4.03-4.10(1H,m), 4.16(1H,dd,J=6.5Hz,9.2Hz),4.25-4.35(2H,m),4.-48-4.57 (1H,m),6.96(1H,t,J=7.5Hz),7.05(1H,t,J=7.5Hz),7.11(-1H, d,J=2.0Hz),7.32(1H,d,J=7.5Hz),7.36(1H,d,J=9.2Hz),-7.51 (1H,d,J=7.5Hz),7.58(1H,d,J=7.1Hz),8.64(1H,d,J=6.3-Hz), 8.71-8.75(2H,m),10.81(1H,d,J=2.0Hz).

Optical Rotations: $[α]_D^{20}$= -8.6°(c 1.0, DMSO)

EXAMPLE 5 cyclo(-DTrp-DCys(O$_3$Na)-Pro-DVal-Nle-)

Fmoc-Nle-resin(200 mg, 0.476 mmol/g) which was prepared from p-alkoxybenzyl alcohol resin(Kokusan Chemical Works) and Fmoc-Nle by a DCC-DMAP method, was packed in a polypropylene column(10 mmΦ×60 mm) and a solid-phase synthesis was performed as follows; 20% piperidine/DMF (3 ml) was added to the column and the column was vibrated for 5 min, then DMF was removed from the column. This procedure was repeated 3 times to remove Fmoc group. The resin in the column was washed with each 3 ml of DMF by vibrating the column for 1 min(6 times). A solution of each 2.5 equivalents of Fmoc-DVal, HOBT.H$_2$O and DIPC in DMF(1.0 ml) was added into the column and the acylation reaction was performed by vibrating the column at room temperature for 2 h. Completion of the reaction was judged by the Kaiser test. Excess reagents were removed and the resin was washed with DMF (each 3 ml, 1 min×4) to give Fmoc-DVal-Nle-resin. In the same manner, Fmoc-Pro, Fmoc-DCys(O$_3$Bu$_4$N) and Fmoc-DTrp were successively coupled with the corresponding resin bound peptide to give Fmoc-DTrp-DCys(O$_3$Bu$_4$N)-Pro-DVal-Nle-resin. After the deprotection of the Fmoc group with 20% piperidine/DMF (each 3 ml, 5 min×3), the resin was successively washed with DMF(3 ml×6) and methanol(3 ml×3), and dried in vacuo to give DTrp-DCys(O$_3$Bu$_4$N)-Pro-DVal-Nle-resin, which was soaked in TFA/phenol(95/5, 3 ml) and vibrated at room temperature for 20 min. The resin was filtered out and washed with TFA(3 ml×2). The combined filtrate and washings were concentrated under reduced pressure. The residue was triturated with hexane/ether to give a linear pentapeptide(27 mg) as a pale yellow powder.

A solution of the linear pentapeptide prepared above(26 mg) in DMF(2 ml) was added dropwise to a solution of EDCI.HCl(8 mg) and HOBT.H$_2$O(7 mg) in DMF(2 ml) under ice cooling over a period of 1 h. The reaction mixture was stirred at room temperature overnight and concentrated in vacuo. The residue was purified by reverse-phase chromatography on a SEP-PAK C$_{18}$ cartridge(Waters) with methanol/water(10/1) for elution to give a cyclic pentapeptide tetrabutyl ammonium salt(19 mg). The salt was dissolved in 10% aq. methanol. By passing the aq. methanol solution through a column of ion exchange resin (AMBERLITE IR-120B, Na$^+$-form), the ammonium salt was converted into the corresponding sodium salt. After concentration of the solution, the residue was purified by thin layer chromatography on silica gel(Analytichem International, Empore sheet) with chloroform/methanol/acetic acid(5/1/1) for development to give the title compound(8.6 mg) as a pale yellow powder.

m.p.: 217°–221° C.

IR(KBr,cm$^{-1}$): 3436,2962,1659,1536,1461,1203,1044.

High Resolution FAB-MS(m/e,(C$_{30}$H$_{42}$N$_6$O$_8$S+H)$^+$):

Calcd : 647.2863.

Found : 647.2825.

$^1$H-NMR(300 MHz,DMSO-d$_6$,δ ppm):0.69 (3H,t,J=7.4Hz),0.81(3H,d,J=6.3Hz),0.83(3H,d,J=5.7Hz),0.62–0.96(2H,m), 1.01–1.13(2H,m),1.-28–1.35(2H,m),1.54–1.66(1H,m),1.72–1.79(2H,m),2.-17–2.27(2H,m),2.54–2.59(1H,m),2.92(1H,dd, J=11.2Hz,14.4Hz),3.10–3.50(3H,m),3.-65–3.68(1H,m),3.98–4.10(2H,m),4.-22–4.30(1H,m),4.61(1H,d-like,J=6.4Hz), 4.92–5.00(1H,m),6.96(1H,t,J=7.8Hz),7.03(1H,t,J=7.8-Hz), 7.13(1H,d,J=1.8Hz),7.20(1H,d,J=8.1Hz),7.29(1H,d,J-=7.8Hz),7.53(1H,d,J=7.8Hz),8.12(1H,d,J=9.2Hz),8.5-6(1H, d,J=7.1Hz),8.61(1H,d,J=8.3Hz),10.75(1H,d,J=1.8Hz-).

Optical Rotations: [α]$_D^{20}$= +22.8°(c 0.41, MeOH).

EXAMPLE 6 cyclo(-DTrp-DAsp-Leu-DVal-Leu-)

Fmoc-Leu-resin(228 mg, 0.439 mmol/g) which was prepared from p-alkoxybenzyl alcohol resin(Kokusan Chemical Works) and Fmoc-Leu by a DCC-DMAP method, was successively acylated in the same manner described in Example 5 to give DTrp-DAsp(O$^t$Bu)-Leu-DVal-Leu-resin (247 mg).

The resin was added to 10% hydradine monohydrate/DMF(2.0 ml) and the mixture was stirred at room temperature for 5 h. The resin was filtered out and washed several times with each small amount of DMF. The combined filtrate and washings were neutralized with dry ice and concentrated in vacuo. The residue was triturated with water(5 ml) to give DTrp-DAsp (O$^t$Bu)-Leu-DVal-Leu-NHNH$_2$(66.4 mg) as a colorless powder.

The hydrazide(64.1 mg) was cyclized and deprotected in the same manner described in Example 4 to give the title compound(40 mg) as an off-white powder.

m.p.: 275° C.(dec.).

IR(KBr,cm$^{-1}$): 3304,3064,2962,1659,1536,1464,1392,1221.

High Resolution FAB-MS(m/e,(C$_{32}$H$_{46}$N$_6$O$_7$+H)$^+$):

Calcd : 627.3506.

Found : 627.3529.

$^1$H-NMR(300 MHz,DMSO-d$_6$,δ ppm):0.65 (3H,d,J=6.4Hz),0.75(3H,d,J=6.4Hz),0.73–0.89(12H,-m),0.93–1.05(1H,m), 1.18–1.24(2H,m),1.-38–1.65(3H,m),1.75–1.85(1H,m),2.-45–2.55(1H,m),2.72(1H,dd,J=10.2Hz,16.4Hz),2.88(1H-,dd, J=11.2Hz,14.4Hz),3.20–3.39(1H,m),4.-05–4.10(1H,m),4.15(1H,dd,J=6.6Hz,9.3Hz),4.-27–4.40(2H,m),4.47–4.54(1H,m), 6.96(1H,t,J=7.6Hz),7.04(1H,t,J=7.6Hz),7.11(1H,d,J-=1.9Hz),7.31(1H,d,J=7.6Hz),7.41(1H,d,J=9.3Hz),7.5-2(1H,d,J=7.6Hz),7.56(1H,d,J=7.1Hz),8.60(1H,d,J=6.-1Hz),8.69 (1H,d,J=8.3Hz),8.69(1H,d,J=8.3Hz),10.78(1H,d,J=1.-9Hz),12.23(1H,brs).

Optical Rotations: [α]$_D^{20}$= −12.6°(c 0.56, DMSO).

EXAMPLE 7 cyclo(-DTrp-DGlu-Ala-DVal-Leu-)

The title compound was prepared from Boc-DTrp, Glu(OBzl)-O$^t$Bu, Boc-Ala, Boc-DVal and Leu-OBzl.p-TsOH according to the same procedure described in Example 1.

m.p.: >295 ° C.

IR(KBr,cm$^{-1}$): 3280,1659,1644,1548.

High Resolution FAB-MS(m/e,(C$_{30}$H$_{42}$N$_6$O$_7$S+H)$^+$):

Calcd : 599.3193.

Found 599.3249.

$^1$H-NMR(300 MHz,DMSO-d$_6$,δ ppm):0.64 (3H,d,J=6.4Hz), 0.74(3H,d,J=6.4Hz),0.82(3H,d,J=6.6Hz),0.83(3H,d,J-=6.6Hz),0.95–1.10(l,m),1.14(3H,d,J=6.9Hz),1.20(2H,t, J=7.6Hz),1.75–2.00(3H,m),2.-10–2.25(2H,m),2.91(1H,dd, J=11.8Hz,14.4Hz),3.25–3.35(1H,m),4.-05–4.20(2H,m),4.20–4.35(2H,m),4.40(1H-,quint,J=7.1Hz),6.96(1H,t,J=7.6Hz), 7.04(1H,t,J=7.6Hz),7.12(1H,d,J=1.4Hz),7.31(1H,d,J-=7.6Hz),7.39(1H,d,J=7.3Hz),7.51(1H,d,J=8.3Hz),7.5-3(1H, d,J=7.6Hz),8.55(1H,d,J=6.4Hz),8.72(1H,d,J=8.0Hz),-8.75(1H,d,J=8.4Hz),10.79(1H,d,J=1.4Hz),12.09(1H,b-rs).

Optical Rotations: [α]$_D^{20}$= −10.0°(c 1.0, DMSO).

EXAMPLE 8 cyclo(-DTrp-DGlu-Ala-DaIle-Leu-)

The title compound was prepared from Boc-DTrp, DGlu(OBzl)-O$^t$Bu, Boc-Ala, Boc-DaIle and Leu-OBzl.p-TsOH according to the same procedure described in Example 1.

m.p.: >295° C.

IR(KBr,cm$^{-1}$): 3286,2962,1659,1644,1545.

High Resolution FAB-MS(m/e,(C$_{31}$H$_{44}$N$_6$O$_7$+H)$^+$):

Calcd : 613.3350.

Found : 613.3377.

¹H-NMR(300 MHz,DMSO-d₆,δ ppm):0.63(3H,d,J=6.4Hz), 0.73(3H,d,J=6.5Hz),0.78(3H,d,J=6.7Hz),0.87-(3H,t,J=7.4Hz),0.90-1.10(2H,m),1.13(3H,d,J=7.1Hz),1.20-1.40(3H,m),1.55-1.65(1H,m),1.80-2.00(2H,m),2.05-2.25(2H,m),2.90(1H,dd,J=11.8Hz,14.6Hz),3.28(1H,dd,J=2.3Hz, 14.6Hz),4.06(1H,q,J=6.9Hz),4.21-4.34(3H,m),4.45(1H,quint,J=7.1Hz),6.96(1H,t,J=7.6Hz),7.04(1H,t,J=7.6Hz), 7.12(1H,d,J=1.8Hz),7.31(1H,d,J=7.6Hz),7.45(1H,d,J=9.4Hz),7.49(1H,d,J=7.8Hz),7.52(1H,d,J=7.6Hz),8.60(1H, d,J=6.6Hz),8.75(1H,d,J=7.0Hz),8.78(1H,d,J=7.0Hz),10.78(1H,d,J=1.8Hz),12.02(1H,brs).

Optical Rotations: $[\alpha]_D^{20}$ = −6.9°(c 1.0, DMSO).

EXAMPLE 9 cyclo(-DTrp-DGlu-Asp-DVal-Leu-)

The title compound was prepared from Boc-DTrp, DGlu(OBzl)-O'Bu, Boc-Asp(OBzl), Boc-DVal and Leu-O'Bu.HCl according to the same procedure described in Example 1.

m.p.: 268° C.(dec.).
IR(KBr,cm⁻¹): 3424,2955,1665,542,1389,743.
High Rsolution FAB-MS(m/e,($C_{31}H_{42}N_6O_9$+H)⁺):
Calcd : 643.3091.
Found : 643.3072.
¹H-NMR(300 MHz,DMSO-d₆,50° C.δ ppm):0.67(3H,d,J=6.7Hz),0.74(3H,d,J=6.0Hz),0.82(3H,d,J=6.4Hz),0.84(3H, d,J=6.5Hz),1.08-1.21(1H,m),1.22-1.34(2H,m),1.81-1.98(3H,m),2.02-2.18(2H,m),2.33-2.55(1H,m),2.68-2.77(1H, m),2.92-3.02(1H,m),3.14-3.31(1H,m),4.10(1H,dd,J=7.2Hz, 8.7Hz),4.12-4.27(2H,m),4.30-4.41(1H,m),4.52-4.66(1H,m),6.95(1H,t,J=7.3Hz),7.03(1H,t,J=7.3Hz),7.13(1H,brs), 7.30(1H,d,J=7.3Hz),7.51(1H,d,J=7.2Hz),7.54(1H,d,J=7.3Hz),7.75(1H,brs),8.40(1H,d,J=7.1Hz),8.60(2H,brs),10.69(1H,brs).

According to the same procedure described in Example 4, each title compound described in the following Examples 10-43 was prepared from the corresponding Fmoc amino acids in which sidechain functional groups were protected with the appropriate protective groups, if necessary.

EXAMPLE 10 cyclo(-DTrp-DGlu-Pro-DVal-Leu-)

m.p.: 200° C.(dec.).
IR(KBr,cm⁻¹): 3412,2968,1683,1539,1461,1206,1182,1137, 842,800.
High Resolution FAB-MS(m/e,($C_{32}H_{44}N_6O_7$+H)⁺):
Calcd 625.3350.
Found 625.3334.
¹H-NMR(300 MHz,DMSO-d₆,δ ppm):0.59(3H,d,J=6.5Hz), 0.73(3H,d,J=6.5Hz),0.82(3H,d,J=6.5Hz),0.86(3H,d,J=6.5Hz), 0.90-1.02(1H,m),1.05-1.25(2H,m),1.50-2.04(6H,m),2.18-2.35(3H,m),2.89(1H,dd,J=12.0Hz,14.2Hz),3.05-3.15(1H,m),3.20-3.65(2H,m),3.97(1H,q,J=5.5Hz),4.11(1H,dd,J=8.2Hz,10.3Hz),4.19-4.32(1H,m),4.64-4.75(1H,m), 4.76(1H,d-like,J=7.1Hz),6.95(1H,t,J=7.4Hz),7.04(1H,t, J=7.4Hz),7.12(1H,d,J=1.8Hz),7.30(1H,d,J=7.4Hz),7.52(1H,d,J=7.4Hz),7.56(1H,d,J=10.3Hz),7.64(1H,d,J=9.3Hz), 8.70(1H,d,J=5.5Hz),8.78(1H,d,J=8.0Hz),10.79 (1H,d,J=1.8Hz),12.09(1H,brs).

EXAMPLE 11 cyclo(-DTrp-DAsp-Gly-DVal-Leu-)

m.p.: 250° C.(dec.).
IR(KBr,cm⁻¹): 3418,2962,1659,1542,1392,1236,1176.
High Resolution FAB-MS(m/e,($C_{28}H_{38}N_6O_7$+H)⁺):
Calcd : 571.2880.
Found : 571.2917.
¹H-NMR(300 MHz,DMSO-d₆,δ ppm):0.64(3H,d,J=6.5Hz), 0.74(3H,d,J=6.5Hz),0.80(3H,d,J=6.6Hz),0.83(1H,d,J=6.6Hz),0.94-1.08(1H,m),1.20(2H,t,J=6.6Hz),1.70-1.84(1H,m),2.41-2.54(1H,m),2.75(1H,dd,J=10.1Hz,16.2Hz), 2.87(1H,dd,J=11.5Hz,14.6Hz),3.24-3.45(1H,m),4.03-4.15(3H,m),4.24(1H,dd,J=7.4Hz,13.9Hz),4.30-4.39(1H,m), 4.53-4.60(1H,m),6.95(1H,t,J=7.8Hz),7.03(1H,t,J=7.8Hz), 7.10(1H,d,J=2.0Hz),7.30(1H,d,J=7.8Hz),7.37(1H,d,J=9.6Hz),7.51(1H,d,J=7.8Hz),7.62(1H,d,J=7.5Hz),8.62-8.73(2H,m),8.97-9.06(1H,m),10.78(1H,d,J=2.0Hz).

EXAMPLE 12 cyclo(-DTrp-DAsp-Ala-DVal-Leu-)

m.p.: >300° C.
IR(KBr,cm⁻¹): 3286,3082,2968,1644,1554,1461,1389,1233, 741.
High Resolution FAB-MS(m/e,($C_{29}H_{40}N_6O_7$+H)⁺):
Calcd : 585.3037.
Found : 585.3057.
¹H-NMR(300 MHz,DMSO-d₆,δ ppm):0.64(3H,d,J=6.4Hz), 0.75(3H,d,J=6.4Hz),0.82(3H,d,J=6.3Hz),0.84(3H,d,J=6.3Hz),0.94-1.10(1H,m),1.13(3H,d,J=7.3Hz),1.15-1.27(2H,m),1.74-1.83(1H,m),2.40-2.60(1H,m),2.73(1H,dd, J=10.2Hz,16.1Hz),2.87(1H,dd,J=11.3Hz,14.6Hz),3.20-3.45(1H,m),4.03-4.10(1H,m),4.18(1H,dd,J=6.9Hz,9.4Hz), 4.29-4.38(1H,m),4.45(1H,quint,J=7.3Hz),4.50-4.60(1H,m),6.96(1H,t,J=7.6Hz),7.04(1H,t,J=7.6Hz),7.10(1H,d, J=1.5Hz),7.31(1H,d,J=7.6Hz),7.37(1H,d,J=9.4Hz),7.52(1H,d,J=7.6Hz),7.60(1H,d,J=7.4Hz),8.65(1H,d,J=5.6Hz), 8.73(1H,d,J=7.8Hz),8.77(1H,d,J=7.3Hz),10.78(1H,d,J=1.5Hz).

Optical Rotations: $[\alpha]_D^{20}$ = +3.3°(c 0.12, DMSO).

EXAMPLE 13 cyclo(-DTrp-DAsp-MeAla-DVal-Leu-)

m.p.: 210° C.(dec.).
IR(KBr,cm⁻¹): 3328,2962,1659,1536,1464,1395,1341,1233, 741.
High Resolution FAB-MS(m/e,($C_{30}H_{42}N_6O_7$+H)⁺):
Calcd : 599.3193.
Found : 599.3198.

¹H-NMR(300 MHz,DMSO-d₆,δ ppm):0.61(3H,d,J=6.5Hz),
0.72(3H,d,J=6.5Hz),0.82(6H,d,J=6.3Hz),0.90-1.04(1H,m),
1.05-1.24(5H,m),1.65-1.77(1H,m),2.16-2.55(2H,m),2.72-3.45(5H,m),3.95-4.02(1H,m),4.13-4.29(2H,m),4.95-5.06(1H,m),5.07-5.18(1H,m),6.85(1H,br),6.95(1H,t,J=7.5Hz),
7.01(1H,t,J=7.5Hz),7.13(1H,brs),7.30(1H,d,J=7.5Hz),
7.51(1H,d,J=7.5Hz),7.63(1H,br),8.73-8.86(2H,m),10.80(1H,brs).

Optical Rotations: [α]_D^20 = +13.0°(c 0.58, DMSO).

EXAMPLE 14 cyclo(-DTrp-DAsp-Met-DVal-Leu-)

m.p.: 277° C.(dec.).
IR(KBr,cm⁻¹): 3298,3064,2968,1656,1539,1233,744.
High Resolution FAB-MS(m/e,(C₃₁H₄₄N₆O₇+H)⁺):
Calcd : 645.3070.
Found : 645.3076.
¹H-NMR(300 MHz,DMSO-d₆,δ ppm):0.64(3H,d,J=6.4Hz),
0.74(3H,d,J=6.4Hz),0.81(3H,d,J=7.1Hz),0.84(3H,d,J=7.1Hz),0.90-1.10(1H,m),1.21(2H,t,J=7.2Hz),1.75-2.00(3H,m),2.02(3H,s),
2.30-2.60(3H,m),2.72(1H,dd,J=10.6Hz,16.2Hz),2.88(1H,dd,J=11.6Hz,14.1Hz),3.20-3.40(1H,m),
4.06(1H,q,J=7.2Hz),4.17(1H,dd,J=6.3Hz,9.3Hz),4.25-4.40(1H,m),4.40-4.60(2H,m),6.96(1H,t,J=7.4Hz),7.04(1H,t,J=7.4Hz),7.11(1H,d,J=2.0Hz),7.31(1H,d,J=7.4Hz),7.34(1H,d,J=9.3Hz),7.52(1H,d,J=7.4Hz),7.55(1H,d,J=7.4Hz),
8.65(1H,d,J=7.2Hz),8.74(1H,d,J=8.5Hz),8.84(1H,d,J=7.8Hz),10.79(1H,d,J=2.0Hz).

EXAMPLE 15 cyclo(-DTrp-DAsp-Pro-DVal-Leu-)

m.p.: 160° C.(dec.).
IR(KBr,cm⁻¹): 3442,2960,1653,1536,1458.
High Resolution FAB-MS(m/e,(C₃₁H₄₂N₆O₇+H)⁺):
Calcd : 611.3193.
Found : 611.3206.
¹H-NMR(300 MHz,DMSO-d₆,δ ppm):0.60(3H,d,J=6.6Hz),
0.72(3H,d,J=6.6Hz),0.82(3H,d,J=6.5Hz),0.86(3H,d,J=6.5Hz),0.90-1.10(1H,m),1.10-1.28(2H,m),1.55-1.98(4H,m),2.21-2.32(1H,m),2.34(1H,dd,J=3.9Hz,16.1Hz),2.79(1H,dd,J=10.2Hz,16.1Hz),2.88(1H,dd,J=11.7Hz,14.4Hz),3.10-3.35(3H,m),3.95-4.03(1H,m),4.13(1H,dd,J=8.3Hz,10.3Hz),
4.22-4.31(1H,m),4.76(1H,d-like,J=7.0Hz),4.97(1H,dt,J=3.9Hz,8.8Hz),6.95(1H,t,J=7.3Hz),7.04(1H,t,J=7.3Hz),
7.13(1H,d,J=1.7Hz),7.31(1H,d,J=7.3Hz),7.49(1H,d,J=10.3Hz),7.52(1H,d,J=7.3Hz),7.71(1H,d,J=8.8Hz),8.75-8.79(2H,m),10.80 (1H,d,J=1.7Hz).

Optical Rotations: [α]_D^20 = +50.3°(c 0.31, MeOH).

EXAMPLE 16 cyclo(-DTrp-DAsp-Tyr-DVal-Leu-)

m.p.: 240° C.(dec.).
IR(KBr,cm⁻¹):
3298,2962,1671,1521,1464,1374,1223,1176, 744.
High Resolution FAB-MS(m/e,(C₃₅H₄₄N₆O₈+H)⁺):
Calcd : 677.3299.
Found : 677.3329.
¹H-NMR(300 MHz,DMSO-d₆,δ ppm):0.64(3H,d,J=6.5Hz),
0.74(6H,d,J=6.5Hz),0.79(3H,d,J=6.5Hz),0.95-1.13(1H,m), 1.21(2H,t,J=7.1Hz),1.70-1.83(1H,m),2.39-2.47(1H,m), 2.62-2.77(2H,m),2.82-2.94(2H,m),3.25-3.40(1H,m),4.03-4.16(2H,m),4.29-4.37(1H,m),4.41-4.55(2H,m),6.60(2H,d,J=8.6Hz),6.95(1H,t,J=7.5Hz),7.00(2H,d,J=8.6Hz),7.03(1H,t,J=7.5Hz),7.09(1H,d,J=1.9Hz),7.30(1H,d,J=7.5Hz),
7.35(1H,d,J=9.6Hz),7.51(1H,d,J=7.5Hz),7.66(1H,d,J=7.3Hz),8.55(1H,d,J=6.4Hz),8.64(1H,d,J=8.6Hz),8.77(1H,d,J=8.3Hz),9.08(1H,s),10.77(1H,d,J=1.9Hz),12.19(1H,brs).

EXAMPLE 17 cyclo(-DTrp-DAsp-Trp-DVal-Leu-)

m.p.: 294° C.(dec.).
IR(KBr,cm⁻¹)
3412,2962,1662,1539,1464,1230,1098,744.
High Resolution FAB-MS(m/e,(C₃₇H₄₅N₇O₇+H)⁺):
Calcd : 700.3459.
Found : 700.3422.
¹H-NMR(300 MHz,DMSO-d₆,δ ppm):0.65(3H,d,J=6.5Hz),
0.72(3H,d,J=6.5Hz),0.75(3H,d,J=6.5Hz),0.80(3H,d,J=6.5Hz),0.98-1.13(1H,m),1.15-1.32(2H,m),1.70-1.85(1H,m),2.36-2.59(1H,m),2.74(1H,dd,J=9.9Hz,16.3Hz),2.80(1H,dd,J=15.3Hz,16.1Hz),2.87(1H,dd,J=11.5Hz,16.1Hz),3.18(1H,dd,J=15.1Hz,17.3Hz),3.24-3.37(1H,m),4.02-4.17(2H,m),4.31-4.40(1H,m),4.51-4.69(2H,m),6.95(2H,t,J=7.5Hz),
7.04(2H,t,J=7.5Hz),7.10(1H,d,J=1.8Hz),7.11(1H,d,J=1.8Hz),7.29(1H,d,J=7.5Hz),7.30(1H,d,J=7.5Hz),7.44(1H,d,J=9.8Hz),7.47(1H,d,J=7.5Hz),7.52(1H,d,J=7.5Hz),7.69(1H,d,J=7.3Hz),8.55(1H,d,J=6.3Hz),8.64(1H,d,J=8.6Hz),
8.80(1H,d,J=8.4Hz),10.73(1H,d,J=1.8Hz),10.78(1H,d,J=1.8Hz),12.19(1H,brs).

Optical Rotations: [α]_D^20 = -6.1°(c 0.42, DMSO).

EXAMPLE 18 cyclo(-DTrp-DAsp-His-DVal-Leu-)

m.p. 253° C.(dec.).
IR(KBr,cm⁻¹): 3310,2968,1668,1536,1101.
High Resolution FAB-MS(m/e,(C₃₂H₄₂N₈O₇+H)⁺):
Calcd : 651.3255.
Found : 651.3235.
¹H-NMR(300 MHz,DMSO-d₆,δ ppm):0.65(3H,d,J=6.5Hz),
0.75(3H,d,J=6.5Hz),0.79(3H,d,J=6.6Hz),0.83(3H,d,J=6.6Hz),0.94-1.08(1H,m),1.19-1.24(2H,m),1.72-1.85(1H, m),2.37-2.50(1H,m),2.63-2.77(2H,m),2.81-2.93(1H,m),
3.04(1H,dd,J=6.5Hz,15.4Hz),3.10-3.51(1H,m),4.01-4.-

10(1H,m),4.17(1H,dd,J=6.6Hz,9.2Hz),4.30–4.39(1H,m),4.48–4.57(1H,m),4.63–4.72(1H,m),6.95–7.07(3H,m),7.11(1H,d,J=1.8Hz),7.31(1H,d,J=8.0Hz),7.34(1H,d,J=9.3Hz),7.52(1H,d,J=8.0Hz),7.64(1H,d,J=7.0Hz),8.12(1H,brs),8.64(1H,d,J=5.3Hz),8.72(1H,d,J=8.7Hz),8.90(1H,d,J=7.8Hz),10.79(1H,brs).

EXAMPLE 19 cyclo(-DTrp-DAsp-Arg-DVal-Leu-).TFA salt m.p. 235° C.(dec.).
IR(KBr,cm$^{-1}$):
3352,2968,1668,1536,1203,1140,836,798,742.
High Resolution FAB-MS(m/e,($C_{32}H_{47}N_9O_7$+H)$^+$):
Calcd : 670.3677.
Found : 670.3700.
$^1$H-NMR(300 MHz,DMSO-d$_6$,δ ppm):0.63(3H,d,J=6.3Hz),
0.74(3H,d,J=6.3Hz),0.80(3H,d,J=6.6Hz),0.82(3H,d,J=6.6Hz),0.93–1.07(1H,m),1.21(2H,t,J=6.8Hz),1.22–1.30(1H,m),1.37–1.60(2H,m),1.62–1.85(2H,m),2.38–2.45(1H,m),2.72(1H,dd,J=10.5Hz,16.2Hz),2.87(1H,dd,J=11.3Hz,4.2Hz),3.10–3.20(3H,m),4.05–4.11(1H,m),4.14(1H,dd,J=6.6Hz,9.4Hz),4.25–4.38(2H,m),4.48–4.56(1H,m),6.95(1H,t,J=7.3Hz),7.03(1H,t,J=7.3Hz),7.09(1H,d,J=2.4Hz),7.30(1H,d,J=7.3Hz),7.41(1H,d,J=9.4Hz),7.50(1H,d,J=7.3Hz),
7.58(1H,d,J=7.4Hz),8.59(1H,d,J=5.9Hz),8.68(2H,d,J=8.1Hz),10.76 (1H,d,J=2.4Hz).

EXAMPLE 20 cyclo(-DTrp-DAsp-Orn-DVal-Leu-)

m.p.: 219° C.(dec.).
IR(KBr,cm$^{-1}$):
3418,3058,2968,1668,1539,1392,1206,1182.
High Resolution FAB-MS(m/e,($C_{31}H_{45}N_7O_7$+H)$^+$):
Calcd : 628.3459.
Found : 628.3448.
$^1$H-NMR(300 MHz,DMSO-d$_6$,δ ppm):0.64(3H,d,J=6.4Hz),
0.74(3H,d,J=6.3Hz),0.80–0.84(6H,m),0.93–1.08(1H,m),1.17–1.23(2H,m),1.45–1.65(2H,m),1.71–1.86(1H,m),2.42–2.50(1H,m),2.64–2.80(3H,m),2.87(1H,dd,J=10.9Hz,11.4Hz),3.20–3.30(1H,m),3.40–3.50(2H,m),4.06(1H,dt,J=6.0Hz,7.5Hz),4.14(1H,dd,J=6.6Hz,9.6Hz),4.24–4.41(2H,m),
4.45–4.55(1H,m),6.95(1H,dt,J=1.2Hz,8.0Hz),7.04(1H,dt,J=1.2Hz,8.0Hz),7.09(1H,d,J=1.8Hz),7.30(1H,d,J=8.0Hz),
7.38(1H,d,J=9.0Hz),7.50(1H,d,J=8.0Hz),7.60(1H,d,J=6.6Hz),8.60(1H,d,J=6.0Hz),8.68(1H,d,J=8.1Hz),8.68(1H, d,J=8.1Hz),10.78(1H,d,J=1.8Hz).

EXAMPLE 21 cyclo(-DTrp-nAsp-Gln-DVal-Leu-)

m.p.: 270° C.(dec.).
IR(KBr,cm$^{-1}$): 3412,2962,1665,1539,1230,1173,1095.
High Resolution FAB-MS(m/e,($C_{31}H_{43}N_7O_8$+H)$^+$):
Calcd : 642.3252.
Found : 642.3218.
$^1$H-NMR(300 MHz,DMSO-d$_6$,δ ppm):0.64(3H,d,J=6.5Hz),
0.75(3H,d,J=6.5Hz),0.80–0.89(6H,m),0.91–1.11(1H,m),1.15–1.30(2H,m),1.61–1.95(3H,m),2.01–2.11(2H,m),2.44–2.50(1H,m),2.72(1H,dd,J=9.8Hz,16.2Hz),2.88(1H,dd,J=11.3Hz,14.6Hz),3.19–3.41(1H,m),4.01(1H,dd,J=7.6Hz,14.2Hz),4.17(1H,dd,J=6.5Hz,9.3Hz),4.24–4.38(2H,m),4.49–4.59(1H,m),6.72(1H,brs),6.96(1H,t,J=7.5Hz),7.04(1H,t,J=7.5Hz),7.11(1H,d,J=1.8Hz),7.12(1H,brs),7.31(1H,d,J=7.5Hz),7.35(1H,d,J=9.5Hz),7.52(1H,d,J=7.5Hz),
7.57(1H,d,J=7.6Hz),8.63(1H,d,J=6.2Hz),8.71(1H,d,J=9.3Hz),8.74(1H,d,J=9.5Hz),10.78(1H,brs).

EXAMPLE 22 cyclo(-DTrp-DAsp-Asp-DVal-Leu-)

m.p.: 265° C.(dec.).
IR(KBr,cm$^{-1}$): 3442,3292,2962,1647,1551,1395.
High Resolution FAB-MS(m/e,($C_{30}H_{40}N_6O_9$+H)$^+$):
Calcd : 629.2935.
Found : 629.2946.
$^1$H-NMR(300 MHz,DMSO-d$_6$,δ ppm):0.64(3H,d,J=6.4Hz),0.75(3H,d,J=6.4Hz),0.81(3H,d,J=6.4Hz),0.83(3H,d,J=6.4Hz),0.92–1.10(1H,m),1.16–1.28(2H,m),1.69–1.87(1H,m),2.22–2.46(2H,m),2.61–2.96(3H,m),3.22–3.41(1H,m),
4.01–4.13(1H,m),4.13–4.23(1H,m),4.27–4.39(1H,m),4.49–4.62(1H,m),4.62–4.78(1H,m),6.96(1H,t,J=7.8Hz),7.04(1H,t,J=7.8Hz),7.11(1H,d,J=1.8Hz),7.31(2H,d,J=7.8Hz),7.52,d,J=7.8Hz),7.50–7.67(1H,m),8.61–8.72(1H,m),8.76(1H,d,J=8.5Hz),8.84–8.98(1H,m),10.78(1H,brs).

EXAMPLE 23 cyclo(-DTrp-DAsp-Glu-DVal-Leu-)

m.p.: 271° C.(dec.).
IR(KBr,cm$^{-1}$):
3298,3058,2968,1659,1539,1464,1395,1236, 1176,744.
FAB-MS(m/e,($C_{31}H_{42}N_6O_9$+H).):643.
$^1$H-NMR(300 MHz,DMSO-d$_6$,δ ppm):0.63(3H,d,J=6.6Hz),0.73(3H,d,J=6.3Hz),0.80(3H,d,J=7.6Hz),0.82(3H,d,J=7.1Hz),0.90–1.08(1H,m),1.20(2H,t,J=7.2Hz),1.62–1.98(3H,m),2.12–2.38(2H,m),2.49(1H,dd,J=3.7Hz,16.4Hz),
2.71(1H,dd,J=10.5Hz,16.4Hz),2.87(1H,dd,J=11.2Hz,14.4Hz),3.28(1H,dd,J=2.9Hz,14.4Hz),4.04(1H,dt,J=6.3Hz,7.2Hz),4.16(1H,dd,J=6.6Hz,9.4Hz),4.26–4.38(2H,m),4.53(1H,ddd,J=3.7Hz,6.9Hz,10.5Hz),6.95(1H,t,J=7.2Hz),7.03(1H,t,J=7.2Hz),7.09(1H,d,J=1.8Hz),7.30(1H,d,J=7.2Hz),
7.33(1H,d,J=9.4Hz),7.50(1H,d,J=7.2Hz),7.54(1H,d,J=6.9Hz),8.63(1H,d,J=6.3Hz),8.70(1H,d,J=8.5Hz),8.76(1H, d,J=8.1Hz),10.77(1H,d,J=1.8Hz),12.18(2H,brs).

EXAMPLE 24 cyclo(-DTrp-DAsp-Cys(O$_3$Na)-DVal-Leu-)

m.p.: 281° C.(dec.).
IR(KBr,cm$^{-1}$):3418,3280,2962,1665,1584,1545,1206,1047.
High Resolution FAB-MS(m/e,($C_{29}H_{39}N_6NaO_{10}S$+H)$^+$):

Calcd : 687.2424.
Found : 687.2468.
$^1$H-NMR(300 MHz,DMSO-$d_6$,δ ppm):0.65(3H,d,J=6.5Hz),0.75(3H,d,J=6.5Hz),0.83(3H,d,J=6.7Hz),0.84(3H,d,J=6.7Hz),1.00-1.10(1H,m),1.15-1.30(2H,m),1.75-1.85(1H,m),2.28(1H,dd,J=3.4Hz,15.7Hz),2.45-2.65(2H,m),2.87(1H,dd,J=2.2Hz,12.0Hz),3.15-3.40(2H,m),4.11(1H,q,J=6.9Hz),4.17(1H,dd,J=6.4Hz,9.4Hz),4.25-4.35(1H,m),4.45-4.55(1H,m),4.60(1H,q,J=7.0Hz),6.98(1H,t,J=7.6Hz),7.04(1H,t,J=7.6Hz),7.12(1H,d,J=2.0Hz),7.31(1H,d,J=7.6Hz),7.38(1H,d,J=9.4Hz),7.53(1H,d,J=7.6Hz),7.50-7.60(1H,m),8.66(1H,d,J=6.9Hz),8.66(1H,d,J=8.8Hz),8.72 (1H,d, J=7.0Hz),10.77(1H,d,J=2.0Hz).

EXAMPLE 25 cyclo(-DTrp-DAsp-Cys-DVal-Leu-)

m.p.: 245° C.(dec.).
High Resolution FAB-MS(m/e,($C_{29}H_{40}N_6O_7S$+H)$^+$):
Calcd : 617.2758.
Found : 617.2762.
$^1$H-NMR(300 MHz,DMSO-$d_6$,δ ppm):0.65(3H,d,J=6.5Hz),0.75(3H,d,J TM 6.5Hz),0.83(3H,d,J=6.7Hz),0.84(3H,d,J=6.7Hz),0.95-1.10(1H,m),1.21(2H,t,J=7.4Hz),1.75-1.90(1H,m),2.23(1H,dd,J=7.6Hz,9.3Hz),2.45-2.60(2H,m),2.70-2.80(2H,m),2.88(1H,dd,J=11.2Hz,14.4Hz),3.25-3.35(1H,m),4.07(1H,dt,J=6.7Hz,7.4Hz),4.17(1H,dd,J=6.9Hz,9.6Hz),4.32(1H,ddd,J=3.3Hz,8.1Hz,11.2Hz),4.40(1H,q,J=7.6Hz),4.50-4.60(1H,m),6.96(1H,t,J=6.8Hz),7.04(1H,t,J=6.8Hz),7.11(1H,d,J=2.2Hz),7.31(1H,d,J=6.8Hz),7.33(1H,d,J=9.6Hz),7.52(1H,d,J=6.8Hz),7.63(1H,d,J=7.4Hz),
8.62(1H,d,J=6.7Hz),8.69(1H,d,J=8.1Hz),8.80(1H,d,J=7.6Hz),10.79(1H,d,J=2.2Hz).

EXAMPLE 26 cyclo(-DTrp-DAsp-Ser-DVal-Leu-)

m.p.: 250° C.(dec.).
IR(KBr,cm$^{-1}$):3286,2960,2930,1647,1551.
High Resolution FAB-MS(m/e,($C_{29}H_{40}N_6O_8$+H)$^+$):
Calcd : 601.2986.
Found : 601.3000.
$^1$H-NMR(300 MHz,DMSO-$d_6$,δ ppm):0.65(3H,d,J=6.6Hz),0.73(3H,d,J=6.4Hz),0.81-0.84(6H,m),1.05-1.13(1H,m), 1.15-1.25(2H,m),1.75-1.85(1H,m),2.30-2.56(1H,m),2.75(1H,dd,J=9.3Hz,16.2Hz),2.88(1H,dd,J=4.8Hz,15.3Hz), 3.16-3.25(1H,m),3.28-3.40(1H,m),3.72(1H,dd,J=7.2Hz,10.6Hz),3.98-4.16(2H,m),4.28-4.38(2H,m),4.45-4.55(1H,m),6.94(1H,dt,J=1.0Hz,8.0Hz),7.04(1H,dt,J=1.0Hz,8.0Hz),7.08(1H,d,J=1.8Hz),7.30(1H,d,J=8.0Hz),7.35(1H,d,J=9.3Hz),7.50(1H,d,J=8.0Hz),7.69(1H,d,J=7.1Hz),8.48(1H,d,J=8.1Hz),8.54(1H,d,J=6.4Hz),8.58(1H,d,J=8.2Hz),10.76(1H,d,J=1.8Hz).
Optical Rotations: $[\alpha]_D^{20}$= +1.2°(c 0.27, DMSO).

EXAMPLE 27 cyclo(-DTrp-DAsp-Thr-DVal-Leu-)

m.p.: >300° C.
IR(KBr,cm$^{-1}$):
3298,2968,1674,1653,1539,1464,1392,1224, 1179,741.

High Reolution FAB-MS(m/e,($C_{30}H_{42}N_6O_8$+H)$^+$):
Calcd : 615.3143.
Found : 615.3181.
$^1$H-NMR(300 MHz,DMSO-$d_6$,δ ppm):0.67(3H,d,J=6.7Hz),0.76(3H,d,J=6.7Hz),0.82(3H,d,J=6.7Hz),0.83(3H,d,J=6.7Hz),1.03(1H,d,J=6.4Hz),1.04-1.18(1H,m),1.20-1.36(2H,m),1.76-1.90(1H,m),2.42(1H,dd,J=4.7Hz,16.1Hz),
2.76(1H,dd,J=9.1Hz,16.1Hz),2.88(1H,dd,J=9.9Hz,14.7Hz),3.21(1H,dd,J=4.1Hz,14.7Hz),3.85-3.95(1H,m),3.99(1H,t,J=8.6Hz),4.11-4.20(2H,m),4.30-4.37(1H,m),4.39(1H,d,J=4.3Hz),4.48-4.57(1H,m),6.95(1H,t,J=7.9Hz),7.03,(1H,t,J=7.9Hz),7.08(1H,d,J=2.2Hz),7.30(1H,d,J=7.9Hz),7.51(1H,d,J=7.9Hz),7.59(1H,d,J=8.6Hz),7.78(1H,d,J=7.3Hz),
8.07(1H,d,J=8.3Hz),8.36(1H,d,J=8.1Hz),8.42(1H,d,J=6.8Hz),10.77(1H,d,J=2.2Hz),12.08(1H,brs).
Optical Rotations: $[\alpha]_D^{20}$= −8.5°(c 0.42, DMSO).

EXAMPLE 28 cyclo(-DTrp-DAsp-Ala-DLeu-Leu-)

m.p.: 245° C.(dec.).
IR(KBr,cm$^{-1}$): 3448,2950,1650,1542,1230.
High Resolution FAB-MS(m/e,($C_{30}H_{42}N_6O_7$+H)$^+$):
Calcd : 599.3193.
Found : 599.3218.
$^1$H-NMR(300 MHz,DMSO-$d_6$,δ ppm):0.65(3H,d,J=6.3Hz),0.75(3H,d,J=6.3Hz),0.86(3H,d,J=6.6Hz),0.87(3H,d,J=6.6Hz),0.85-1.05(1H,m),1.12(3H,d,J=6.8Hz),1.15-1.60(5H,m),2.35-2.55(1H,m),2.68-2.78(1H,m),2.87(1H,dd,J=10.8Hz,14.3Hz),3.15-3.40(1H,m),4.00-4.10(1H,m),4.31-4.57(4H,m),6.96(1H,t,J=7.4Hz),7.04(1H,t,J=7.4Hz),7.10(1H,d,J=2.2Hz),7.31(1H,d,J=7.4Hz),7.36(1H,d,J=9.5Hz),
7.51(1H,d,J=7.4Hz),7.67(1H,d,J=7.6Hz),8.60-8.68(3H,m),0.79(1H,brs).

EXAMPLE 29 cyclo(-DTrp-DAsp-Ala-DThr-Leu-)

m.p.: 230° C.(dec.).
IR(KBr,cm$^{-1}$):3322,2968,1668,1539,1236,1179.
High Resolution FAB-MS(m/e,($C_{28}H_{38}N_6O_8$+H)$^+$):
Calcd : 587.2830.
Found : 587.2834.
$^1$H-NMR(300 MHz,DMSO-$d_6$,δ ppm):0.63(3H,d,J=6.3Hz),0.75(3H,d,J=6.3Hz),0.90-0.99(1H,m),1.01(3H,d,J=6.1Hz),
1.13(3H,d,J=7.1Hz),1.10-1.32(2H,m),2.40-2.60(1H,m),2.74(1H,dd,J=10.7Hz,16.2Hz),2.86(1H,dd,J=11.6Hz,14.9Hz),3.20-3.63(2H,m),3.70-3.80(1H,m),3.94-4.04(1H,m),
4.23(1H,dd,J=4.5Hz,9.5Hz),4.30-4.40(1H,m),4.43-4.60(2H,m),6.95(1H,t,J=7.3Hz),7.04(1H,t,J=7.3Hz),7.09(1H,d,J=1.8Hz),7.23(1H,d,J=9.5Hz),7.31(1H,d,J=7.3Hz),7.51(1H,d,J=7.3Hz),7.78(1H,d,J=7.1Hz),8.57(1H,d,J=5.9Hz),8.68(1H,d,J=9.9Hz),8.79(1H,d,J=8.0Hz),10.78(1H,d,J=1.8Hz).

EXAMPLE 30 cyclo(-DTrp-DAsp-Pro-DVal-Leu-)

m.p.: 175°-180° C.
IR(KBr,cm$^{-1}$):3424,2950,1668,1536,1458.

FAB-MS(m/e,($C_{29}H_{38}N_6O_7$+H)$^+$):583.
$^1$H-NMR(300 MHz,DMSO-$d_6$,δ ppm):0.58(3H,d,J=6.6Hz),0.71(3H,d,J=6.4Hz),0.75-0.95(1H,m),1.10-1.30(2H,m),
1.11(3H,d,J=6.7Hz),1.51-1.70(1H,m),1.70-1.98(2H,m),2.14-2.24(1H,m),2.34(1H,dd,J=4.1Hz,16.1Hz),2.79(1H,dd,J=10.0Hz,16.1Hz),2.88(1H,dd,J=11.5Hz,14.4Hz),3.03-3.22(1H,m),3.20-3.40(2H,m),3.87-3.99(1H,m),4.28(1H,ddd,J=3.2Hz,8.0Hz,11.5Hz),4.45(1H,dq,J=6.7Hz,10.0Hz),
4.69(1H,d-like,J=7.3Hz),4.93(1H,dt,J=4.1Hz,10.0Hz),6.95(1H,t,J=7.7Hz),7.04(1H,t,J=7.7Hz),7.12(1H,d,J=2.2Hz),7.31(1H,d,J=7.7Hz),7.46(1H,d,J=10.0Hz),7.50(1H,d,J=7.7Hz),7.78(1H,d,J=10.0Hz),8.62(1H,d,J=5.3Hz),8.67(1H,d,J=8.0Hz),10.80(1H,d,J=2.2Hz).

EXAMPLE 31 cyclo(-DTrp-DAsp-Pro-DIle-Leu-)

m.p.: 149°-153° C.
IR(KBr,cm$^{-1}$):
3322,2962,1656,1536,1461,1392,1344,1236, 1173,1098.
High Resolution FAB-MS(m/e,($C_{32}H_{44}N_6O_7$+H)$^+$):
Calcd : 625.3350.
Found : 625.3365.
$^1$H-NMR(300 MHz,DMSO-$d_6$,δ ppm):0.61(3H,d,J=6.3Hz),0.74(3H,d,J=6.4Hz),0.74-0.91(6H,m),0.96-1.22(4H,m),
1.41-1.55(1H,m),1.54-1.70(1H,m),1.70-1.85(1H,m),1.86-1.98(2H,m),2.10-2.20(1H,m),2.32(1H,dd,J=4.0Hz,16.0Hz),2.77(1H,dd,J=9.5Hz,16.0Hz),2.89(1H,dd,J=11.2Hz,14.4Hz),3.20-3.30(1H,m),3.30-3.40(2H,m),3.95-4.12(1H,m),
4.10-4.29(2H,m),4.75(1H,d-like,J=6.9Hz),4.94(1H,ddd,J=5.0Hz,9.0Hz,9.0Hz),6.96(1H,dt,J=1.0Hz,8.0Hz),7.04(1H,dt,J=1.0Hz,8.0Hz),7.14(1H,d,J=2.1Hz),7.31(1H,d,J=8.0Hz),7.49(1H,d,J=10.2Hz),7.50(1H,d,J=8.0Hz),7.63(1H,d,J=9.0Hz),8.78(1H,d,J=6.5Hz),8.79(1H,d,J=6.5Hz),10.80(1H,d,J=2.1Hz).

EXAMPLE 32 cyclo(-DTrp-DAsp-Pro-DaIle-Leu-)

m.p.: 190° C.(dec.).
IR(KBr,cm$^{-1}$):3448,2968,1659,1536,1461.
High Resolution FAB-MS(m/e,($C_{32}H_{44}N_6O_7$+H)$^+$):
Calcd : 625.3350.
Found : 625.3309.
$^1$H-NMR(300 MHz,DMSO-$d_6$,δ ppm):0.59(3H,d,J=6.3Hz),0.72(3H,d,J=6.3Hz),0.80-0.91(6H,m),0.87-1.06(1H,m),
0.97-1.40(4H,m),1.40-1.58(1H,m),1.53-1.71(1H,m),1.67-1.87(1H,m),1.85-2.00(1H,m),2.22-2.31(1H,m),2.32(1H,dd,J=4.0Hz,17.0Hz),2.76(1H,dd,J=6.2Hz,17.0Hz),2.89(1H,t,J=13.4Hz),3.05-3.60(3H,m),3.92-4.03(1H,m),4.22-4.35(2H,m),4.75(1H,d-like,J=7.4Hz),4.90-5.03(1H,m),6.95(1H,t,J=7.4Hz),7.04(1H,t,J=7.4Hz),7.13(1H,d,J=1.7Hz),7.31(1H,d,J=7.4Hz),7.50(1H,d,J=7.9Hz),7.51(1H,d,J=7.4Hz),7.73(1H,d,J=9.1Hz),8.78(1H,d,J=6.1Hz),8.78(1H, d,J=6.1Hz),10.80(1H,d,J=1.7Hz).

EXAMPLE 33 cyclo(-DTrp-DAsp-Pro-DNle-Leu-)

m.p.: 159°-165° C.
IR(KBr,cm$^{-1}$):3442,2962,1656,1539,1455.
High Resolution FAB-MS(m/e,($C_{32}H_{44}N_6O_7$+H)$^+$):
Calcd : 625.3350.
Found : 625.3341.
$^1$H-NMR(300 MHz,DMSO-$d_6$,δ ppm):0.59(3H,d,J=6.4Hz),0.71(3H,d,J=6.3Hz),0.82(3H,t,J=6.9Hz),0.90-1.03(1H,m),
2.00(2H,m),2.19-2.29(1H,m),2.33(1H,dd,J=4.1Hz,15.8Hz)
2.78(1H,dd,J=9.1Hz,15.8Hz),2.89(1H,dd,J=11.4Hz,14.6Hz),3.13(1H,dt,J=2.5Hz,9.0Hz),3.20-3.60(2H,m),3.95(1H,q,J=5.3Hz),4.26(1H,ddd,J=5.1Hz,8.6Hz,11.4Hz),4.36(1H,q,J=10.3Hz),4.72(1H,d-like,J=7.4Hz),4.95(1H,dt,J=4.1Hz,9.1Hz),6.95(1H,t,J=8.1Hz),7.03(1H,t,J=8.1Hz),7.13(1H,d,J=2.2Hz),7.31(1H,d,J=8.1Hz),7.43(1H,d,J=10.3Hz),
7.50(1H,d,J=8.1Hz),7.73(1H,d,J=9.1Hz),8.73(1H,d,J=5.3Hz),8.75(1H,d,J=8.6Hz),10.80(1H,d,J=2.2Hz).

EXAMPLE 34 cyclo(-DTrp-DAsp-Pro-DPhg-Leu-)

185°-189° C.
IR(KBr,cm$^{-1}$): 3310,3058,2962,1665,1536,1458,1233.
High Resolution FAB-MS(m/e,($C_{34}H_{40}N_6O_7$+H)$^+$):
Calcd : 645.3036.
Found : 645.3015.
$^1$H-NMR(300 MHz,DMSO-$d_6$,δ ppm):0.56(3H,d,J=6.6Hz),0.69(3H,d,J=6.4Hz),0.76-0.95(1H,m),1.10-1.35(2H,m),
1.58-1.75(1H,m),1.75-1.90(1H,m),1.85-2.04(1H,m),2.23-2.40(1H,m),2.37(1H,dd,J=4.1Hz,16.4Hz),2.83(1H,dd,J=8.6Hz,16.4Hz),2.89(1H,dd,J=11.6Hz,14.7Hz),3.05(1H,m), 8.1Hz,14.7Hz),4.83(1H,d-like,J=7.0Hz),5.00(1H,dt,J=4.1Hz,8.6Hz),5.63(1H,d,J=10.3Hz),6.95(1H,t,J=7.6Hz),
7.03(1H,t,J=7.6Hz),7.11(1H,d,J=1.8Hz),7.26-7.45(6H,m),7.50(1H,d,J=7.6Hz),7.70(1H,d,J=8.6Hz),8.19(1H,d,J=0.3Hz),8.76(1H,d,J=8.1Hz),9.09(1H,d,J=5.4Hz),10.80(1H,d,J=1.8Hz).

EXAMPLE 35 cyclo(-DTrp-DAsp-Pro-DNva-Leu-)

m.p.: 156° C.(dec.).
IR(KBr,cm$^{-1}$):
3322,2962,1668,1536,1461,1242,1203,745.
High Resolution FAB-MS(m/e,($C_{31}H_{42}N_6O_7$+H)$^+$):
Calcd : 611.3193.
Found : 611.3193.
$^1$H-NMR(300 MHz,DMSO-$d_6$,δ ppm):0.59(3H,d,J=6.3Hz),0.71(3H,d,J=6.3Hz),0.86(3H,d,J=7.2Hz),0.85-1.02(1H,m),
1.14-1.36(4H,m),1.37-1.49(2H,m),1.52-1.98(3H,m),2.18-2.27(1H,m),2.33(1H,dd,J=4.0Hz,16.2Hz),2.78(1H,dd,J=10.3Hz,16.2Hz),2.89(1H,dd,J=11.4Hz,14.6Hz),2.99-3.07(1H,m),3.14-3.29(1H,m),3.23(1H,dd,J=2.7Hz,14.6Hz),
3.95(1H,dt,J=6.0Hz,7.0Hz),4.27(1H,ddd,J=2.7Hz,7.6Hz, 11.4Hz),4.39(1H,dt,J=10.2Hz,8.0Hz),4.72(1H,d-like,J=7.0Hz),4.96(1H,ddd,J=4.0Hz,7.7Hz,10.3Hz),6.95(1H,t,J=7.6Hz),7.04(1H,t,J=7.6Hz),7.13(1H,d,J=1.9Hz),7.30(1H,d,J=7.6Hz),7.42(1H,d,J=10.2Hz),7.50(1H,d,J=

7.6Hz),7.73(1H,d,J=7.7Hz),8.73(1H,d,J=7.6Hz),8.74(-1H,d,J=6.0Hz),10.79(1H,d,J=1.9Hz),12.30(1H,brs).
Optical Rotations: $[\alpha]_D^{20}=+64.9°$(c 0.45, MeOH).

EXAMPLE 36 cyclo(-DTrp-DAsp-Ser-DVal-Nle-)

m.p.: 235° C.(dec.).
IR(KBr,cm$^{-1}$):
3286,3060,2962,1647,1554,1460,1385,1225, 1172,1059.
High Resolution FAB-MS(m/e,($C_{29}H_{40}N_6O_8$+H)$^+$):
Calcd : 601.2986.
Found : 601.3005.
$^1$H-NMR(300 MHz,DMSO-d$_6$,δ ppm):0.72(3H,t,J=7.1Hz),0.83(3H,d,J=6.7Hz),0.84(3H,d,J=6.7Hz),0.85-1.18(4H,m), 1.32-1.43(2H,m),1.75-1.93(1H,m),2.43(1H,dd,J=4.2Hz,16.5Hz),2.73(1H,dd,J=9.6Hz,16.5Hz),2.88(1H,dd,J=10.8Hz,14.7Hz),3.18-3.42(2H,m),3.68-3.80(1H,m),3.93-4.06 (1H,m),4.12(1H,dd,J=7.3Hz,8.9Hz),4.27-4.38(2H,m),4.45-4.53(1H,m),4.66(1H,t,J=5.6Hz),6.96(1H,t,J=7.1Hz),7.04(1H,t,J=7.1Hz),7.11(1H,d,J=1.4Hz),7.30(1H,d,J=7.1Hz),7.40(1H,d,J=8.9Hz),7.53(1H,d,J=7.1Hz),7.74(1H,d,J=7.3Hz)88.44(1H,d,J=8.1Hz),8.50-8.57(2H,m),10.77(1H,d,J=1.4Hz).

EXAMPLE 37 cyclo(-DTrp-DAsp-Ser-DVal-Met-)

m.p.: 275° C.(dec.).
IR(KBr,cm$^{-1}$):3298,2975,1650,1542,1238.
High Resolution FAB-MS(m/e,($C_{28}H_{38}N_6O_8S$+H)$^+$):
Calcd : 619.2550.
Found : 619.2530.
$^1$H-NMR(300 MHz,DMSO-d$_6$,δ ppm):0.83(6H,d,J=6.6Hz),1.49-1.73(2H,m),1.73-1.89(1H,m),1.91(3H,s),1.91-2.07(1H,m),2.17-2.30(1H,m),2.38(1H,dd,J=4.7Hz,16.1Hz),2.76(1H,dd,J=9.1Hz,16.1Hz),2.88(1H,dd,J=10.0Hz,14.9Hz),3.23(1H,dd,J=3.2Hz,14.9Hz),3.28-3.45(1H,m),3.65-3.73(1H,m),4.07(1H,t,J=9.1Hz),4.15(1H,q,J=6.4Hz),4.28-4.39(2H,m),4.40-4.51(1H,m),4.68(1H,t,J=5.6Hz),6.95(1H,t,J=8.0Hz),7.03(1H,t,J=8.0Hz),7.10(1H,d,J=1.9Hz),7.30(1H,d,J=8.0Hz),7.47(1H,d,J=9.1Hz),7.53(1H,d,J=8.0Hz),7.75(1H,d,J=7.3Hz),8.32(1H,d,J=8.4Hz),8.51(1H,d,J=8.5Hz),8.61(1H,d,J=6.4Hz),10.79(1H,d,J=1.9Hz).

EXAMPLE 38 cyclo(-DTrp-DAsp-Asp-DVal-Ala-)

m.p.: 272° C.(dec.).
IR(KBr,cm$^{-1}$):
3292,2960,1668,1539,1461,1390,1341,1235, 1181,740.
High Resolution FAB-MS(m/e,($C_{27}H_{34}N_6O_9$+H)$^+$):
Calcd : 587.2466.
Found : 587.2461.
$^1$H-NMR(300 MHz,DMSO-d$_6$,δ ppm):0.81(3H,d,J=6.8Hz),0.84(3H,d,J=6.8Hz),0.99(3H,d,J=6.7Hz),1.77-1.90(1H,m), 2.31(1H,dd,J=4.6Hz,16.6Hz),2.41(1H,dd,J=3.9Hz,16.6Hz),2.70(1H,dd,J=9.8Hz,16.6Hz),2.80(1H,dd,J=9.9Hz,16.6Hz), 2.92(1H,dd,J=10.9Hz,14.9Hz),3.20-3.30(1H,m),4.10-4.19(1H,m),4.19(1H,dd,J=6.8Hz,10.1Hz),4.25-4.36(1H,m), 4.49-4.57(1H,m),4.63-4.76(1H,m),6.97(1H,t,J=7.8Hz),7.05(1H,t,J=7.8Hz),7.12(1H,d,J=1.8Hz),7.28(1H,d,J=0.1Hz),7.31(1H,d,J=7.8Hz),7.54(1H,d,J=7.8Hz),7.69(1H,d,J=7.3Hz),8.68(1H,d,J=10.9Hz),8.72(1H,d,J=8.2Hz),8.87(1H,d,J=8.1Hz),10.79(1H,d,J=1.8Hz).

EXAMPLE 39 cyclo(-DTrp-DAsp-Ala-DVal-Pro-)

m.p.: 186° C.(dec.).
IR(KBr,cm$^{-1}$):3424,2968,1671,1536,1449,1026.
High Resolution FAB-MS(m/e,($C_{28}H_{36}N_6O_7$+H)$^+$):
Calcd : 569.2724.
Found : 569.2737.
$^1$H-NMR(300 MHz,DMSO-d$_6$,δ ppm):0.84(3H,d,J=6.5Hz),0.89(3H,d,J=6.6Hz),1.11(3H,d,J=6.9Hz),1.57-1.73(2H,m), 1.73-2.10(3H,m),2.30-2.45(1H,m),2.45-2.60(1H,m),2.96(1H,dd,J=4.1Hz,10.5Hz),3.01-3.30(1H,m),3.47-3.60(2H,m),4.20-4.30(1H,m),4.30-4.40(2H,m),4.40-4.52(2H,m),6.97(1H,dt,J=1.0Hz,8.0Hz),7.06(1H,dt,J=1.0Hz,8.0Hz), 7.12(1H,d,J=2.0Hz),7.31(1H,d,J=8.0Hz),7.49(1H,d,J=6.0Hz),7.52(1H,d,J=8.0Hz),7.75(1H,d,J=4.0Hz),8.47(1H,d,J=9.0Hz),8.76(1H,d,J=8.1Hz),10.80(1H,d,J=2.0Hz).

EXAMPLE 40 cyclo(-DTrp-DAsp-Pro-DVal-Ile-)

m.p.: 240° C.(dec.).
IR(KBr,cm$^{-1}$): 3430,2974,1656,1539,1458,1233.
High Resolution FAB-MS(m/e,($C_{31}H_{42}N_6O_7$+H)$^+$):
Calcd : 611.3193.
Found : 611.3206.
$^1$H-NMR(300 MHz,DMSO-d$_6$,δ ppm):0.14(3H,d,J=6.5Hz),0.61(3H,t,J=6.8Hz),0.73(3H,d,J=6.6Hz),0.77(3H,d,J=6.6Hz),0.90-1.04(1H,m),1.23-1.37(1H,m),1.40-2.05(5H,m),2.15-2.24(1H,m),2.30-2.45(1H,m),2.50-2.65(1H,m), 2.70-2.85(1H,m),3.00-3.50(3H,m),3.67(1H,dd,J=7.1Hz,0.7Hz),4.05(1H,t,J=8.8Hz),4.15-4.25(1H,m),4.58(1H, d-like,J=7.1Hz),4.80-4.90(1H,m),6.87(1H,t,J=7.2Hz),6.95(1H,t,J=7.2Hz),7.08(1H,d,J=1.9Hz),7.13(1H,brs), 7.21(1H,d,J=7.2Hz),7.43(1H,d,J=7.2Hz),7.87(1H,d,J=9.6Hz),8.60-8.67(2H,m),10.71(1H,d,J=1.9Hz).
Optical Rotations: $[\alpha]_D^{20}=+32.0°$(c 0.26, MeOH).

EXAMPLE 41 cyclo(-DTrp-DAsp-Pro-DVal-Nle-)

IR(KBr,cm$^{-1}$):
3304,2968,1659,1536,1458,1233,1203,744.
High Resolution FAB-MS(m/e,($C_{31}H_{42}N_6O_7$+H)$^+$):
Calcd : 611.3193.
Found : 611.3198.
$^1$H-NMR(300 MHz,DMSO-d$_6$,δ ppm):0.68(3H,t,J=7.1Hz),0.83(3H,d,J=6.7Hz),0.87(3H,d,J=6.7Hz),0.90-1.43(4H,m), 1.53-2.00(4H,m),2.22-2.40(2H,m),2.78(1H,dd,J=10.5Hz,16.1Hz),2.90(1H,dd,J=11.6Hz,14.5Hz),3.08-3.40(3H,m), 3.83-3.94(1H,m),4.14(1H,dd,J=8.1Hz,9.9Hz),4.22-4.33(1H,m),4.76(1H,d-like,J=7.3Hz),4.95-5.06(1H,m),6.96(1H,t,J=7.6Hz),7.05(1H,t,J=7.6H- z),7.16(1H,d,J=2.5Hz),
7.31(1H,d,J=8.1Hz),7.49(1H,d,J=9.7Hz),7.52(1H,d,J=7.6Hz),7.72(1H,d,J=8.7Hz),8.71(1H,d,J=7.6Hz),8.78(1H,d,J=5.2Hz),10.78(1H,d,J=2.5Hz),12.29(1H,brs).

EXAMPLE 42 cyclo(-DTrp-DCys(O₃Na)-Cys(O₃Na)-DVal-Leu-)

m.p.: 286° C.(dec.).

IR(KBr,cm⁻¹): 3298,2968,1659,1545,1200,1050,741.

High Resolution FAB-MS(m/e,($C_{28}H_{40}N_6O_{11}S_2+H$)⁺):

Calcd : 701.2275.

Found : 701.2283.

FAB-MS(m/e,($C_{28}H_{38}N_6Na_2O_{11}S_2+H$)⁺):745.

¹H-NMR(300 MHz,DMSO-$d_6$,δ ppm):0.68(3H,d,J=6.3Hz),0.76(3H,d,J=6.3Hz),0.82(3H,d,J=6.7Hz),0.83(3H,d,J=6.7Hz),1.10-1.20(1H,m),1.27(2H,t,J=7.3Hz),1.85-1.95(1H,m),2.70-2.80(2H,m),2.84(1H,dd,J=11.0Hz,14.7Hz),3.07(1H,dd,J=5.5Hz,13.9Hz),3.15-3.40(2H,m),4.13(1H,dd,J=6.4Hz,9.3Hz),4.18(1H,q,J=7.3Hz),4.35-4.45(2H,m),
4.56(1H,q,J=7.5Hz),6.95(1H,t,J=6.9Hz),7.03(1H,t,J=6.9Hz),7.17(1H,d,J=2.1Hz),7.29(1H,d,J=6.9Hz),7.50(1H,d,J=9.3Hz),7.55(1H,d,J=6.9Hz),8.01(1H,d,J=7.4Hz),8.11(1H,d,J=8.5Hz),8.44(1H,d,J=7.3Hz),8.61(1H,d,J=7.5Hz),10.76(1H,d,J=2.1Hz).

EXAMPLE 43 cyclo(-DTrp-DCys(O₃Na)-Pro-DaIle-Leu-)

m.p.: 282° C.(dec.).

IR(KBr,cm⁻¹):3448,2962,1665,1535,1456,1220.

FAB-MS(m/e,($C_{31}H_{43}N_6NaO_8S+H$)⁺):683. ¹H-NMR(300 MHz,DMSO-$d_6$,δ ppm):0.61(3H,d,J=6.6Hz),0.71(3H,d,J=6.3Hz),0.80(3H,d,J=6.8Hz),0.84(3H,t,J=7.3Hz),0.87-1.16(2H,m),1.14-1.40(3H,m),1.41-1.70(2H,m),1.65-1.95(1H,m),2.12-2.28(1H,m),2.44-2.70(1H,m),
2.57(1H,dd,J=2.1Hz,13.4Hz),2.91(1H,dd,J=11.4Hz,14.2Hz),3.10-3.54(3H,m),3.65(1H,q,J=8.0Hz),4.11(1H,q,J=6.8Hz),4.17-4.32(2H,m),4.62(1H,d-like,J=6.2Hz),4.97(1H,m),6.95(1H,t,J=7.7Hz),7.03(1H,t,J=7.7Hz),7.12(1H,d,J=2.2Hz),7.22(1H,d,J=8.3Hz),7.30(1H,d,J=7.7Hz),7.52(1H,d,J=7.7Hz),8.09(1H,d,J=9.3Hz),8.59(1H,d,J=6.8Hz), 8.70(1H,d,J=8.5Hz),10.77(1H,d,J=2.2Hz).

According to the same procedure described in Example 6, each title compound described in the following Examples 44-50 was prepared from the corresponding Fmoc amino acids in which sidechain functional groups were protected with the appropriate protective groups, if necessary.

EXAMPLE 44 cyclo(-DTrp-DAsp-Val-DVal-Leu-)

m.p.: >300° C.

IR(KBr,cm⁻¹):3298,3064,2968,1644,1542,1392,1227.

High Resolution FAB-MS(m/e,($C_{31}H_{44}N_6O_7+H$)⁺):

Calcd : 613.3350.

Found : 613.3393.

¹H-NMR(300 MHz,DMSO-$d_6$,δ ppm):0.66(3H,d,J=6.3Hz),0.75(3H,d,J=6.3Hz),0.80-0.86(12H,m),1.00-1.12(1H,m),
1.20-1.25(2H,m),1.78-2.03(2H,m),2.48(1H,dd,J=4.5Hz,6.2Hz),2.72(1H,dd,J=10.1Hz,16.2Hz),2.89(1H,dd,J=10.5Hz,14.4Hz),3.23(1H,dd,J=3.4Hz,14.4Hz),3.93-3.99(1H,m),4.06-4.15(2H,m),4.28-4.35(1H,m),4.43-4.48(1H,m),6.96(1H,t,J=7.6Hz),7.04(1H,t,J=7.6Hz),7.10(1H,d,J=1.8Hz),7.31(1H,d,J=7.6Hz),7.45(1H,d,J=9.3Hz),7.53(1H,d,J=7.6Hz),
7.56(1H,d,J=7.1Hz),8.45(1H,d,J=6.8Hz),8.50(1H,d,J=8.5Hz),8.51(1H,d,J=8.4Hz),10.79(1H,d,J=1.8Hz),2.18(1H,brs).

Optical Rotations: $[\alpha]_D^{20} = -9.5°$(c 0.38, DMSO).

EXAMPLE 45 cyclo(-DTrp-DAsp-Pro-DVal-Nva-)

m.p.: 175°-176° C.

IR(KBr,cm⁻¹):3412,2968,1659,1539,1461.

Calcd : 597.3036.

Found 597.3052.

¹H-NMR(300 MHz,DMSO-$d_6$,δ ppm):0.63-0.98(2H,m),
0.67(3H,t,J=6.1Hz),0.82(3H,d,J=6.8Hz),0.86(3H,d,J=6.5Hz),1.24-1.32(2H,m),1.56-1.81(2H,m),1.86-1.96(1H,m),2.20-2.50(3H,m),2.77(1H,dd,J=10.7Hz,16.2Hz),2.89(1H,dd,J=11.5Hz,14.6Hz),3.23(1H,dd,J=3.3Hz,14.6Hz),3.35-3.42(2H,m),3.88-3.95(1H,m),4.13(1H,dd,J=8.3Hz,9.8Hz),4.26(1H,ddd,J=3.3Hz,8.2Hz,11.5Hz),4.75(1H,d-like,J=7.3Hz),4.92-5.00(1H,m),6.95(1H,t,J=7.2Hz),7.04(1H,t,J=7.2Hz),7.15(1H,d,J=1.5Hz),7.31(1H,d,J=7.2Hz),7.49(1H,d,J=8.3Hz),7.51(1H,d,J=7.2Hz),7.71(1H,d,J=8.7Hz),8.71(1H,d,J=8.2Hz),8.77(1H,d,J=4.9Hz),10.78(1H,d,J=1.5Hz).

Optical Rotations: $[\alpha]_D^{20} = +47.4°$(c 0.50, MeOH).

EXAMPLE 46 cyclo(-DTrp-DAsp-Nle-DVal-Leu-)

m.p.: >300° C.

IR(KBr,cm⁻¹) 3420,3286,2962,1644,1551.

High Resolution FAB-MS(m/e,($C_{32}H_{46}N_6O_7+H$)⁺):

Calcd : 627.3506.

Found : 627.3532.

¹H-NMR(300 MHz,DMSO-$d_6$,δ ppm):0.65(3H,d,J=6.5Hz),0.75(3H,d,J=6.5Hz),0.80-0.87(9H,m),0.97-1.07(1H,m), 1.19-1.24(6H,m),1.41-1.73(2H,m),1.75-1.85(1H,m),2.45-2.55(1H,m),2.73(1H,dd,J=10.2Hz,16.4Hz),2.88(1H,dd,J=11.3Hz,14.4Hz),3.20-3.40(1H,m),4.05-4.18(2H,m),4.26-4.34(2H,m),4.48-4.55(1H,m),6.96(1H,t,J=7.3Hz),7.04(1H,t,J=7.3Hz),7.10(1H,d,J=1.7Hz),7.31(1H,d,J=7.3Hz),7.40(1H,d,J=9.3Hz),7.52(1H,d,J=7.3Hz),7.58(1H,d,J=7.1Hz),
8.58(1H,d,J=6.4Hz),8.65(1H,d,J=5.9Hz),8.67(1H,d,J=6.1Hz),10.78(1H,d,J=1.7Hz),12.23(1H,brs).

Optical Rotations: $[\alpha]_D^{20} = -12.1°$(c 0.45, DMSO).

EXAMPLE 47 cyclo(-DTrp-DAsp-Pip-DVal-Leu-)

m.p.: 277° C.(dec.).

IR(KBr,cm⁻¹): 2962,1665,1536,1446,1392.

High Resolution FAB-MS(m/e,($C_{32}H_{44}N_6O_7+H$)⁺):

Calcd : 625.3350.

Found : 625.3396.

¹H-NMR(300 MHz,DMSO-d₆,δ ppm):0.61(3H,d,J=6.6Hz),0.72(3H,d,J=6.4Hz),0.83(6H,d,J=6.6Hz),0.96-1.04(1H,m), 1.14-1.25(2H,m),1.30-1.44(2H,m),1.46-1.71(3H,m),1.73-1.85(1H,m),1.88-1.96(1H,m),2.30(1H,dd,J=3.9Hz,16.0Hz),2.79(1H,dd,J=10.1Hz,16.0Hz),2.89(1H,dd,J=11.0Hz,15.1Hz),3.20-3.61(3H,m),3.96-4.02(1H,m),4.18(1H,dd,J=7.3Hz,10.0Hz),4.21-4.29(1H,m),5.03(1H,d-like,J=5.3Hz), 5.11(1H,ddd,J=3.9Hz,9.0Hz,10.1Hz),6.82(1H,d,J=10.0Hz), 6.95(1H,t,J=7.9Hz),7.04(1H,t,J=7.9Hz),7.14(1H,d,J=1.6Hz),7.31(1H,d,J=7.9Hz),7.51(1H,d,J=7.9Hz),7.73(1H,d,J=9.0Hz),8.79-8.83(2H,m),10.80(1H,d,J=1.6Hz),12.26(1H,brs).

EXAMPLE 48 cyclo(-DTrp-DAsp-Phe-DVal-Leu-)

IR(KBr,cm⁻¹):3298,3064,2962,1650,1539.
Calcd : 661.3350.
Found : 661.3354.
¹H-NMR(300 MHz,DMSO-d₆,δ ppm):0.66(3H,d,J=6.4Hz),0.74(3H,d,J=6.7Hz),0.76(3H,d,J=6.4Hz),0.81(3H,d,J=6.7Hz),0.97-1.13(1H,m),1.19-1.25(2H,m),1.75-1.83(1H,m),2.42(1H,dd,J=4.3Hz,16.2Hz),2.71(1H,dd,J=9.9Hz,16.2Hz),2.80(1H,dd,J=8.3Hz,14.8Hz),2.87(1H,dd,J=10.0Hz,14.8Hz),3.02(1H,dd,J=6.3Hz,14.4Hz),3.29(1H,dd,J=3.2Hz,14.4Hz),4.07-4.16(2H,m),4.31-4.38(1H,m),4.50-4.57(2H,m),6.96(1H,t,J=7.4Hz),7.05(1H,t,J=7.4Hz),7.10(1H,d,J=1.8Hz),7.13-7.29(5H,m),7.31(1H,d,J=7.4Hz),7.39(1H,d,J=9.5Hz),7.53(1H,d,J=7.4Hz),7.68(1H,d,J=7.3Hz),8.58(1H,d,J=6.4Hz),8.67(1H,d,J=8.5Hz),8.84(1H,d,J=8.1Hz), 10.79(1H,d,J=1.8Hz),12.15(1H,brs).
Optical Rotations: [α]$_D^{20}$= −14.0°(c 0.57, DMSO).

EXAMPLE 49 cyclo(-DTrp-DCys(O₃Na)-Glu-DVal-Leu-)

m.p.: 264° C.(dec.).
IR(KBr,cm⁻¹):3442,1686,1554,1443,1212,1140,726.
High Resolution FAB-MS(m/e,(C₃₀H₄₁N₆NaO₁₀S+Na)⁺):
Calcd : 723.2401.
Found : 723.2441.
¹H-NMR(300 MHz,DMSO-d₆,δ ppm):0.68(3H,d,J=6.3Hz),0.75(3H,d,J=6.4Hz),0.79(3H,d,J=6.9Hz),0.82(3H,d,J=6.9Hz),1.04-1.38(3H,m),1.60-1.98(3H,m),2.12-2.34(2H,m),2.79(1H,dd,J=3.5Hz,13.0Hz),2.90(1H,dd,J=10.7Hz, 14.7Hz),3.03(1H,dd,J=8.4Hz,13.0Hz),3.18(1H,dd,J=4.2Hz, 14.7Hz),4.00-4.31(4H,m),4.44(1H,ddd,J=3.5Hz,7.3Hz,8.4Hz),6.94(1H,t,J=7.6Hz),7.03(1H,t,J=7.6Hz),7.17(1H, d,J=1.7Hz),7.29(1H,d,J=7.6Hz),7.50(1H,d,J=7.6Hz),7.63(1H,d,J=7.4Hz),7.81(1H,d,J=9.0Hz),8.12(1H,d,J=7.0Hz),8.21(1H,d,J=7.8Hz),8.69(1H,d,J=7.6Hz),10.78(1H,d,J=1.7Hz),12.00(1H,brs).

EXAMPLE 50 cyclo(-DTrp-nCys(O₃H)-Lys-DVal-Leu-)

m.p.: 296° C.(dec.).
IR(KBr,cm⁻¹) 3298,3064,2962,1665,1536,1206,1041.
FAB-MS(m/e,(C₃₁H₄₇N₇O₈S+H)⁺):678.
¹H-NMR(300 MHz,DMSO-d₆,δ ppm):0.63(3H,d,J=6.0Hz),0.72(3H,d,J=6.4Hz),0.79(3H,d,J=6.5Hz),0.83(3H,d,J=6.5Hz),0.89-1.88(10H,m),2.80(1H,dd,J=2.9Hz,13.0Hz),2.90(1H,dd,J=11.5Hz,14.2Hz),3.12(1H,dd,J=9.2Hz,13.0Hz),3.18(1H,dd,J=8.4Hz,14.2Hz),3.20-3.35(2H,m),4.02-4.17(2H,m),4.20-4.34(2H,m),4.56(1H,ddd,J=2.9Hz,6.2Hz,9.2Hz),6.95(1H,t,J=7.3Hz),7.03(1H,t,J=7.3Hz),7.13(1H,d,J=2.0Hz),7.30(1H,d,J=7.3Hz),7.32(1H,d,J=6.2Hz),7.51(1H,d,J=7.3Hz),7.63(1H,d,J=9.2Hz),7.71(3H,brs),8.47(1H,d,J=6.5Hz),8.69(1H,d,J=8.1Hz),8.77(1H,d,J=8.4Hz),10.77(1H,d,J=2.0Hz).

EXAMPLE 51 cyclo(-DTrp(CHO)-DAsp-Pro-DVal-Leu-)

cyclo(-DTrp-DAsp-Pro-DVal-Leu-)(3.0 mg) which was prepared in Example 15, was dissolved in formic acid (0.5 ml). To the solution was introduced dry hydrogen chloride at room temperature with vigorous stirring until hydrogen chloride was saturated(ca. 15min). The reaction mixture was stirred at room temperature for additional 50 min and concentrated under reduced pressure. The residue was triturated with water(0.5 ml) to give the title compound(3.0 mg) as a pale yellow powder.

m.p.: 170° C.(dec.).
IR(KBr,cm⁻¹):3442,2962,1659,1536,1464,1392.
Calcd : 639.3143.
Found : 639.3109.
¹H-NMR(300 MHz,DMSO-d₆,δ ppm):0.52-0.60(3H,m),0.60-0.70(3H,m),0.83(3H,d,J=6.9Hz),0.86(3H,d,J=6.9Hz), 1.11-1.31(3H,m),1.55-1.83(3H,m),1.89-1.98(1H,m),2.22-2.31(1H,m),2.33-2.40(1H,m),2.71-3.30(5H,m),3.89-4.03(1H,m),4.14(1H,dd,J=8.1Hz,9.9Hz),4.38-4.48(1H,m),4.77(1H,d-like,J=7.1Hz),4.92-5.02(1H,m),6.91-7.60(4H,m),7.63(1H,d,J=8.1Hz),7.79(1H,d,J=8.4Hz),7.92-8.29(1H,m), 8.75-9.00(2H,m),9.25+9.64(1H,brs).

According to the same procedure described in Example 51, each title compound described in the following Examples 52-56 was prepared from the corresponding cyclic pentapeptide in which the tryptophanyl residue had an intact indole NH group.

EXAMPLE 52 cyclo(-DTrp(CHO)-DGlu-Ala-DaIle-Leu-)

m.p.: >300° C.
IR(KBr,cm⁻¹):3448,3286,2968,1644,1551,1467,1389.
High Resolution FAB-MS(m/e,(C₃₂H₄₄N₆O₈+H)⁺):
Calcd : 641.3299.
Found : 641.3279.
¹H-NMR(300 MHz,DMSO-d₆,δ ppm):0.58(3H,brs),0.63(3H,brs),0.76(3H,d,J=6.4Hz),0.85(3H,t,J=7.1Hz), 1.02-1.09(2H,m),1.12(3H,d,J=6.3Hz),1.22-1.31(3H,m),1.52-1.62(1H,m),1.82-1.96(2H,m),2.15(2H,t,J=7.7Hz, 15.4Hz),2.94(1H,dd,J=12.5Hz,14.1Hz),3.20-3.40(1H,m),3.95-4.03(1H,m),4.22-4.32(1H,m),4.31(1H,dd,J=5.5Hz, 7.6Hz),4.39-4.47(2H,m),7.28-7.36(2H,m),7.42(1H,d,J-

=5.5Hz),7.50-7.54(1H,m),7.57(1H,d,J=7.3Hz),7.63(1-H,d,J=7.3Hz),8.01+8.21(1H,brs),8.65(1H,d,J=5.3Hz-),8.76(1H, d,J=7.1Hz),8.89(1H,brs),9.25+9.62(1H,brs).

EXAMPLE 53 cyclo(-DTrp(CHO)-DAsp-Pro-DaIle-Leu-)

m.p.: 125°-135° C.
IR(KBr,cm$^{-1}$):
3280,2962,1695,1653,1464,1389,1050,1029, 1008,756.
High Resolution FAB-MS(m/e,(C$_{33}$H$_{44}$-N$_6$O$_8$+H)$^+$):
Calcd : 653.3299.
Found : 653.3311.
$^1$H-NMR(300 MHz,DMSO-d$_6$,δ ppm):0.45-0.65(5H,m),0.65-0.91(6H,m),1.01-1.1-3(1H,m),1.14-1.34(5H,m),1.41-1.54(1H,m),1.-55-1.68(1H,m),1.69-1.81(1H,m),1.87-1.97(1H,m),2.-22-2.32(1H,m),2.35-2.44(1H,m),2.81(1H,dd, J=9.8Hz,15.7Hz),2.93(1H,dd,J=12.7Hz,14.1Hz),3.03--3.20(2H,m),3.20-3.40(1H,m),
3.86-3.93(1H,m),4.29(1H,dd,J=6.6Hz,9.9Hz),4.-35-4.50(1H,m),4.77(1H,d-like,J=7.1Hz),
4.92-5.02(1H,m),7.-25-7.40(2H,m),7.48(1H,d,J=10.3Hz),7.56(1H,brs),7.62-(1H,d,J=7.8Hz),7.85(1H,d,J=8.8Hz),
8.01+8.21(1H,brs),8.81(1H,d,J=4.6Hz),8.92(1H,brs),9-.25+9.63(1H,brs),12.30(1H,brs).

EXAMPLE 54 cyclo(-DTrp(CHO)-DAsp-Ser-DVal-Nle-)

m.p.: 224° C.(dec.).
IR(KBr,cm$^{-1}$): 3286,2960,1644,1560,1467,1392,1236, 1073,750.
High Resolution FAB-MS(m/e,(C$_{30}$H$_{40}$-N$_6$O$_9$+Na)$^+$):
Calcd : 651.2754.
Found : 651.2748.
$^1$H-NMR(300 MHz,DMSO-d$_6$,δ ppm):0.64(3H,t,J=7.3Hz),0.80(3H,d,J=7.0Hz),0.85(3-H,d,J=7.0Hz),0.90-1.16(4H,m),
1.32-1.52(2H,m),1.88-2.05(1H,m),2.20-2-.35(1H,m),2.40-2.55(1H,m),2.85-3.20(2H,m),3.30-3.50(-1H,m),3.68-3.80(1H,m),4.03-4.54(4H,m),4.-55-4.70(1H,m),4.90-5.08(1H,m),7.29-7.42(2H,m),7.-60-7.80(3H,m),7.83-8.32(5H,m), 9.27+9.64(1H,brs).

EXAMPLE 55 cyclo(-DTrp(CHO)-DAsp-Met-DVal-Leu-)

m.p.: >300° C.
IR(KBr,cm$^-$):
3304,2962,1665,1539,1464,1392,1341,1233, 1180,796,756.
FAB-MS(m/e,(C$_{32}$H$_{44}$N$_6$O$_8$S+H)$^+$):673.
$^1$H-NMR(300 MHz,DMSO-d$_6$,δ ppm):0.58(3H,d,J=5.9Hz),0.63(3H,d,J=5.9Hz),0.79(3-H,d,J=6.6Hz),0.82(3H,d,J=6.6Hz),0.90-1.05(1H,m),1-.10-1.37(2H,m),1.72-1.95(3H,m),2.02(3H,s),2.-30-2.60(3H,m),2.73(1H,dd,J=10.5Hz, 16.3Hz),2.92(1H,dd,J=12.2Hz,14.2Hz),3.20-3.40(1H,-m),3.99(1H,dd,J=5.6Hz,8.5Hz),4.18(1H,dd,J=6.2Hz,-9.5Hz),
4.43-4.60(3H,m),7.27-7.38(3H,m),7.48-7.60(1H,m),7.6-2(2H,d,J=6.8Hz),8.01-8.22(1H,m),8.63-8.75(1H,m),8.-76-8.95(2H,m),9.25+9.63(1H,brs),12.30(1H,brs).

EXAMPLE 56 cyclo(-DTrp(CHO)-DAsp-Pro-DVal-Nva-)

m.p.: 170°-175° C.
IR(KBr,cm$^{-1}$): 3304,2968,1659,1539,1464 1392,1230,1182.
High Resolution FAB-MS(m/e,(C$_{31}$H$_{40}$-N$_6$O$_8$+H)$^+$):
Calcd : 625.2986.
Found : 625.2990.
$^1$H-NMR(300 MHz,DMSO-d$_6$,δ ppm):0.61(3H,brs),0.82(3H,d,J=6.8Hz),0.85(3H,d,J=6-.8Hz),1.26-1.34(2H,m),
1.57-1.81(3H,m),1.87-1.97(1H,m),2.22-2.28(2H,m),2.3-3-2.60(1H,m),2.37(1H,dd,J=3.5H-z,15.6Hz),2.80(1H,dd,J=10.3Hz,15.6Hz),2.93(1H,dd,J-=12.4Hz,13.6Hz),3.17(1H,dd,J=5.7Hz,-12.4Hz),3.45-3.68(2H,m),3.82-3.89(1H,m),4.13(1H,dd,-J=4.8Hz,10.1Hz),4.33-4.41(1H,m),4.76(1H,d-like,J=7-.4Hz),4.92-4.99(1H,m),7.29-7.37(2H,m),7.48(1H,d,J=-.10.1Hz),7.55-7.66(1H,m),7.63(1H,d,J=8.6Hz),7.79(1H-,d,J=8.6Hz),8.01+8.22(1H,brs),8.81(1H,d,J=5.1Hz),8-.78-8.94 (1H,m),9.26+9.64(1H,brs),12.30(1H,brs).

EXAMPLE 57 cyclo(-DTrp-DAsp-Lys(CHO)-DVal-Leu-)

To a solution of cyclo(-DTrp-DAsp-Lys-DVal-Leu-) (10.5 mg) which was prepared in Example 4, and formic pivalic anhydride(10 ml) in DMF(0. 5ml) was added TEA(10 μl). The reaction mixture was stirred at room temperature for 1 h and concentrated in vacuo. The residue was triturated with water (2 ml) to give the title compound(7.8 mg) as an off-white powder.
m.p.: 260° C.(dec.).
FAB-MS(m/e,(C$_{33}$H$_{47}$N$_7$O$_8$+H)$^+$):670.
$^1$H-NMR(300 MHz,DMSO-d$_6$,δ ppm):0.65(3H,d,J=6.5Hz),0.75(3H,d,J=6.5Hz),0.81(3-H,d,J=6.7Hz),0.83(3H,d,J=6.7Hz),0.95-1.85(10H,m),-2.45-2.55(1H,m),2.71(1H,dd,J=10.3Hz,16.4Hz),2.88(1-H,dd,J=11.3Hz,14.2Hz),2.98-3.10(2H,m),3.25-3.35(1-H,m),4.04-4.18(2H,m),4.23-4.36(2H,m),4.48-4.56(1H,-m),6.96(1H,t,J=7.5Hz),7.04(1H,t,J=7.5Hz),7.11(1H,s)-,7.31(1H,d,J=7.5Hz),7.40(1H,d,J=9.3Hz),7.52(1H,d,J-=7.5Hz),7.56(1H,d,J=6.8Hz),7.90-8.00(2H,m),8.59(1-H,d,J=5.9Hz),8.66(1H,d,J=7.8Hz),8.69(1H,d,J=8.4H-z),10.79(1H,s).
Optical Rotations: [α]$_D^{20}$=−11.8°(c 0.71, DMSO).

EXAMPLE 58 cyclo(-DTrp(CHO)-DAsp-Met(O)-DVal-Leu-)

To a solution of cyclo(-DTrp(CHO)-DAsp-Met-DVal-Leu-) (12.9 mg) which was prepared in Example 55 in acetic acid(2.0 ml) was added 35% H$_2$O$_2$(5 μl). The reaction mixture was stirred at room temperature for 3 h and concentrated under reduced pressure till the volume of the mixture was reduced to ca. 1 ml. The residue was triturated with water(3 ml) to give the title compound (7.6 mg) as a pale yellow powder.
m.p.: >300° C.
IR(KBr,cm$^{-1}$):
3448,2962,1668,1542,1464,1389,1341,1233, 1180,1020,756.
FAB-MS(m/e,(C$_{32}$H$_{44}$N$_6$O$_9$S+H)$^+$):689.
$^1$H-NMR(300 MHz,DMSO-d$_6$,δ ppm):0.58(3H,d,J=6.2Hz),0.62(3H,d,J=6.2Hz),0.80(3-H,d,J=6.6Hz),0.83(3H,d,J=6.6Hz),0.90-1.03(1H,m),1-

.10–1.28(2H,m),1.73–2.15(3H,m),2.-
40–2.59(1H,m),2.51(3H,s),2.60–2.81(3H,m),2.92(1H,
dd,J=11.0Hz,15.6Hz),3.20–3.40(1H,m),3.95–4.04(1H,-
m),4.14–4.23(1H,m),4.39–4.59(3H,m),7.27–7.43(3H,m),-
7.50–7.60(1H,m),7.-
61–7.75(2H,m),8.01+8.22(1H,brs),8.65–8.74(1H,m),8.-
77–8.97(2H,m),9.24+9.63(1H,brs),12.29(1H,brs).

EXAMPLE 59 cyclo(-DTrp-DAsp(ONa)-Pro-DVal-Leu-)

To a solution of Leu-OBzl.TsOH(70g) in dichloromethane(600 ml) was added successively N-methylmorpholine (19.5 ml), Boc-DVal(39 g), HOBT.H$_2$O(27 g) and EDCI.HCl(36 g) under ice cooling. The reaction mixture was stirred under ice cooling for 1h and at room temperature for 2 h, diluted with dichloromethane, washed successively with saturated NaHCO$_3$, 10% citric acid, water and saturated NaCl, dried over MgSO$_4$, and filtered. Solvents were rmmoved under reduced pressure to give Boc-DVal-Leu-OBzl (80 g) as a colorless oil. A solution of the oil(80 g) in methanol(400 ml) was added to a suspension of 10% Pd/C (2 g) in methanol(400 ml). The reaction mixture was stirred at room temperature under an atmosphere of hydrogen(under atmospheric pressure) for 12 h. The catalysts were filtered and the filtrate was concentrated under reduced pressure to give Boc-DVal-Leu(63 g) as a colorless oil. To a solution of Boc-nVal-Leu(62 g) in methanol(400 ml) was added water(120 ml) and cesium carbonate(31 g) at room temperature. The resulting mixture was concentrated in vacuo to give cesium salt, which was suspended in DMF(600 ml). To the suspension was added bromoacetophenone(38 g) at room temperature. The mixture was stirred for 1 h and the resulting white precipitate was filtered off. The filtrate was concentrated in vacuo and the residue was dissolved in EtOAc. The solution was washed successively with water, 4% NaHCO$_3$ and water, dried over Na$_2$SO$_4$, and filtered. The filtrate was concentrated under reduced pressure to give a crude yellow powder. The powder was recrystallized from hexane/EtOAc to give Boc-DVal-Leu-OPac(65 g) as colorless crystals. The crystals(11.3 g) were dissolved in TFA(70 ml) under ice cooling. The solution was stirred under ice cooling for 1 h and concentrated under reduced pressure. The residue was dissolved in dichloromethane(120 ml). To the solution was added successively N-methylmorpholine (7.8 ml), Boc-Pro(5.95 g), HOBT.H$_2$O(4.34 g) and EDCI.HCl (6.00 g) under ice cooling. The reaction mixture was stirred under ice cooling for 1 h and at room temperature for 2 h, diluted with dichloromethane, washed successively with saturated NaHCO$_3$, 10% citric acid, water and saturated NaCl, dried over MgSO$_4$, and filtered. The filtrate was concentrated under reduced pressure to give Boc-Pro-DVal-Leu-OPac(11.2 g) as a pale yellow, amorphous solid. The tripeptide(11.2 g) was dissolved in TFA (70 ml) under ice cooling. The solution was stirred under ice cooling for 30 min and concentrated under reduced pressure. The residue was dissolved in dichloromethane. N-Methylmorpholine(7.2 ml), Boc-DAsp(OBzl)(6.92 g), HOBT.-H$_2$O(3.14 g) and EDCI.HCl (4.31 g) was added to the dichloromethane solution under ice cooling and the resulting mixture was stirred under ice cooling for 1 h and at room temperature for 2 h, saturated NaHCO$_3$, 10% citric acid, water and saturated NaCl, dried over MgSO$_4$, and filtered. The filtrate was concentrated under reduced pressure to give Boc-DAsp(OBzl)-Pro-DVal-Leu-OPac(13.8 g) as a yellow oil. The oil(13.8 g) was dissolved in TFA(60 ml) under ice cooling. The solution was stirred under ice cooling for 30 min and concentrated under reduced pressure. The residue was dissolved in dichloromethane(100 ml). To the solution was added N-methylmorpholine(6.8 ml), Boc-DTrp(8.86 g), HOBT.H$_2$O(2.95 g) and EDCI.HCl(3.87 g) under ice cooling. The reaction mixtue was stirred under ice cooling for 1 h and at room temperature for 5 h, diluted with dichloromethane, washed successively with saturated NaHCO$_3$, 10% citric acid, water and saturated NaCl, dried over MgSO$_4$, and filtered. The filtrate was concentrated under reduced pressure to give the crude product which was purified by column chromatography on silica gel(WAKOGEL C-200) with chloroform/methanol(30/1) for elution to give Boc-DTrp-nAsp(OBzl)-Pro-DVal-Leu-OPac(16.1 g) as a colorless, amorphous solid. To a solution of the solid (16.1 g) in 90% acetic acid(400 ml) was added by portions zinc powder(30 g) under ice cooling and the mixture was stirred under ice cooling for 50 min and at room temperature for 30 min. The supernatant of the reaction mixture was separated from zinc dust by decantation and concentrated under reduced pressure. The residue was partitioned between 10% citric acid and EtOAc and the aqueous phase was extracted with EtOAc. The combined organic layers were dried over Na$_2$SO$_4$, filtered, and concentrated under reduced pressure to give a residual oil, which was triturated with petroleum ether. The resulting amorphous solid was dried in vacuo and dissolved in formic acid(200 ml) at room temperature. The reaction mixture was stirred at room tempertaure for 1.5 h and concentrated under reduced pressure. The residue was partitioned between water and chloroform. The aqueous phase was extracted with chloroform. The combined chloroform layers were dried over MgSO$_4$, filtered, and concentrated under reduced pressure. The residue was crystallized from ether to give DTrp-DAsp(OBzl)-Pro-DVal-Leu(13.6 g) as a pale yellow powder. A solution of the pentapeptide(13.3 g) in DMF (400 ml) was added dropwise over a period of 7 h to a solution of HOBT H$_2$O(4.13 g) and EDCI HCl(5.17 g) in DMF (800 ml) at room temperature. The reaction mixture was stirred at room temperature for 10.5 h, and concentrated in vacuo. The residue was purified by column chromatography on silica gel(WAKOGEL C-300) with dichloromethane/methanol(50/1→30/1) for elution to give cyclo(-DTrp-DAsp(OBzl)-Pro-DVal-Leu-)(7.20 g) as a pale yellow powder. A solution of the powder(5.89 g) in methanol(20 ml) was added to a suspension of 10% Pd/C (1.2 g) in methanol(100 ml). The reaction mixture was stirred at room temperature under an atmosphere of hydrogen(under atmospheric pressure) for 20 h. The catalysts were filtered off and the filtrate was concentrated under reduced pressure. The residual powder was purified by reverse-phase column chromatography (NACALAI TESQUE, COSMOSIL C$_{18}$-OPN) with methanol/water(1/1→2/1) for elution to give cyclo (-DTrp-DAsp-Pro-Val-Leu-)(4.30 g) as a colorless powder. To a solution of the powder(5.01 g) in methanol(10 ml) was added dropwise an aqueous solution of NaHCO$_3$(689 mg) at room temperature. The reaction mixture was concentrated under reduced pressure. The residue was recrystallized from methanol to give the title compound (4.4 g) as colorless crystals.
m.p.: >300° C.

IR(KBr,cm⁻¹):
3418,3064,2968,1659,1581,1542,1458,1398, 1341,1233,744.

¹H-NMR(300 MHz,DMSO-d₆,δ ppm):0.61(3H,d,J=6.6Hz),0.72(3H,d,J=6.4Hz),0.81(3H,d,J=7.6Hz),0.84(3H,d,J=7.3Hz),0.90-1.07(1H,m),1.08-1.30(2H,m),1.46-2.08(5H,m),2.18-2.31(1H,m),2.34-2.52(1H,m),2.61(1H,dd,J=11.0Hz,14.5Hz),2.87(1H,dd,J=11.9Hz,14.5Hz),3.08-3.25(1H,m),3.49-3.61(1H,m),4.00-4.16(2H,m),4.16-4.29(1H,m), 4.66(1H,d-like,J=7.3Hz),4.82-4.95(1H,m),6.94(1H,t,J=7.4Hz),7.03(1H,t,J=7.4Hz),7.11(1H,d,J=2.3Hz),7.27(1H,d,J=7.4Hz),7.30(1H,d,J=7.4Hz),7.52(1H,d,J=7.8Hz),7.94(1H,d,J=9.5Hz),8.65(1H,d,J=6.1Hz),8.77(1H,dd,J=1.3Hz,8.0Hz),10.79(1H,d,J=2.3Hz).

Optical Rotations: [α]_D^{20} = +78.2°(c 1.0, H₂O).

According to the same procedure described in Example 4, each title compound described in the following Examples 60-67 was prepared from the corresponding Fmoc amino acids in which sidechain functional groups were protected with the appropriate protective groups, if necessary.

EXAMPLE 60 cyclo(-DTrp-DAsp-Pro-DPen-Leu-)

m.p.: 185°-190° C.
IR(KBr,cm⁻¹): 3412,2926,1662,1536,1443,1239.
FAB-MS(m/e,(C₃₁H₄₂N₆O₇S+H)⁺):643.

¹H-NMR(300 MHz,DMSO-d₆,δ ppm):0.61(3H,d,J=6.2Hz),0.73(3H,d,J=6.2Hz),0.80-0.90(1H,m),1.00-1.20(2H,m), 1.23(3H,s),1.27(3H,s),1.60-1.85(2H,m),2.20-2.45(3H,m),2.77(1H,dd,J=6.4Hz,16.5Hz),2.89(1H,dd,J=12.0Hz,14.8Hz),3.10-3.45(3H,m),4.01(1H,q,J=5.6Hz),4.20-4.30(1H,m),4.49(1H,d,J=10.1Hz),4.80(1H,d,J=7.0Hz),4.95-5.05(1H,m),6.96(1H,t,J=7.5Hz),7.05(1H,t,J=7.5Hz),7.14(1H,s),7.32(1H,d,J=7.5Hz),7.52(1H,d,J=7.5Hz),7.60(1H,d,J=9.0Hz),7.90(1H,d,J=10.1Hz),8.83(1H,d,J=7.9Hz),8.88(1H,d,J=5.5Hz),10.81(1H,s).

EXAMPLE 61 cyclo(-DTrp-DAsp-Aib-DVal-Leu-)

m.p.: 169°-175° C.
IR(KBr,cm⁻¹):
3394,3058,2962,1659,1533,1464,1395,1374, 1233,1185.
High Resolution FAB-MS(m/e,(C₃₀H₄₂N₆O₇+H)⁺):
Calcd : 599.3193.
Found : 599.3179.

¹H-NMR(300 MHz,DMSO-d₆,δ ppm):0.65(3H,d,J=6.3Hz), 0.76(3H,d,J=6.3Hz),0.82(3H,d,J=6.3Hz),0.84(3H,d,J=6.3Hz),0.95-1.09(1H,m),1.07-1.15(2H,m),1.23(3H,s), 1.57(3H,s),1.68-1.84(1H,m),2.44-2.57(1H,m),2.76(1H,dd,J=9.7Hz,15.7Hz),2.86(1H,dd,J=11.6Hz,14.4Hz),3.15-3.60(1H,m),4.04-4.16(1H,m),4.18(1H,dd,J=6.8Hz,8.4Hz),4.25-4.38(1H,m),4.54-4.57(1H,m),6.96(1H,t,J=7.5Hz),7.04(1H,t,J=7.5Hz),7.13(1H,d,J=2.0Hz),7.31(1H,d,J=7.5Hz),7.44(1H,d,J=7.6Hz),7.51(1H,d,J=7.5Hz),7.99(1H,d,J=8.4Hz),8.45(1H,brs),8.72(1H,d,J=6.4Hz),8.80(1H,d,J=9.1Hz),0.78(1H,brs).

cyclo(-DTrp-nAsp-Pro-Aib-Leu-)

m.p.: 187°-193° C.
IR(KBr,cm⁻¹): 3442,1674,1533,1461,1203,1185.
High Resolution FAB-MS(m/e,(C₃₀H₄₀N₆O₇+H)⁺):
Calcd : 597.3036.
Found : 597.3060.

¹H-NMR(300 MHz,DMSO-d₆,δ ppm):0.65(3H,d,J=6.3Hz),s),1.74-2.12(5H,m),2.27(1H,dd,J=4.2Hz,16.3Hz),2.42-2.58(1H,m),2.70(1H,dd,J=4.5Hz,15.4Hz),2.93(1H,dd,J=10.1Hz,15.4Hz),3.15-3.43-(2H,m),4.02-4.13(1H,m),4.25-4.37(1H,m),4.43-4.52(1H,m),4.78-4.91(1H,m),6.96(1H,t, J=7.6Hz),7.05(1H,t,J=7.6Hz),7.14(1H,d,J=2.3Hz),7.32(1H,d,J=7.6Hz),7.81(1H,d,J=7.6Hz),7.60(1H,d,J=6.6Hz), 8.02(1H,d,J=8.8Hz),8.25(1H,d,J=8.0Hz),9.05(1H,s),10.84(1H,brs).

EXAMPLE 63 m.p.: 175° C.(dec.).
IR(KBr,cm⁻¹):
3448,2951,2926,1644,1536,1458,1386,1102, 741.
High Resolution FAB-MS(m/e,(C₃₂H₄₂N₆O₇+H)⁺):
Calcd : 623.3193.
Found : 623.3179.

¹H-NMR(300 MHz,DMSO-d₆,δ ppm):0.63(3H,d,J=6.3Hz),0.71(3H,d,J=6.4Hz),0.76-1.10(3H,m),1.18-1.34(2H,m), 1.40-2.20(10H,m),2.29(1H,dd,J=4.1Hz,15.9Hz),2.71(1H,dd,J=11.0Hz,15.9Hz),2.92(1H,dd,J=9.9Hz,14.3Hz),3.21(1H,dd,J=4.0Hz,14.3Hz),3.26-3.70-(2H,m),4.00-4.20(1H,m),4.24(1H,ddd,J=4.1Hz,6.7Hz,11.0Hz),4.52(1H,d-like, J=7.3Hz),4.87(1H,dt,J=4.0Hz,9.9Hz),6.96(1H,t,J=7.5Hz),7.05(1H,t,J=7.5Hz),7.13(1H,d,J=1.7Hz),7.32(1H,d,J=7.5Hz),7.51(1H,d,J=7.5Hz),7.53(1H,s),7.79(1H,d,J=6.7Hz),7.83(1H,d,J=9.9Hz),8.32(1H,d,J=7.8Hz),10.83(1H,d,J=1.7Hz),12.30(1H,brs).

EXAMPLE 64 cyclo(-DTrp-DAsp-Pro-Ac₆c-Leu-)

m.p.: 188.5° C.(dec.).
IR(KBr,cm⁻¹):
3418,2938,1677,1533,1458,1284,1236,1182, 743.
High Resolution FAB-MS(m/e,(C₃₃H₄₄N₆O₇+H)⁺):
Calcd : 637.3350.
Found : 637.3381.

¹H-NMR(300 MHz,DMSO-d₆,δ ppm):0.61(3H,d,J=6.4Hz),0.64-1.02(3H,m),0.71(3H,d,J=6.7Hz),1.12-2.24(14H,m),2.29(1H, dd,J=3.9Hz,16.1Hz),2.73(1H,dd,J=10.2Hz,16.1Hz),2.90(1H,dd,J=10.5Hz,14.4Hz), 3.28(1H,dd,J=5.8Hz,14.4Hz),3.40-3.70(2H,m),3.93-4.06(1H,m)4.22(1J,ddd, J=3.9Hz,7.8Hz,10.2Hz),4.61(1H,dd,J=1.7Hz,6.2Hz),4.88(1H,dt,J=5.8Hz,10.5Hz),6.95(1H,t,J=7.3Hz),7.04(1H,t, J=7.3Hz),7.13(1H,d,J=1.6Hz),7.22(1H,s),7.31(1H,d,J=7.3Hz),7.50(1H,d,J=7.3Hz),7.68(1H,d,J=5.8Hz),7.85(1H,d,J=8.7Hz),8.43(1H,d,J=7.8Hz),10.81(1H,d,J=1.6Hz),12.28(1H,brs).

Optical Rotations: [α]_D^{20} = +59.4°(c 0.19, DMSO).

EXAMPLE 65 cyclo(-DTrp-DAsp-Sar-DVal-Leu-)

m.p.: 175°-179° C.
IR(KBr,cm⁻¹):
3418,3064,2962,1659,1536,1464,1422,1236, 1176.

High Resolution FAB-MS(m/e,(C29H40-N6O7+H)+):
 Calcd : 585.3037.
 Found : 585.3066.
 1H-NMR(300 MHz,DMSO-d6,δ ppm):0.61(3H,d,J=6.8Hz),0.73(3H,d,J=6.3Hz), 0.826(3H,d,J=6.5Hz),0.833(3H,d,J=6.5Hz),0.95-1.06(-1H,m),1.09-1.29(2H,m),1.62-1.76(1H,m),2.31(1H,dd,J=3.5Hz,16.1Hz),2.75(3H,s),2.77(1H,dd,J=10.7Hz,16.-1Hz),2.90(1H,dd,J=11.6Hz,14.5Hz),2.96(1H,d,J=13.5-Hz),
 3.22(1H,dd,J=3.0Hz,14.5Hz),3.93-4.03(1H,m),4.14(1-H,dd,J=7.3Hz,10.1Hz), 4.27(1H,ddd,J=3.0Hz,8.1Hz,11.6Hz),4.79(1H,d,J=13.5Hz),5.03-5.14(1H,m),-6.88(1H,d,J=10.1Hz),6.95(1H,t,J=7.7Hz),7.04(1H,t,J=7.7Hz),7.14(1H,d,J=1.9Hz),7.31(1H,d,J=7.7Hz),7.5-1(1H,d,J=7.7Hz),7.69(1H,d,J=8.7Hz),8.76-8.83(2H,-m),10.81(1H,d,J=1.9Hz),12.30(1H,brs).
 Optical Rotations: [α]$_D^{20}$=+36.3°(c 0.41, MeOH).

EXAMPLE 66 cyclo(-DTro-DAsp-β-Ala-DVal-Leu-)

m.p.: 248° C.(dec.).
IR(KBr,cm$^{-1}$):
3316,2962,1662,1536,1443,1344,1257,1188, 744.
 High Resolution FAB-MS(m/e,(C29H40-N6O7+H)+):
 Calcd : 585.3037.
 Found : 585.3051.
 1H-NMR(300 MHz,DMSO-d6,δ ppm):0.61(3H,d,J=6.1Hz),0.72(3H,d,J=6.2Hz),0.81(3-H,d,J=6.6Hz),0.88(3H,d,J=6.6Hz),1.03-1.18(2H,m),1-.18-1.35(1H,m),1.73-1.90(1H,m),1.86-1.96(1H,m),2.-32-2.63(2H,m),2.63-2.98(3H,m),
 3.11-3.44(1H,m),3.50-3.63(1H,m),3.90-4.03(2H,m),4.1-3(1H,ddd,J=3.1Hz,7.0Hz,11.4Hz),4.61(1H,dt,J=3.4H-z,9.2Hz),6.63(1H,dd,J=4.8Hz,7.7Hz),6.96(1H,t,J=7.6-Hz),7.04(1H,t,J=7.6Hz),7.17(1H,d,J=1.6Hz),7.32(1H,-d,J=7.6Hz),7.50(1H,d,J=7.6Hz),7.72(1H,d,J=8.4Hz),-7.88(1H,d,J=9.2Hz),8.60(1H,d,J=4.0Hz),8.81(1H,d,J-=7.0Hz),10.81(1H,d,J=1.6Hz)),12.33(1H,brs).
 Optical Rotations: [α]$_D^{20}$=−2.2°(c 0.79, MeOH).

EXAMPLE 67 cyclo(-DTrp-DAsp-Pro-DThg-Leu-)

m.p.: 251° C.(dec.).
IR(KBr,cm$^{-1}$):
3418,2962,1668,1530,1446,1395,1344,1236, 744,705.
 High Resolution FAB-MS(m/e,(C32H38-N6O7S+H)+):
 Calcd : 651.2601.
 Found : 651.2617.
 1H-NMR(300 MHz,DMSO-d6,δ ppm):0.58(3H,d,J=6.3Hz),0.70(3H,d,J=6.4Hz),0.80-0-.98(1H,m),1.11-1.33(2H,m), 1.55-2.02(2H,m),2.-12-2.53(3H,m),2.60-3.72(5H,m),3.93-4.05(1H,m),4.-23-4.35(1H,m),4.76(1H,d-like,J=6.0Hz),
 4.88-5.03(1H,m),5.80(1H,d,J=9.4Hz),6.-89-7.01(3H,m),7.03(1H,t,J=7.5Hz),7.12(1H,brs),7.30(1-H,d,J=7.5Hz),
 7.45(1H,dd,J=1.3Hz,5.3Hz),7.45-7.62(1H,m),7.51(1H,-d,J=7.5Hz),8.25(1H,d,J=9.4Hz),8.81(1H,d,J=8.1Hz),-9.07(1H,d,J=5.3Hz),10.79(1H,brs).
 Optical Rotations: [α]$_D^{20}$=+60.8°(c 0.41, MeOH).

EXAMPLE 68 cyclo(-DTrp-DAsp-Thz-DVal-Leu-)

Thz-DVal-Leu-resin which was prepared from Fmoc-Leu-resin in the same manner described in Example 4, was unpacked from a reaction column and allowed to react with 2.5 equivalents of the symmetrical acid anhydride of Fmoc-nAsp(O$^t$Bu)(prepared previously from Fmoc-DAsp(O$^t$Bu) and DCC) and DMAP(10 mg) in DMF at room temperature for 3 h with occasional shaking. After removal of excess reagents, the resin was washed successively with DMF, tert-amyl alcohol, acetic acid, tert-amyl alcohol and DMF, and repacked in a reaction column. The further solid-phase peptide synthesis was performed by the standard protocol described in Example 4. The resulting DTrp-DAsp(O$^t$Bu)-Thz-DVal-Leu-resin was treated in the same manner described in Example 4 to give the title compound.
 m.p.: 205°-208° C.
 IR(KBr,cm$^-$):
3328,2962,2932,1665,1536,1461,1437,1284, 1248,44.
 High Resolution FAB-MS(m/e,(C30H40-N6O7S+H)+):
 Calcd : 629.2757.
 Found : 629.2749.
 1H-NMR(300 MHz,DMSO-d6,δ ppm):0.61(3H,d,J=6.3Hz),0.73(3H,d,J=6.4Hz),0.83(3-H,d,J=6.9Hz),0.87(3H,d,J=6.9Hz),0.95-1.33(3H,m),1-.60-1.78(1H,m),2.30(1H,dd,J=4.2Hz,15.8Hz),2.77(1H,-dd,J=9.8Hz,15.8Hz),2.90(1H,dd,
 J=11.2Hz,14.8Hz),2.96(1H,dd,J=7.8Hz,10.8Hz),3.43(-1H,dd,J=3.1Hz,14.8Hz),3.44(1H,dd,J=2.1Hz,10.8Hz)-,3.90(1H,
 d,J=9.8Hz),3.93-4.04(1H,m),4.14(1H,dd,J=8.9Hz,9.8-Hz),4.25(1H,ddd,J=3.1Hz,8.3Hz,11.2Hz),4.35(1H,d,J-=9.8Hz),
 5.10(1H,dt,J=4.2Hz,9.8Hz),5.37(1H,dd,J=2.1Hz,7.8H-z),6.95(1H,t,J=7.7Hz),7.01(1H,d,J=9.8Hz),7.04(1H,t,-J=7.7Hz),7.14(1H,d,J=1.8Hz),7.31(1H,d,J=7.7Hz),7.-51(1H,d,
 J=7.7Hz),7.83(1H,d,J=9.8Hz),8.80(1H,d,J=8.3Hz),8.-81(1H,d,J=4.7Hz),10.81(1H,d,J=1.8Hz).
 Optical Rotations: [α]$_D^{20}$=+35.2°(c 0.35, MeOH).

EXAMPLE 69 cyclo(-DTrp-DAsp-Pro-DVal-MeLeu-)

Fmoc-MeLeu-resin prepared in the same manner described in Example 4, was allowed to react with the symmetrical acid anhydride(2.5 equivalents) of Fmoc-Dval (which was previously prepared from Fmoc-DVal and DCC) and DMAP(10 mg) at room temperature for 3 h with occasional shaking of the reaction vessel. The subsequent treatments were performed as described in Example 68 to give the title compound.
 m.p.: 208° C.(dec.).
 IR(KBr,cm$^{-1}$):
3418,2962,1680,1647,1533,1461,1236,1203, 1179.
 High Resolution FAB-MS(m/e,(C32H44-N6O7+H)+):
 Calcd : 625.3350.
 Found : 625.3386.
 1H-NMR(300 MHz,DMSO-d6,δ ppm):0.65(3H,d,J=6.7Hz),0.76(3H,d,J=6.3Hz),0.83(3-H,d,J=6.6Hz),0.88(3H,d,J=6.9Hz),0.87-1.01(1H,m),1-.10-1.26(1H,m),1.28-1.42(1H,m),1.58-1.96(4H,m),2.-16-2.28(1H,m),2.38(1H,dd,J=4.1Hz, 16.2Hz),2.82(1H,dd,J=9.5Hz,16.2Hz),2.89(1H,dd,J=1-1.0Hz,14.8Hz),2.91(3H,s),3.20(1H,dd,J=3.3Hz,14.8Hz),3.26-3.68(2H,m),4.33(1H,ddd,J=3.3Hz,8.7Hz,11.0Hz),4.45-4.55(2H,m),4.74(1H,d-like,J=6.6Hz),4.87(1H,dt,J=4.1Hz,9.5Hz),6.95(1H,t,J=7.7Hz),7.04(1H,t,J=7.7Hz),7.12(1H,d,J=1.9Hz),7.31(1H,d,J=7.7Hz),7.53(1H,d,J=7.7Hz),7.60(1H,d,J=9.8Hz),7.66(1H,d,J=9.5Hz),8.45(1H,d,J=8.7Hz), 10.81(1H,d,J=1.9Hz),12.29(1H,brs).

Optical Rotations: $[\alpha]_D^{20} = +39.7°$ (c 0.25, MeOH).

EXAMPLE 70 cyclo(-DTrp-DAsp-MeMet-DVal-Leu-)

MeMet-DVal-Leu-resin prepared in the same manner described in Example 4, was allowed to react with the symmetrical acid anhydride of Fmoc-DAsp(O'Bu)(-previously prepared in the same manner described in Example 68). The subsequent treatments were performed as described in Example 68 to give the title compound.

m p.: 152°-161° C.
IR(KBr,cm$^{-1}$):
3412,2962,1659,1533,1462,1395,1285,1237, 1202,1180,743.
High Resolution FAB-MS(m/e,(C$_{32}$H$_{46}$-N$_6$O$_7$S+H)$^+$):
Calcd : 659.3226.
Found : 659.3205.
$^1$H-NMR(300 MHz,DMSO-d$_6$,δ ppm):0.61(3H,d,J=6.7Hz),0.72(3H,d,J=6.7Hz),0.81(3H,d,J=6.9Hz),0.83(3H,d,J=6.9Hz),0.95-1.33(3H,m),1.66-1.87(2H,m),1.90-2.03(1H,m),2.02(3H,s),2.23-2.40(3H,m),2.49(3H,s),2.78(1H,dd, J=10.4Hz,16.0Hz),2.90(1H,dd,J=10.9Hz,14.8Hz),3.25-3.38(1H,m),3.96-4.05(1H,m),4.19(1H,dd,J=6.5Hz,10.3Hz), 4.21-4.32(1H,m),5.00(1H,ddd,J=3.9Hz,8.9Hz,10.4Hz),5.1((1H,t,J=7.5Hz),6.73(1H,d,J=10.3Hz),6.96(1H,t,J=7.3Hz),7.04(1H,t,J=7.3Hz),7.14(1H,d,J=2.2Hz),7.31(1H, d,J=7.3Hz),7.51(1H,d,J=7.3Hz),7.68(1H,d,J=8.9Hz),8.75-8.84(2H,m),10.81(1H,d,J=2.2Hz),12.30(1H,brs).

According to the same procedure described in Example 6, each title compound described in the following Examples 71-74 was prepared from the corresponding Fmoc amino acids in which sidechain functional groups were protected with the appropriate protective groups, if necessary.

EXAMPLE 71 cyclo(-DTrp-DAsp-Pro-DtertLeu-Leu-)

m.p.: 188°-191° C.
IR(KBr,cm$^{-1}$):
3316,3064,2962,1656,1446,1236,1182,744.
High Resolution FAB-MS(m/e,(C$_{32}$H$_{44}$-N$_6$O$_7$+H)$^+$):
Calcd : 625.3350.
Found : 625.3370.
$^1$H-NMR(300 MHz,DMSO-d$_6$,δ ppm):0.61(3H,d,J=6.5Hz),0.72(3H,d,J=6.5Hz),0.87(9H,s),0.98-1.24(3H,m),1.60-1.74(2H,m),1.91-1.94(1H,m),2.24-2.29(1H,m),2.33(1H,dd, J=3.6Hz,16.5Hz),2.71-2.92(2H,m),3.26-3.37(2H,m),3.45-3.60(1H,m),3.95-4.02(1H,m),4.20(1H,d,J=10.2Hz),4.19-4.28(1H,m),4.78(1H,d-like,J=6.6Hz),4.98(1H,dt,J=4.2Hz,9.3Hz),6.95(1H,t,J=7.5Hz),7.04(1H,t,J=7.5Hz),7.13(1H,d,J=2.1Hz),7.31(1H,d,J=7.5Hz),7.51(1H,d,J=7.5Hz),7.64(1H,d,J=10.5Hz),7.71(1H,d,J=9.3Hz),8.76(1H,d,J=4.8Hz),8.81(1H,d,J=7.8Hz),10.79(1H,brs),12.28(1H,brs).

EXAMPLE 72 cyclo(-DTrp-DAsp-Sar-DThg-Leu-)

m.p. 171°-178° C.
IR(KBr,cm$^{-1}$):
3310,3064,2962,1665,1533,1428,1236,1173,
High Resolution FAB-MS(m/e,(C$_{30}$H$_{36}$-N$_6$O$_7$S+H)$^+$):
Calcd : 625.2444.
Found : 625.2456.
$^1$H-NMR(300 MHz,DMSO-d$_6$,δ ppm):0.60(3H,d,J=6.3Hz),0.70(3H,d,J=6.3Hz),0.83-0.93(1H,m),1.17-1.27(2H,m), 2.34(1H,dd,J=3.9Hz,16.2Hz),2.74-2.80(1H,m),2.80(3H,s),2.84-2.91(1H,m),3.04(1H,d,J=13.7Hz),3.30-3.40(1H,m), 3.99(1H,dd,J=5.4Hz,11.1Hz),4.27-4.33(1H,m),4.82(1H,d,J=13.7Hz),5.11(1H,dt,J=4.1Hz,9.4Hz),5.80(1H,d,J=10.5Hz),6.93-7.00(3H,m),7.04(1H,t,J=7.5Hz),7.14(1H,d,J=2.1Hz),7.31(1H,d,J=7.5Hz),7.43(1H,d,J=10.5Hz),7.47(1H,d,J=6.3Hz),7.51(1H,d,J=7.5Hz),7.74(1H,d,J=9.4Hz),8.80(1H,d,J=8.1Hz),9.13(1H,d,J=5.4Hz),10.83(1H,brs), 12.30(1H,brs).

EXAMPLE 73 cyclo(-DTrp-DAsp-CpGly-DThg-Leu-)

m.p.: 186°-191 C.
IR(KBr,cm$^{-1}$):3310,2962,1662,1530,741.
High Resolution FAB-MS(m/e,(C$_{34}$H$_{42}$-N$_6$O$_7$S+H)$^+$):
Calcd : 679.2914.
Found : 679.2964.
$^1$H-NMR(300 MHz,DMSO-d$_6$,δ ppm):0.59(3H,d,J=6.6Hz),0.71(3H,d,J=6.6Hz),0.83-0.95(1H,m),1.14-1.78(10H,m), 2.39(1H,dd,J=4.5Hz,16.8Hz),2.83-2.94(2H,m),3.19(1H,d,J=11.5Hz),3.20-3.41(1H,m),3.92-4.03(2H,m),4.35(1H,ddd, J=2.7Hz,8.3Hz,12.0Hz),4.58(1H,d,J=11.5Hz),5.25(1H,dt, J=4.2Hz,9.6Hz),5.76(1H,d,J=9.8Hz),6.93-6.99(3H,m),7.04(1H,t,J=7.4Hz),7.13(1H,d,J=2.1Hz),7.31(1H,d,J=7.4Hz),7.45(1H,dd,J=1.2Hz,4.8Hz),7.52(1H,d,J=7.4Hz),7.70(1H,d,J=9.6Hz),7.98(1H,d,J=9.8Hz),8.89(1H,d,J=8.3Hz),9.20(1H,d,J=6.3Hz),10.80(1H,d,J=2.1Hz).

EXAMPLE 74 cyclo(-DTrp-DAsp-Pro-DDpg-Leu-)

m.p.: 258.5°-261 C.
IR(KBr,cm$^{-1}$):
3310,3058,2962,1659,1533,1446,1344,1236, 1185,744.
High Resolution FAB-MS(m/e,(C$_{34}$H$_{42}$-N$_6$O$_7$+H)$^+$):
Calcd : 647.3193.
Found : 647.3165.
$^1$H-NMR(300 MHz,DMSO-d$_6$,δ ppm):0.58(3H,d,J=6.3Hz),0.71(3H,d,J=6.7Hz),0.78-0.99(1H,m),1.11-1.29(2H,m), 1.52-1.70(1H,m),1.70-1.87(1H,m),1.87-2.03(1H,m),2.-

21-2.33(1H,m),2.35(1H,dd,J=4.0Hz,16.2Hz),2.-
35-2.96(4H,m),
2.79(1H,dd,J=10.5Hz,16.2Hz),2.89(1H,dd,J=11.8Hz,-
14.7Hz),3.03-3.62(2H,m),3.26(1H,dd,J=3.0Hz,14.7Hz-
),3.97(1H,dt,J=5.5Hz,8.6Hz),4.29(1H,ddd,J=3.0Hz,8.-
2Hz,11.8Hz),4.79(1H,d-like,J=6.8Hz),4.-
91-5.03(H,m),4.95(1H,d,J=10.4Hz),5.-
58-5.72(3H,m),6.95(1H,t,J=7.6Hz),7.04(1H,
t,J=7.6Hz),7.13(1H,d,J=1.8Hz),7.31(1H,d,J=7.6Hz),-
7.50(1H,d,J=7.6Hz),7.65-7.73(1H,m),7.69(1H,d,J=10-
.4Hz),
8.76(1H,d,J=8.2Hz),8.88(1H,d,J=5.5Hz),10.79(1H,d,J-
=1.8Hz),12.07(1H,brs).

EXAMPLE 75 cyclo(-DTrp(CHO)-DCys(O₃Na)-Pro-DThg-Leu-)

DCys(O₃Bu₄N)-Pro-DThg-Leu-resin prepared in the same manner described in Example 5, was acylated with Boc-DTrp(CHO) by the standard protocol described in Example 5. The resulting resin was washed successively with DMF, methanol, and dichloromethane and dried in vacuo to give Boc-DTrp(CHO)-DCys(O₃Bu₄N)-Pro-nThg-Leu-resin. The resin was added to TFA/water(95/5, 20 ml) and the mixture was stirred at room temperature for 1.5 h and filtered. The collected resin was washed with TFA and the combined filtrate and washings were concentrated under reduced pressure. The residue was precipitated with ether to give DTrp(CHO)-DCys(O₃Bu₄N)-Pro-DThg-Leu. A solution of the pentapeptide(28 mg) in DMF(1.4 ml) was added dropwise to a solution of DCC(9 mg), HOBT H₂O(7 mg) and N-methylmorpholine(1.6 μl) in DMF(1.4 ml) under ice cooling over a period of 1 h. The reaction mixture was stirred under ice cooling for 1 h and at room temperature for 17 h. Acetic acid(10 μl) was added to the reaction mixture. The resulting mixture was stirred and concentrated under reduced pressure. The residue was triturated with water to give colorless dicyclohexyl urea which was collected by filtration and thoroughly washed with water. The combined filtrate and washings were lyophilized to give a colorless solid which was purified by thin layer chromatography on silica gel (Analtichem International, Empore sheet) with butanol/acetic acid/water(8/1/1) for development to give an ammonium salt of the title compound. A water solution of the ammonium salt was passed through a column of ion exchange resin(AMBERLITE IR-120B, H⁺-form) and lyophilized. The resulting solid(12.93 mg) was dissolved in water(0.6 ml) and the equimolar amount of NaHCO₃ was added. The solution was directly purified by reverse-phase short column chromatography(Waters, SEP-PAK C₁₈ cartridge) with water and methanol for elution. The combined methanolic layers were concentrated under reduced pressure to give the title compound(10.74 mg) as a colorless powder.

m.p.: 179°-180° C.
IR(KBr,cm⁻¹): 3472,1668,1533,1464,1197,1044.
FAB-MS(m/e,(C₃₂H₃₇N₆NaO₉S₂+H)⁺):737.
¹H-NMR(300 MHz,DMSO-d₆,δ ppm):0.50-0.67(6H,m),0.73-0.97(1H,m),1.04-1.19(1H,-m),1.31-1.43(1H,m),1.56-1.72(1H,m),1.74-1.98(2H,m),-2.19-2.30(1H,m),2.64(1H,dd,J=2.9Hz,12
.4Hz),3.00(1H,dd,J=11.5Hz,14.5Hz),3.12-3.59(3H,m),-3.66-3.78(1H,m),4.02-4.17(1H,m),4.-
37-4.52(1H,m),4.66(1H,d-like,J=6.4Hz),4.-
95-5.04(1H,m),5.71(1H,d,  J=8
4Hz),6.92-7.02(2H,m),7.-
17-7.38(3H,m),7.42(1H,dd,J=2.2Hz,4.2Hz),7.-
56-7.69(2H,m),7.92-8.07+8.13-8.26(1H,
brs×2),8.70-8.92(1H,m),8.74(1H,d,J=8.4Hz),8.97(1H,-d,J=7.4Hz),9.18-9.21+9.56-9.68(1H,brs×2).

EXAMPLE 76 cyclo(-DTrp-DCys(O₃Na)-Pro-DThg-Leu-)

cyclo(-DTrp(CHO)-DCys(O₃Na)-Pro-DThg-Leu-) prepared in Example 75(2.9 mg) was dissolved in water(0.5 ml). To this solution was added IN NaOH(4 μl) under ice cooling and the mixture was stirred at room temperature for 3 h. The reaction mixture was directly purified by reverse-phase short column chromatography(Waters, SEP-PAK C₁₈ cartridge) with water, water/methanol(10/1) and methanol for elution. The combined methanolic eluents were concentrated in vacuo to give the title compound(2.1 mg).

m.p.: 258°-261.5° C.
High Resolution FAB-MS(m/e,(C₃₁H₃₇N₆NaO₈S₂+H)⁺):
Calcd : 709.2090.
Found : 709.2115.
¹H-NMR(300 MHz,DMSO-d₆,δ ppm):0.54(3H,d,J=6.6Hz),0.69(3H,d,J=6.7Hz),0.74-0-.98(1H,m),1.10-1.37(2H,m), 1.39-1.71(2H,m),1.-
73-1.95(1H,m),2.-
20-2.30(1H,m),2.61(1H,dd,J=2.7Hz,12.5Hz),2.94(1H,-dd,J=11.7Hz,14.4Hz),
3.16(1H,dd,J=10.6Hz,12.5Hz),3.20(1H,dd,J=2.9Hz,1-4.4Hz),3.21-3.42(1H,m),3.67-3.79(1H,m),4.-
08-4.19(1H,m),
4.31(1H,ddd,J=2.9Hz,8.6Hz,11.7Hz),4.65(1H,dd,J=1.-7Hz,7.8Hz),4.99(1H,ddd,J=2.7Hz,8.6Hz,10.6Hz),5.71(-1H,d,J=8.3Hz),6.92-6.99(2H,m),6.98(1H,t,J=7.5Hz),-
7.06(1H,t,
J=7.5Hz),7.13(1H,d,J=2.1Hz),7.18(1H,d,J=8.6Hz),7.-
30(1H,d,J=7.5Hz),7.42(1H,dd,J=1.6Hz,4.7Hz),7.52(1-H,d,J=7.5Hz),8.71(1H,d,J=8.6Hz),8.75(1H,d,J=8.3H-z),8.94(1H,d,J=7.3Hz),10.77(1H,d,J=2.1Hz).

EXAMPLE 77 cyclo(-DTrp(CHO)-DAsp-Met(O)-DVal-Leu-)

cyclo(-DTrp(CHO)-DAsp-Met-DVal-leu-) prepared in Example 55 was allowed to react with acetic acid-35% H₂O, at 80° C. in the same manner described in Example 58 to give the title compound.
FAB-MS(m/e,(C₃₂H₄₄N₆O₁₀S+H)⁺):705.
¹H-NMR(300 MHz,DMSO-d₆,δ ppm):0.59(3H,d,J=6.0Hz),0.64(3H,d,J=6.0Hz),0.80(3-H,d,J=6.9Hz),0.83(3H,d,J=6.9Hz),-
0.90-1.31(3H,m),1.65-2.29(3H,m),2.40-2.82(4H,m),2.9-2-3.40(2H,m),2.96(3H,s),3.93-4.05(1H,m),4.10-4.22(1-H,m),4.39-4.59(3H,m),7.22-7.45(3H,m),7.-
51-7.60(1H,m),7.61-7.72(2H,m),8.00+8.22(1H,brs),8.-
65-8.75(1H,m),8.76-8.97(2H,m),9.25+9.63(1H,brs).

According to the same procedure described in Example 6, each title compound described in the following Examples 78-82 was prepared from the corresponding Fmoc amino acids in which sidechain functional groups were protected with the appropriate protective groups, if necessary.

EXAMPLE 78 cyclo(-DTrp-DAsp-ⁱPrGly-DThg-Leu-)

m.p.: 172.5°-178.5° C.

IR(KBr,cm$^{-1}$):
3304,2968,1668,1533,1461,1374,1236,1179, 1152,744,708.
High Resolution FAB-MS(m/e,(C$_{32}$H$_{40}$N$_6$O$_7$S+H)$^+$):
Calcd : 653.2757.
Found : 653.2737.
$^1$H-NMR(300 MHz,DMSO-d$_6$,δ ppm):0.58(3H,d,J=6.3Hz),0.71(3H,d,J=6.3Hz),0.80–0.94(1H,m),0.97(3H,d,J=6.6Hz),
1.10–1.32(2H,m),1.15(3H,d,J=6.6Hz),2.34–2.44(1H,m),2.82–2.95(2H,m),3.29(1H,d,J=14.7Hz),3.30–3.40(1H,m),3.80–3.94(1H,m),3.95–4.08(1H,m),4.36(1H,ddd,J=2.6Hz,8.3Hz,11.1Hz),4.52(1H,d,J=14.7Hz),5.16–5.27(1H,m),
5.75(1H,d,J=9.8Hz),6.91–7.00(3H,m),7.04(1H,t,J=7.9Hz),
7.12(1H,d,J=1.8Hz),7.31(1H,d,J=7.9Hz),7.45(1H,dd,J=1.6Hz,5.2Hz),7.51(1H,d,J=7.9Hz),7.67(1H,d,J=9.3Hz),
8.01(1H,d,J=9.8Hz),8.90(1H,d,J=8.3Hz),9.20(1H,d,J=5.7Hz),10.80(1H,d,J=1.8Hz),12.25(1H,brs).

EXAMPLE 79 cyclo(-DTrp-DAsp-trans-Hyp-DThg-Leu-)

m.p.: 229°–233° C.
IR(KBr,cm$^{-1}$):
3310,3064,2962,1665,1530,1443,1341,1233, 744,705.
High Resolution FAB-MS(m/e,(C$_{32}$H$_{38}$N$_6$O$_8$S+H)$^+$):
Calcd : 667.2550.
Found : 667.2575.
$^1$H-NMR(300 MHz,DMSO-d$_6$,δ ppm):0.58(3H,d,J=6.7Hz),0.71(3H,d,J=6.3Hz),0.81–0.99(1H,m),1.12–1.28(2H,m),
1.56–1.69(1H,m),2.34(1H,dd,J=4.4Hz,16.0Hz),2.39–2.70(1H,m),2.81(1H,dd,J=9.9Hz,16.0Hz),2.88(1H,dd,J=12.3Hz,14.2Hz),3.02–3.62(3H,m),3.96(1H,dt,J=5.1Hz,7.6Hz),4.22–4.34(2H,m),4.88(1H,dd,J=2.5Hz,8.0Hz),5.01(1H,ddd,
J=4.4Hz,9.3Hz,9.9Hz),5.20(1H,d,J=4.1Hz),5.80(1H,d,J=10.0Hz),6.91–7.03(3H,m),7.04(1H,t,J=7.7Hz),7.13(1H,d,J=1.7Hz),7.31(1H,d,J=7.7Hz),7.47(1H,dd,J=1.3Hz,5.2Hz),7.51(1H,d,J=7.7Hz),7.82(1H,d,J=9.3Hz),7.90(1H,d,J=10.0Hz),8.80(1H,d,J=8.2Hz),9.09(1H,d,J=5.1Hz),10.80(1H,d,J=1.7Hz).

EXAMPLE 80 cyclo(-DTrp-DAsp-Pro-DFug-Leu-)

m.p.: 202°–208° C.
IR(KBr,cm$^{-1}$): 2962,2932,1665,1536,1446,1236,1104, 741.
High Resolution FAB-MS(m/e,(C$_{32}$H$_{38}$N$_6$O$_8$+H)$^+$):
Calcd : 635.2829.
Found : 635.2859.
$^1$H-NMR(300 MHz,DMSO-d$_6$,δ ppm):0.58(3H,d,J=6.4Hz),0.71(3H,d,J=6.1Hz),0.85–0.95(1H,m),1.15–1.35(2H,m), 1.60–2.05(3H,m),2.20–2.50(2H,m),2.80(1H,dd,J=12.0Hz,14.8Hz),2.90(1H,dd,J=10.3Hz,15.9Hz),3.10–3.50(3H,m),
3.95–4.05(1H,m),4.25–4.35(1H,m),4.80(1H,d-like,J=6.9Hz),4.95–5.05(1H,m),5.69(1H,d,J=10.0Hz),6.24(1H,d,J=3.1Hz),6.42(1H,dd,J=1.8Hz,3.1Hz),6.96(1H,t,J=7.2Hz),7.05(1H,t,J=7.2Hz),7.14(1H,d,J=1.5Hz),7.32(1H,d,J=7.2Hz),7.52(1H,d,J=7.2Hz),7.63(1H,d,J=1.8Hz),7.71(1H,d,J=7.4Hz),7.98(1H,d,J=10.0Hz),8.79(1H,d,J=8.2Hz),
9.05(1H,d,J=5.2Hz),10.81(1H,d,J=1.5Hz).

EXAMPLE 81 cyclo(-DTrp-DAsp-Pro-DCpg-Leu-)

m.p. 199°–203° C.
IR(KBr,cm$^{-1}$):
3310,3064,2962,2872,1662,1533,1458,1344, 1236,741.
High Resolution FAB-MS(m/e,(C$_{33}$H$_{44}$N$_6$O$_7$+H)$^+$):
Calcd : 637.3350.
Found : 637.3358.
$^1$H-NMR(300 MHz,DMSO-d$_6$,δ ppm):0.60(3H,d,J=6.7Hz),0.72(3H,d,J=6.5Hz),0.75–1.08(2H,m),1.10–1.38(4H,m), 1.40–2.02(9H,m),2.18–2.45(2H,m),2.70–2.95(2H,m),3.02–3.50(3H,m),3.90–4.03(1H,m),4.15–4.34(1H,m),4.20(1H,t,J=9.2Hz),4.72(1H,d-like,J=6.3Hz),4.88–5.03(1H,m),6.95(1H,t,J=7.4Hz),7.04(1H,t,J=7.4Hz),7.13(1H,d,J=1.5Hz),7.30(1H,d,J=7.4Hz),7.43–7.61(1H,m),7.51(1H,d,J=7.4Hz),
7.62–7.85(1H,m),8.76(2H,brs),10.79(1H,brs),12.25(1H,brs).
Optical Rotations: [α]$_D^{20}$= +49.9°(c 0.34, MeOH).

EXAMPLE 82 cyclo(-DTrp-DAsp-Pro-DEtg-Leu-)

m.p.: 149°–154° C.
IR(KBr,cm$^{-1}$): 3412,2962,1674,1533,1461,1239,741.
High Resolution FAB-MS(m/e,(C$_{34}$H$_{42}$N$_6$O$_7$S+H)$^+$):
Calcd : 679.2914.
Found : 679.2912.
$^1$H-NMR(300 MHz,DMSO-d$_6$,δ ppm):0.63(3H,d,J=6.7Hz),0.70(3H,d,J=6.4Hz),0.73(3H,t,J=7.0Hz),0.85–1.00(1H,m),
1.15–1.30(2H,m),1.80–2.05(4H,m),2.10–2.20(1H,m),2.35–2.45(1H,m),2.45–2.60(1H,m),2.74(1H,dd,J=9.8Hz,16.2Hz),2.93(1H,dd,J=11.0Hz,14.5Hz),3.14(1H,dd,J=3.8Hz,14.5Hz),3.40–3.60(2H,m),4.15–4.35(2H,m),4.50–4.60(1H,m),4.75–4.90(1H,m),6.79(1H,d,J=3.7Hz),6.92(1H,dd,J=3.7Hz,5.2Hz),6.97(1H,t,J=7.3Hz),7.05(1H,t,J=7.3Hz),7.18(1H,d,J=1.8Hz),7.32(1H,d,J=7.3Hz),7.38(1H,d,J=5.2Hz),7.45–7.55(3H,m),8.21(1H,s),8.38(1H,d,J=8.3Hz),10.84(1H,d,J=1.8Hz).

EXAMPLE 83 cyclo(-DTrp-DAsp-CmGly-DThg-Leu-)

The title compound was prepared from Fmoc-Leu, Fmoc-DThg, Fmoc-DAsp(O$^t$Bu)-Cm(O$^t$Bu)Gly, and Fmoc-DTrp as the same procedure described in Example 6.
m.p.: 202° C.(dec.).
IR(KBr,cm$^{-1}$):
3412,3058,2962,1668,1536,1467,1437,1341, 1233,744,710.
High Resolution FAB-MS(m/e,(C$_{31}$H$_{36}$N$_6$O$_9$S+H)$^+$):
Calcd : 669.2343.

Found : 669.2347.
$^1$H-NMR(300 MHz,DMSO-d$_6$,δ ppm):0.61(3H,d,J=6.6Hz),0.72(3H,d,J=6.3Hz),0.90-1.05(1H,m),1.15-1.34(2H,m),
2.34(1H,dd,J=4.4Hz,15.9Hz),2.73(1H,dd,J=9.1Hz,15.9Hz),2.91(1H,dd,J=11.1Hz,14.4Hz),3.06(1H,d,J=14.2Hz),3.27(1H,dd,J=3.0Hz,14.4Hz),3.62(1H,d,J=18.7Hz),3.94(1H,d,
J=18.7Hz),4.02(1H,dt,J=6.2Hz,7.5Hz),4.32(1H,ddd,J=3.0Hz,7.5Hz,11.1Hz),4.79(1H,d,J=14.2Hz),4.90(1H,dt,J=4.4Hz,9.1Hz),5.75(1H,d,J=8.9Hz),6.92-7.01(3H,m),7.04(1H,t,J=7.5Hz),7.15(1H,d,J=2.3Hz),7.31(1H,d,J=7.5Hz),
7.46(1H,dd,J=1.9Hz,6.4Hz),7.51(2H,d×2,J=7.5Hz,8.9Hz),
7.82(1H,d,J=9.1Hz),8.69(1H,d,J=7.5Hz),9.00(1H,d,J=6.2Hz),10.82(1H,brs).

EXAMPLE 84 cyclo(-DTrp-DAsp-Pro-DVal-His). TFA salt

A HMP resin(0.25 mmol, Applied Biosystems) was acylated successively with Fmoc-DTrp, Fmoc-His(Boc)-OPfp, Fmoc-DVal, Fmoc-Pro, and Fmoc-DAsp(O$^t$Bu) by use of a 431A type automatic peptide synthesizer(Applied Biochemistry) according to the standard manual of this machine for the Fmoc-strategy to give DAsp(O$^t$Bu)-Pro-DVal-His(Boc)-DTrp-resin. The resin was treated in the same manner described in Example 4 to give the title compound(11 mg) as a pale yellow powder.
m.p.: 250° C.(dec.).
IR(KBr,cm$^{-1}$):
3418,3058,2968,1671,1539,1449,1203,1140.
High Resolution FAB-MS(m/e,(C$_{31}$H$_{38}$N$_8$O$_7$+H)$^+$):
Calcd : 635.2942.
Found : 635.2932.
$^1$H-NMR(300 MHz,DMSO-d$_6$,δ ppm):0.74(3H,d,J=6.9Hz),0.83(3H,d,J=6.9Hz),1.20-1.32(1H,m),1.55-1.70(1H,m), 1.71-1.85(1H,m),1.85-1.97(1H,m),2.21-2.33(2H,m),2.66-2.84(3H,m),2.95(1H,dd,J=10.1Hz,14.9Hz),3.10-3.45(3H,m),4.10(1H,dd,J=8.6Hz,9.5Hz),4.25-4.35(2H,m),4.74(1H,d-like,J=7.3Hz),4.95(1H,dt,J=3.6Hz,10.4Hz),6.92(1H,d,J=1.6Hz),6.93-7.10(3H,m),7.34(1H,d,J=7.7Hz),7.46(1H,d,J=7.7Hz),7.54-7.65(2H,m),8.20-8.30(1H,m),8.65(1H,d,
J=8.0Hz),8.92(1H,d,J=5.1Hz),10.63(1H,d,J=1.6Hz).

EXAMPLE 85 cyclo(-DTrp-DAsp-IeGly-DVal-Leu-)

cyclo(-DTrp-DAsp(OBzl)-IeGly-DVal-Leu-).HCl which was prepared from Leu-O$^t$Bu HCl, Boc-DVal, Boc-IeGly, Boc-DAsp(OBzl), and Boc-DTrp according to the same procedure described in Example 2, was hydrolized with 4 equivalents of 1N NaOH in methanol to give the title compound.
m.p.: 198° C.(dec.).
IR(KBr,cm$^{-1}$): 3322,3064,2926,1731,1659,1539,1470.
High Resolution FAB-MS(m/e,(C$_{33}$H$_{44}$N$_8$O$_7$+H)$^+$):
Calcd : 665.3412.
Found : 665.3420.
$^1$H-NMR(300 MHz,DMSO-d$_6$,δ ppm):0.62(3H,d,J=6.5Hz),0.73(3H,d,J=6.5Hz),0.82(3H,d,J=6.9Hz),0.83(3H,d,J=6.9Hz),0.90-1.10(3H,m),1.62-1.74(1H,m),2.17(2H,t,J=7.2Hz),2.23-2.29(1H,m),2.69-2.94(4H,m),3.07(1H,d,J=13.7Hz),3.20-3.30(1H,m),4.03(1H,dd,J=6.0Hz,13.0Hz),4.15(1H,dd,J=6.9Hz,9.6Hz),4.34(1H,dt,J=4.5Hz,8.1Hz),
4.70(1H,d,J=13.7Hz),5.14(1H,dt,J=4.5Hz,9.0Hz),6.88(1H,s),6.96(1H,t,J=7.5Hz),7.04(1H,t,J=7.5Hz),7.13(1H,d,
J=2.4Hz),7.27(1H,d,J=9.6Hz),7.31(1H,d,J=7.5Hz),7.51(1H,d,J=7.5Hz),7.68(1H,d,J=9.0Hz),7.74(1H,brs),8.80(1H,d,J=6.0Hz),8.87(1H,d,J=8.1Hz),10.81(1H,brs).

EXAMPLE 86 cyclo(-DTrp(COOCH$_3$)-DAsp-Pro-DVal-Leu-)

(86-a) Boc-DTrp(COOCH$_3$)

To a solution of Boc-DTrp-OBzl(1 g) in dichloromethane(8 ml) was added Bu$_4$NHSO$_4$(8.62 mg) and pulverized NaOH(253 mg) under ice cooling. To the resulting suspension was added dropwise a solution of methyl chloroformate(599 mg) in dichloromethane(6 ml) under ice cooling over a period of 30 min. The reaction mixture was stirred under ice cooling for 30 min and at room temperature for 12 h, diluted with dichloromethane, washed successively with water, 5% KHSO., saturated NaHCO$_3$ and saturated NaCl, dried over MgSO$_4$, and filtered. The filtrate was concentrated under reduced pressure to give Boc-DTrp(COOCH$_3$)-OBzl(1.42 g) as a colorless solid. The solid was hydrogenolized over a catalytic amount of 10% Pd/C in methanol under an atmosphere of hydrogen(under atmospheric pressure) to give Boc-DTrp(COOCH$_3$).

(86-b) cyclo(-DTrp(COOCH$_3$)-DAsp-Pro-DVal-Leu-)

DAsp(OBzl)-Pro-DVal-Leu-OPac prepared in Example 59 was acylated with Boc-DTrp(COOCH$_3$) and the resulting pentapeptide was treated in the same manner described in Example 59 to give the title compound.
m.p. 164°-173° C.
IR(KBr,cm$^{-1}$):
3304,2968,1740,1656,1539,1461,1389,1341,
1314,1260,1197,1092,765.
High Resolution FAB-MS(m/e,(C$_{33}$H$_{44}$N$_6$O$_9$+H)$^+$):
Calcd : 669.3248.
Found : 669.3275.
$^1$H-NMR(300 MHz,DMSO-d$_6$,δ ppm):0.57(3H,d,J=6.3Hz),0.66(3H,d,J=6.3Hz),0.82(3H,d,J=6.9Hz),0.85(3H,d,J=6.9Hz),0.80-1.00(1H,m),1.10-1.32(2H,m),1.57-1.83(3H,m),1.85-1.98(1H,m),2.20-2.32(1H,m),2.40(1H,dd,J=3.2Hz,16.1Hz),2.69-2.82(1H,m),2.90(1H,dd,J=12.3Hz,15.0Hz),3.03-3.20(2H,m),3.20-3.50(1H,m),3.87-4.00(1H,m),3.96(3H,s),4.14(1H,t,J=8.8Hz),4.32-4.42(1H,m),4.77(1H,d-like,J=7.1Hz),4.95(1H,dt,J=2.6Hz,8.8Hz),7.26(1H,t,
J=7.5Hz),7.43-7.58(2H,m),7.56(1H,t,J=7.5Hz),7.59(1H,d,J=7.5Hz),7.78(1H,d,J=8.8Hz),8.06(1H,d,J=7.5Hz),8.79(1H,d,J=4.3Hz),8.92(1H,d,J=8.0Hz).

EXAMPLE 87 cyclo(-DTrp(COO$^t$Bu)-DAsp-Pro-DVal-leu-)

According to the method described in the literature [H. Franzén et al. J. Chem. Soc., Chem. Commun., 1699 (1984)], DMAP(2 mg) and (Boc)$_2$O(38.2 mg) were added to a solution of cyclo(-DTrp-DAsp(OBzl)-Pro-DVal-Leu-)(123 mg, prepared in Example 59) in acetonitrile(5 ml) at room temperature. The reaction mixture was stirred at room temperature for 2 h and concentrated under reduced pressure. EtOAc was added to the residue and the resulting mixture was washed with dil. HCl, dried over MgSO$_4$ and filtered. The filtrate was concentrated under reduced pressure to give a colorless powder (114 mg). To a solution of the powder(114 mg) in methanol(10 ml) was added 10% Pd/C(10 mg). The mixture was vigorously stirred at room temperature under an atmosphere of hydrogen-(under atmospheric pressure) for 2 h and filtered. The filtrate was concentrated under reduced pressure to give the residue which was purified by column chromatography on silica gel(Merck, KIESELGEL with chloroform/methanol(9/1) for elution to give the title compound(52 mg) as a colorless powder.

m.p.: 176°-177° C.

IR(KBr,cm$^{-1}$):
,3928,3064,2968,1737,1653,1542,1458,
1374,1341,1314,1257,1230,1161.

High Resolution FAB-MS(m/e,(C$_{36}$H$_{50}$N$_6$O$_9$+H)$^+$):
Calcd : 711.3718.
Found : 711.3699.

$^1$H-NMR(300 MHz,DMSO-d$_6$,δ ppm):0.60(3H,d,J=6.6Hz),0.72(3H,d,J=6.6Hz),0.82(3-H,d,J=6.5Hz),0.86(3H,d,J=m),1.60(9H,s),1.72-1.87(1-H,m),1.87-1.98(1H m) 2.21-2.32(1H,m),2.33(1H,dd,J=3.9Hz,16.1Hz),2.79(1-H,dd,J=10.2Hz,16.1Hz),2.88(1H,dd,J=11.7Hz,14.4Hz),3.10-3.35(3H,m),3.-88-3.98(1H,m),4.13(1H,dd,J=8.3Hz,10.3Hz), 4.22-4.31(1H,m),4.76(1H,d-like,J=7.3Hz),4.97(1H,ddd,J=3.9Hz,8.8Hz,10.2Hz),7.2-3(1H,t,J=7.0Hz),7.30(1H,t, J=7.0Hz),7.48(1H,d,J=10.0Hz),7.50(1H,s),7.57(1H,d,-J=7.0Hz),7.78(1H,d,J=8.8Hz),8.01(1H,d,J=8.1Hz),8.-80(1H,d,J=5.4Hz),8.90(1H,d,J=8.3Hz).

EXAMPLE 88 cyclo(-DTrp(O)-Dsp-Pro-DVal-Leu-)

cyclo(-DTrp-DAsp-Pro-DVal-Leu-)(10 mg) prepared in Example 59 was dissolved in a mixture of DMSO, conc. HCl and acetic acid(1/10/20, 0.16 ml). The reaction mixture was stirred at room temperature for 1 h and concentrated in vacuo. The residue was triturated with water to give the title compound(2.3 mg) as an off-white powder.

m.p.: 175°-195° C.

IR(KBr,cm$^{-1}$)
3268,3064,2968,1659,1539,1476,1452,1398,
1344,1290,1230,1188,753,660.

FAB-MS(m/e,(C$_{31}$H$_{42}$N$_6$O$_8$+H)$^+$):627.

$^1$H-NMR(300 MHz,DMSO-d$_6$,δ ppm):0.74-1.23(12H,m),1.13-1.38(1H,m),1.40-1.8-7(5H,m),1.87-2.00(1H,m),2.00-2.19(1H,m),2.-12-2.40(1H,m),2.68-2.83(2H,m),3.02-3.80(3H,m),4.-00-4.12(1H,m),4.14-4.25(1H,m),4.30-4.35(1H, m),4.76(1H,d-like,J=7.6Hz),4.85-5.01(1H,m),6.81(1H-,t,J=7.8Hz),6.87-7.01(1H,m),7.06(1H,d,J=7.8Hz),7.1-4-7.22(1H,m),7.24(1H,d,J=7.8Hz),7.42-7.60(1H,m),7.-63-7.80(1H,m),8.-80-8.94(1H,m),9.03(1H,d,J=8.2Hz),10.42+10.37(1H,s-×2).

EXAMPLE 89 cyclo(-DTrp(O)-DAsp-MeAla-DVal-Leu-)

cyclo(-DTrp-DAsp-MeAla-DVal-Leu-) prepared in Example 13 was treated as the same procedure described in Example 88 to give the title compound.

m.p.: 215° C.(dec.).
FAB-MS(m/e,(C$_{30}$H$_{42}$N$_6$O$_8$+H)$^+$):615.

EXAMPLE 90 cyclo(-DTrp(CH$_2$COOCH$_3$)-DAsp-Pro-DVal-Leu-)

cyclo(-DTrp-DAsp(OBzl)-Pro-DVal-Leu-) prepared in Example 59 was allowed to react with methyl bromoacetate in the presence of Bu$_4$NHSO$_4$ and NaOH in the same manner described in Example(86-a) to give cyclo (-DTrp(CH$_2$COOCH$_3$)-nAsp(OBzl)-Pro-DVal-Leu-). The cyclic pentapeptide was hydrogenolized over a catalytic amount of 10% Pd/C under an atmosphere of hydrogen(under atmospheric pressure) to give the title compound as a colorless solid.

m.p.: 153°-160° C.
IR(KBr,cm$^{-1}$): 3310,2968,1743,1659,1539,1473,1446, 1224,1182,741.

High Resolution FAB-MS(m/e,(C$_{34}$H$_{46}$N$_6$O$_9$+H)$^+$):
Calcd : 683.3405.
Found : 683.3430.

$^1$H-NMR(300 MHz,DMSO-d$_6$,δ ppm):0.65(3H,d,J=5.6Hz),0.73(3H,d,J=5.7Hz),0.82(3-H,d,J=6.6Hz),0.86(3H,d,J=6.6Hz);1.10-1.32(3H,m),1-.52-1.82(3H,m),1.85-1.99(1H,m),2.20-2.66(2H,m),2.73--2.87(1H,m),2.90(1H,dd,J=12.1Hz,14.8Hz),3.09-3.39(-3H,m),3.65(3H,s),3.99(1H,dt,J=5.4Hz,7.9Hz),4.14(1H,-dd,J=7.9Hz,10.1Hz),4.19-4.30(1H, m),4.76(1H,d-like,J=7.4Hz),4.88-5.07(1H,m),5.02(1H,-ABq,J=17.8Hz),5.06(1H,ABq,J=17.8Hz),7.02(1H,t,J-=7.3Hz),7.08(1H,s),7.11(1H,t,J=7.3Hz),7.33(1H,d,J=-7.3Hz),7.50(1H,d,J=10.1Hz),7.55(1H,d,J=7.3Hz),7.72-(1H,d,J=8.1Hz),8.78(1H,d,J=5.4Hz),8.82(1H,d,J=8.1-Hz).

EXAMPLE 91 cyclo(-DTrp(CH$_2$CONH$_2$)-DAsp-Pro-DVal-Leu-)

Through a solution of cyclo(-DTrp(CH$_2$COOCH$_3$)-DAsp -Pro-DVal-Leu-)(30.0 mg, prepared in Example 90) in methanol(1 ml) was bubbled NH$_3$ at −70° C. for 20 min. The saturated solution was allowed to stand at room temperature for 2 h in a sealded tube. The reaction mixture was concentrated under reduced pressure. The residue was triturated with ether to give the title compound(13.0 mg) as a colorless powder.

m.p.: 195°-202° C.

IR(KBr,cm$^{-1}$): 3304,2968,1665,1539,1473,1398,741.
High Resolution FAB-MS(m/e,(C$_{33}$H$_{45}$N$_7$O$_8$+H)$^+$):
Calcd : 668.3408.
Found : 668.3420.

$^1$H-NMR(300 MHz,DMSO-d$_6$,δ ppm):0.65(3H,d,J=6.4Hz),0.73(3H,d,J=6.4Hz),0.82(3-H,d,J=6.6Hz),0.85(3H,d,J=6.9Hz),1.02-1.36(3H,m),1-.52-1.82(3H,m),1.84-1.99(1H,m),2.20-2.65(2H,m),2.65--2.73(1H,m),2.91(1H,dd,J=11.4Hz,14.6Hz),3.08-3.51(-3H,m),3.94-4.04(1H,m),4.13(1H,dd,J=8.4Hz,9.5Hz),4.-22-4.32(1H,m),4.64(1H,ABq,J=16.8Hz), 4.70(1H,ABq,J=16.8Hz),4.71-4.77(1H,m),4.87-5.03(1-H,m),7.00(1H,t,J=7.7Hz),7.05(1H,s),7.10(1H,t,J=7.7-

Hz),7.18(1H,brs),7.28(1H,d,J=7.7Hz),7.41(1H,brs),7.53(1H,d,J=7.7Hz),7.56-7.67(2H,m),8.73-8.82(1H,m),8.74 (1H,d,J=5.9Hz).

EXAMPLE 92 cyclo(-DTrp(CH$_2$CONHCH$_3$)-DAsp-Pro-DVal-Leu-)

cyclo(-DTrp(CH$_2$COOCH$_3$)-DAsp-Pro-DVal-Leu-) prepared in Example 90 was allowed to react with 40% methylamine/methanol as the same procedure described in Example 91 to give the title compound.

m.p.: 192°-202° C.

IR(KBr,cm$^{-1}$): 3298,3064,2968,1659,1545,1473,1395, 1338,741.

High Resolution FAB-MS(m/e,(C$_{34}$H$_{47}$N$_7$O$_8$+H)$^+$):

Calcd : 682.3565.

Found : 682.3567.

$^1$H-NMR(300 MHz,DMSO-d$_6$,δ ppm):0.65(3H,d,J=6.1Hz),0.72(3H,d,J=6.1Hz),0.81(3H,d,J=6.5Hz),0.85(3H,d,J=6.5Hz),1.06-1.32(3H,m),1.51-1.82(3H,m),1.83-1.99(1H,m),2.17-2.31(1H,m),2.41-2.82(2H,m),2.58(3H,d,J=4.7Hz), 2.91(1H,dd,J=11.7Hz,13.8Hz),3.07-3.60(3H,m),3.95-4.06(1H,m),4.12(1H,dd,J=8.1Hz,9.8Hz),4.21-4.32(1H,m),4.64-4.77(1H,m),4.65(1H,ABq,J=16.4Hz),4.71(1H,ABq,J=16.4Hz),4.84-5.03(1H,m),7.00(1H,t,J=7.5Hz),7.07(1H,s), 7.09(1H,t,J=7.5Hz),7.30(1H,d,J=7.5Hz),7.47-7.60(1H,m),7.53(1H,d,J=7.5Hz),7.70(1H,d,J=9.8Hz),7.88-7.96(1H,m), 8.68-8.79(2H,m).

EXAMPLE 93 cyclo(-DTrp(CH$_2$COOH)-DAsp-Pro-DVal-Leu-)

cyclo(-DTrp(CH$_2$COOCH$_3$)-DAsp(OBzl)-Pro-DVal-Leu-) prepared in Example 90 was hydrolized with 1N NaOH in methanol to give the title compound.

m.p.: 181.5°-183° C.

IR(KBr,cm$^{-1}$): 3304,2968,1725,1656,1539,1473,1449,1227, 1188,741.

High Resolution FAB-MS(m/e,(C$_{33}$H$_{44}$N$_6$O$_9$+H)$^+$):

Calcd : 669.3248.

Found : 669.3220.

$^1$H-NMR(300 MHz,DMSO-d$_6$,δ ppm):0.65(3H,d,J=5.1Hz),0.73(3H,d,J=5.4Hz),0.82(3H,d,J=7.0Hz),0.86(3H,d,J=6.6Hz),1.10-1.34(3H,m),1.52-1.83(3H,m),1.85-2.00(1H,m),2.21-2.67(2H,m),2.73-2.88(1H,m),2.90(1H,dd,J=12.8Hz,13.6Hz),3.07-3.49(3H,m),3.94-4.04(1H,m),4.14(1H,dd,J=8.1Hz,10.0Hz),4.19-4.31(1H,m),4.76(1H,d-like,J=7.1Hz),4.80-5.05(3H,m),7.01(1H,t,J=7.4Hz),7.07(1H,s),7.10(1H,t,J=7.4Hz),7.26-7.39(1H,m),7.50(1H,d,J=10.0Hz),7.54(1H,d,J=7.4Hz),7.73(1H,d,J=8.7Hz),8.78(1H,d,J=4.9Hz),8.83(1H,d,J=8.0Hz),12.32(2H,br-s).

According to the same procedure described in Example 4, each title compound described in the following Examples 94-97 was prepared from the corresponding Fmoc amino acid in which sidechain functional groups were protected with the appropriate protective groups, if necessary.

EXAMPLE 94 cyclo(-DTrp-DAsp-Ala-DVal-C$_6$al-)

m.p.: 225° C.(dec.).

IR(KBr,cm$^{-1}$): 3298,3070,2926,2854,1650,1542,1455,1389, 1344,1233,1098,741.

High Resolution FAB-MS(m/e,(C$_{32}$H$_{44}$N$_6$O$_7$+H)$^+$):

Calcd : 625.3350.

Found : 625.3358.

$^1$H-NMR(300 MHz,DMSO-d$_6$,δ ppm):0.66-1.88(14H,m),0.82(3H,d,J=6.5Hz),0.83(3H,d,J=6.6Hz),1.11(3H,d,J=6.8Hz),2.28-2.50(1H,m),2.67-2.80(1H,m),2.82-2.97(1H,m),3.14-3.40(1H,m),4.04-4.20(2H,m),4.28-4.58(3H,m),6.95(1H,t,J=7.5Hz),7.04(1H,t,J=7.5Hz),7.08(1H,d,J=2.3Hz),7.31(1H,d,J=7.5Hz),7.39(1H,d,J=9.5Hz),7.52(1H,d,J=7.5Hz),7.58(1H,d,J=7.4Hz),8.64(1H,d,J=6.3Hz),8.68(1H,d,J=8.8Hz),8.73(1H,d,J=7.7Hz),10.79(1H,brs),12.22(1H,brs).

EXAMPLE 95 cyclo(-DPhe-DAsp-Pro-DVal-Leu-)

m.p.: >300° C.

IR(KBr,cm$^{-1}$): 2926,2854,1633,1542,1254,1068.

FAB-MS(m/e,(C$_{29}$H$_{41}$N$_5$O$_7$+H)$^+$):572.

$^1$H-NMR(300 MHz,DMSO-d$_6$,δ ppm):0.60(3H,d,J=6.3Hz),0.70(3H,d,J=6.4Hz),0.82(3H,d,J=6.5Hz),0.85(3H,d,J=6.5Hz),1.15-1.17(2H,m),1.20-1.25(1H,m),1.64-1.70(1H,m),1.73-1.82(1H,m),1.84-1.98(1H,m),2.22-2.28(2H,m), 2.35(1H,dd,J=4.0Hz,16.0Hz),2.63-2.77(1H,m),2.80(1H,dd, J=10.4Hz,16.0Hz),2.90-3.62(3H,m),3.88-3.99(1H,m),4.14(1H,dd,J=7.8Hz,10.2Hz),4.21-4.32(1H,m),4.76(1H,d-like, J=7.0Hz),4.88-5.06(1H,m),7.16-7.24(5H,m),7.50(1H,d,J=10.2Hz),7.76(1H,d,J=9.3Hz),8.77(1H,d,J=4.9Hz),8.90(1H,d,J=8.1Hz).

EXAMPLE 96 cyclo(-DTyr-DAsp-Pro-DVal-Leu-)

m.p.: 180°-184° C.

IR(KBr,cm$^{-1}$): 3442,2968,1659,1521,1455,1230,830.

High Resolution FAB-MS(m/e,(C$_{29}$H$_{41}$N$_5$O$_8$+H)$^+$):

Calcd : 588.3033.

Found : 588.3055.

$^1$H-NMR(300 MHz,DMSO-d$_6$,δ ppm):0.65(3H,d,J=6.4Hz),0.75(3H,d,J=6.4Hz),0.82(3H,d,J=6.6Hz),0.85(3H,d,J=6.6Hz),0.89-1.07(1H,m),1.14-1.34(2H,m),1.53-1.82(3H,m),1.83-1.98(1H,m),2.21-2.31(1H,m),2.34(1H,dd,J=3.9Hz, 16.0Hz),2.55-2.63(1H,m),2.79(1H,dd,J=10.4Hz,16.0Hz),3.07-3.18(2H,m),3.30-3.42(1H,m),3.92-4.00(1H,m),4.11-4/22(2H,m),4.76(1H,d-like,J=7.4Hz),4.80-4.97(1H,m),6.60(2H,d,J=8.3Hz),7.01(2H,d,J=8.3Hz),7.48(1H,d,J=10.0Hz),7.73(1H,d,J=8.8Hz),8.77(1H,d,J=5.1Hz),8.81(1H,d,J=8.6Hz),9.12(1H,s),12.31(1H,brs).

EXAMPLE 97 cyclo(-DNal-DGlu-Ala-DVal-Leu-)

m.p.: 270° C.(dec.).

IR(KBr,cm$^{-1}$): 3466,3286,2926,1644,1551,1389.

High Resolution FAB-MS(m/e,(C$_{32}$H$_{43}$N$_5$O$_7$+H)$^+$):

Calcd : 610.3240.

Found : 610.3237.

$^1$H-NMR(300 MHz,DMSO-d$_6$,δ ppm):0.59(3H,d,J=5.4Hz),0.75-0.95(9H,m),1.13(3H,d, J=7.1Hz),1.15-1.25(3H,m), 1.75-1.85(1H,m),1.-85-2.05(2H,m),2.-05-2.25(2H,m),3.09(1H,dd,J=11.5Hz,14.1Hz),3.80(1H,dd,J=2.1Hz,14.1Hz),
4.05-4.15(1H,m),4.15(1H,dd,J=6.8Hz,9.1Hz),4.29(1H,q,J=6.5Hz),4.40-4.50(2H,m),7.37(1H,t,J=7.4Hz),7.43-(1H,d,
J=7.4Hz),7.45-7.65(4H,m),7.78(1H,d,J=8.1Hz),7.93(1H,d,J=7.9Hz),8.20(1H,d,J=8.3Hz),8.60(1H,d,J=6.1Hz),8.75(1H,d,J=7.6Hz),8.98(1H,d,J=9.1Hz).

EXAMPLE 98 cyclo(-DTrp-DAsp-trans-Hyp-DCpg-Leu-)

According to the same procedure described in Example 6, the title compound was prepared from Fmoc-Leu, Fmoc-DCpg, Fmoc-trans-Hyp(O'Bu), Fmoc-DAsp-(O'Bu), and Fmoc-DTrp.

m.p. 173.5°-180.0° C.

IR(KBr,cm$^{-1}$):
3310,3064,2962,1662,1536,1446,1287,1233, 1176,744.

Calcd : 653.3299.
Found : 653.3267.

$^1$H-NMR(300MHZ,DMSO-d$_6$,δ ppm):0.60(3H,d,J=6.2Hz),0.72(3H,d,J=6.4Hz),0.95-1.38(5H,m),1.40-1.75(7H,m),
1.85-2.03(1H,m),2.30(1H,dd,J=4.2Hz,16.2Hz),2.35-2.53(1H,m),2.77(1H,dd,J=11.2Hz,16.2Hz),2.86(1H,dd,J=11.9Hz,14.3Hz),3.07(1H,dd,J=4.3Hz,11.1Hz),3.18(1H,dd,J=5.5Hz,11.1Hz),3.34(1H,dd,J=2.8Hz,14.3Hz),-3.90-4.00(1H,
m),4.14-4.32(2H,m),4.16(1H,t,J=10.1Hz),4.81(1H,dd,J=2.5Hz,8.1Hz),4.90-5.07(2H,m),6.95(1H,t,J=7.5Hz),7.04(1H,t,J=7.5Hz),7.13(1H,d,J=1.5Hz),7.31(1H,d,J=7.5Hz),7.37(1H,d,J=7.5Hz),7.51(1H,d,J=7.5Hz),7.80(1H,
d,J=9.3Hz),8.67-8.85(2H,m),10.79(1H,d,J=1.5Hz).

EXAMPLE 99

Production of a transfusion solution for drip infusion

The compound prepared in Example 59, cyclo (-DTrp-DAsp(ONa)-Pro-DVal-Leu-)(1 g) was dissolved in 500 ml of a 5% glucose solution for transfusion. The resulting solution was filtered through a milipore filter(pore size, 0.22 μm) under aseptic conditions. A transfusion vial was filled with the filtrate to afford a transfusion solution for drip infusion.

EXAMPLE 100

Production of a solution for intravenous injection

The compound prepared in Example 59, cyclo (-DTrp-DAsp(ONa)-Pro-DVal-Leu-)(1 g) was dissolved in 100 ml of an aqueous, isotonic sodium chloride solution. The resulting solution was filtered through a milipore filter(pore size, 0.22 μm) under aseptic conditions to afford a solution for intravenous injection.

EXAMPLE 101

| Production of tablets | |
|---|---|
| cyclo(-DTrp-DAsp(ONa)-Pro-DVal-Leu-) | 7 parts |
| Hydroxypropylcellulose | 1 part |

-continued

| Production of tablets | |
|---|---|
| Lactose | 10.9 parts |
| Corn starch | 1 part |
| Magnesium stearate | 0.1 parts |

The compound prepared in Example 59, cyclo (-DTrp-nAsp(ONa)-Pro-DVal-Leu-)(7 parts), 10.9 parts of lactose and one part of corn starch, were blended thoroughly with 5 parts of a 60% aqueous ethanol solution containing one part of hydroxypropyl cellulose. The mixture was dried under reduced pressure, mixed with 0.1 parts of magnesium stearate and compressed by a conventional method into tablets.

The cyclic pentapeptides have a potent antagonistic activity against endothelin which is an endogenous peptide with potent vasoconstrictor and other activities. Therefore, they are useful as drugs which exhibit antagonism against vascular and trachea smooth muscles contraction effects by endothelin. Particularly, they are useful as drugs for treating human hypertension, asthma, acute renal failure, myocardial infarction, angina pectoris, cerebral infarction or cerebral vasospasm. Further, they are useful also as drugs for treating endotoxin shock, or endotoxin-induced multiple organ failure or disseminated intravascular coagulation as well as cyclosporin-induced renal failure or hypertension.

What is claimed is:

1. A cyclic pentapeptide of the formula:

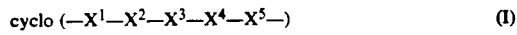

wherein $X^n$ (n=1-5) represents amino acid residues, respectively, and $X^1$ is D-Phe, D-Tyr, D-Tha, D-Tza, D-Nal, D-Bta, D-Trp, D-Trp(O), D-Trp(CHO) or D-Trp((CH$_2$)$_m$COR$^1$), wherein m is from 0 to 6, and R$^1$ is a hydroxyl group, a C$_1$-C$_6$ alkoxy group, an amino group or a C$_1$-C$_6$ monoalkylamino group, provided that when m=0, R$^1$ is not a hydroxyl group; $X^2$ is D-Asp, D-Glu, or D-Cys(O$_3$H); $X^3$ is Pro, Hyp, Pip, Thz, β-Ala, Gly, Ala, α-Aba, Aib, Val, Nva, Leu, Ile, aIle, Nle, Met, Met(O), Met(O$_2$), Phe, Tza, Tha, Tyr, Trp, His, Arg, Lys, Lys(CHO), Orn, Orn(CHO), Asn, Gln, Asp, Glu, Cys(O$_3$H), Cys, Ser or Thr wherein those α-amino acids having a hydrogen atom on the α-amino group are optionally substituted by a C$_1$-C$_6$ alkyl or C$_3$-C$_7$ cycloalkyl group which optionally has a group selected from the group consisting of an imidazolyl group, a carboxyl group, a sulfo group and a hydroxy group; $X^4$ is D-Ala, D-Thr, D-α-Aba, D-Val, D-Nva, D-Leu, D-Ile, D-aIle, D-Nle, D-tert-Leu, D-Cpg, D-Chg, D-Dpg, D-Pen, Aib, Ac$_3$c, Ac$_4$c, Ac$_5$c, Ac$_6$c, Ac$_7$c, D-Phg, D-Thg, D-Fug, D-Tzg or D-Itg wherein those α-amino acids having a hydrogen atom at the α-position are optionally substituted by a C$_1$-C$_3$ alkyl group; $X^5$ is Pro, Pip, Thz, His, Ala, α-Aba, Val, Nva, Leu, Ile, aIle, Nle, Met, C$_3$al, C$_4$al, C$_5$al or C$_6$al wherein those α-amino acids having hydrogen atom on the α-amino group are optionally substituted by a C$_1$-C$_6$ alkyl group; or a pharmaceutically acceptable salt thereof.

2. A pharmaceutical composition comprising an effective amount of a cyclic pentapeptide of the formula (I) as defined in claim 1 or a pharmaceutically acceptable salt thereof and a pharmaceutically acceptable carrier.

* * * * *